(12) United States Patent
Heras et al.

(10) Patent No.: US 11,897,941 B2
(45) Date of Patent: Feb. 13, 2024

(54) COMPOSITIONS AND METHODS FOR REDUCING BACTERIAL AGGREGATION

(71) Applicants: La Trobe University, Bundoora (AU); The University of Queensland, St. Lucia (AU)

(72) Inventors: Begona Heras, Victoria (AU); Jason Paxman, Victoria (AU); Mark Schembri, Queensland (AU); Alvin Lo, Victoria (AU)

(73) Assignees: La Trobe University, Bundoora (AU); The University of Queensland, St. Lucia (AU)

( * ) Notice: Subject to any disclaimer, the term of this patent is extended or adjusted under 35 U.S.C. 154(b) by 0 days.

(21) Appl. No.: 17/181,491

(22) Filed: Feb. 22, 2021

(65) Prior Publication Data

US 2021/0292397 A1 Sep. 23, 2021

Related U.S. Application Data

(63) Continuation of application No. PCT/AU2019/050893, filed on Aug. 23, 2019.

(30) Foreign Application Priority Data

Aug. 23, 2018 (AU) .................................. 2018903096

(51) Int. Cl.
```
C07K 16/12      (2006.01)
A61P 31/04      (2006.01)
A01N 63/50      (2020.01)
A61K 39/40      (2006.01)
A61K 45/06      (2006.01)
```
(52) U.S. Cl.
CPC .......... *C07K 16/1232* (2013.01); *A01N 63/50* (2020.01); *A61K 39/40* (2013.01); *A61K 45/06* (2013.01); *A61P 31/04* (2018.01); *C07K 2317/51* (2013.01); *C07K 2317/515* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2012/0207776 A1   8/2012   Serino et al.
2015/0158941 A1*  6/2015   Gutierrez ......... A61K 39/39575
                                                     536/23.53

FOREIGN PATENT DOCUMENTS

WO   WO 2004/009759 A2   1/2004
WO   WO 2007/124591 A2   7/2007
WO   WO 2007/082105 A1   11/2007
WO   WO 2012/054879 A1   4/2012
WO   WO 2013/185130 A2   12/2013

OTHER PUBLICATIONS

Almagro et al. Frontiers in Bioscience 13:1619-1633, 2008.*
Edwards et al J. Mol. Biol. (2003) 334, 103-118.*
Lloyd et al . Protein Engineering, Design & Selection vol. 22, No. 3 pp. 159-168, 2009.*
Uniprot accession # A0A8G1CFQ2 Jan. 19, 2022.*
International Search Report and Written Opinion for Application No. PCT/AU2019/050893, dated Nov. 4, 2019.
International Preliminary Report on Patentability for Application No. PCT/AU2019/050893, dated Mar. 4, 2021.
Arenas et al., Involvement of three meningococcal surface-exposed proteins, the heparin-binding protein NhbA, the α-peptide of IgA protease and the auto transporter protease NaIP, in initiation of biofilm formation. Mol Microbiol. Jan. 2013;87(2):254-68. doi: 10.1111/mmi.12097. Epub Dec. 4, 2012.
Paxman et al., Unique structural features of a bacterial autotransporter adhesin suggest mechanisms for interaction with host macromolecules. Nat Commun. Apr. 29, 2019;10(1):1967. doi: 10.1038/s41467-019-09814-6.
Shakerimoghaddam et al., Zinc oxide nanoparticle reduced biofilm formation and antigen 43 expressions in uropathogenic *Escherichia coli*. Iran J Basic Med Sci. Apr. 2017;20(4):451-456. doi: 10.22038/IJBMS.2017.8589.
Extended European Search Report for Application No. EP19851203.0, dated Apr. 20, 2022.
Dai et al., Suppression subtractive hybridization identifies an autotransporter adhesin gene of *E. coli* IMT5155 specifically associated with avian pathogenic *Escherichia coli* (APEC). BMC Microbiol. Sep. 9, 2010;10:236. doi: 10.1186/1471-2180-10-236.
Harris et al., Directed evaluation of enterotoxigenic *Escherichia coli* autotransporter proteins as putative vaccine candidates. PLoS Negl Trop Dis. Dec. 2011;5(12):e1428. doi: 10.1371/journal.pntd.0001428. Epub Dec. 6, 2011.
Kingsley et al., Fibronectin binding to the *Salmonella enterica* serotype Typhimurium ShdA autotransporter protein is inhibited by a monoclonal antibody recognizing the A3 repeat. J Bacteriol. Aug. 2004;186(15):4931-9. doi: 10.1128/JB.186.15.4931-4939.2004.
Lindenthal et al., Enterotoxigenic *Escherichia coli* TibA glycoprotein adheres to human intestine epithelial cells. Infect Immun. Jan. 2001;69(1):52-7. doi: 10.1128/IAI.69.1.52-57.2001.
Wells et al., EhaA is a novel autotransporter protein of enterohemorrhagic *Escherichia coli* O157:H7 that contributes to adhesion and biofilm formation. Environ Microbiol. Mar. 2008;10(3):589-604. doi: 10.1111/j.1462-2920.2007.01479.x.

\* cited by examiner

*Primary Examiner* — Oluwatosin A Ogunbiyi
(74) *Attorney, Agent, or Firm* — Wolf, Greenfield & Sacks, P.C.

(57) ABSTRACT

The present disclosure relates to compositions and methods for inhibiting bacterial aggregation, and in particular, to compositions and methods that inhibit autotransporter-mediated bacterial aggregation or attachment. Described herein are autotransporter binding molecules such as antibodies and antigen binding fragments thereof. The autotransporter binding molecules block self-association between autotransporters and autotransporter-mediated surface attachment.

14 Claims, 23 Drawing Sheets

Specification includes a Sequence Listing.

A

B

C

A

B

C

D

E

F

G

A

B

C

SEQUENCE LISTING

```
<160> NUMBER OF SEQ ID NOS: 49

<210> SEQ ID NO 1
<211> LENGTH: 1042
<212> TYPE: PRT
<213> ORGANISM: Escherichia coli

<400> SEQUENCE: 1

Met Leu Met Lys Arg His Leu Asn Thr Cys Tyr Arg Leu Val Trp Asn
1               5                   10                  15

His Ile Thr Gly Ala Phe Val Val Ala Ser Glu Leu Ala Arg Ala Arg
            20                  25                  30

Gly Lys Arg Gly Gly Val Ala Val Ala Leu Ser Leu Ala Ala Val Thr
        35                  40                  45

Pro Leu Pro Val Leu Ser Ala Asp Ile Val Val His Pro Gly Glu Thr
    50                  55                  60

Val Asn Gly Gly Thr Leu Val Asn His Asp Asn Gln Phe Val Ser Gly
65                  70                  75                  80

Thr Ala Asn Gly Val Thr Val Ser Thr Gly Leu Glu Leu Gly Pro Asp
                85                  90                  95

Ser Asp Glu Asn Thr Gly Gly Gln Trp Ile Lys Ala Gly Gly Thr Gly
            100                 105                 110

Arg Asn Thr Thr Val Thr Ala Asn Gly Arg Gln Ile Val Gln Ala Gly
        115                 120                 125
```

```
Gly Thr Ala Ser Asp Thr Val Ile Arg Asp Gly Gly Gln Ser Leu
    130                 135                 140

Asn Gly Leu Ala Val Asn Thr Thr Leu Asp Asn Arg Gly Glu Gln Trp
145                 150                 155                 160

Val His Gly Gly Lys Ala Ala Gly Thr Ile Ile Asn Gln Asp Gly
                165                 170                 175

Tyr Gln Thr Ile Lys His Gly Gly Leu Ala Thr Gly Thr Ile Val Asn
                180                 185                 190

Thr Gly Ala Glu Gly Gly Pro Glu Ser Glu Asn Val Ser Ser Gly Gln
                195                 200                 205

Met Val Gly Gly Thr Ala Glu Ser Thr Thr Ile Asn Lys Asn Gly Arg
    210                 215                 220

Gln Val Ile Trp Ser Ser Gly Met Ala Arg Asp Thr Leu Ile Tyr Ala
225                 230                 235                 240

Gly Gly Asp Gln Thr Val His Gly Glu Ala His Asn Thr Arg Leu Glu
                245                 250                 255

Gly Gly Asn Gln Tyr Val His Asn Gly Gly Thr Ala Thr Glu Thr Leu
                260                 265                 270

Ile Asn Arg Asp Gly Trp Gln Val Ile Lys Glu Gly Gly Thr Ala Ala
            275                 280                 285

His Thr Thr Ile Asn Gln Lys Gly Lys Leu Gln Val Asn Ala Gly Gly
    290                 295                 300

Lys Ala Ser Asp Val Thr Gln Asn Thr Gly Gly Ala Leu Val Thr Ser
305                 310                 315                 320

Thr Ala Ala Thr Val Thr Gly Thr Asn Arg Leu Gly Ala Phe Ser Val
                325                 330                 335

Val Ala Gly Lys Ala Asp Asn Val Val Leu Glu Asn Gly Gly Arg Leu
                340                 345                 350

Asp Val Leu Ser Gly His Thr Ala Thr Asn Thr Arg Val Asp Asp Gly
            355                 360                 365

Gly Thr Leu Asp Ile Arg Asn Gly Gly Ala Ala Thr Thr Val Ser Met
    370                 375                 380

Gly Asn Gly Gly Val Leu Leu Ala Asp Ser Gly Ala Ala Val Ser Gly
385                 390                 395                 400

Thr Arg Ser Asp Gly Lys Ala Phe Ser Ile Gly Gly Gly Gln Ala Asp
                405                 410                 415

Ala Leu Met Leu Glu Lys Gly Ser Ser Phe Thr Leu Asn Ala Gly Asp
                420                 425                 430

Thr Ala Thr Asp Thr Thr Val Asn Gly Gly Leu Phe Thr Ala Arg Gly
            435                 440                 445

Gly Thr Leu Ala Gly Thr Thr Thr Leu Asn Asn Gly Ala Ile Leu Thr
    450                 455                 460

Leu Ser Gly Lys Thr Val Asn Asn Asp Thr Leu Thr Ile Arg Glu Gly
465                 470                 475                 480

Asp Ala Leu Leu Gln Gly Gly Ser Leu Thr Gly Asn Gly Ser Val Glu
                485                 490                 495

Lys Ser Gly Ser Gly Thr Leu Thr Val Ser Asn Thr Thr Leu Thr Gln
                500                 505                 510

Lys Ala Val Asn Leu Asn Glu Gly Thr Leu Thr Leu Asn Asp Ser Thr
            515                 520                 525

Val Thr Thr Asp Val Ile Ala Gln Arg Gly Thr Ala Leu Lys Leu Thr
    530                 535                 540

Gly Ser Thr Val Leu Asn Gly Ala Ile Asp Pro Thr Asn Val Thr Leu
```

```
545                 550                 555                 560
Ala Ser Asp Ala Thr Trp Asn Ile Pro Asp Asn Ala Thr Val Gln Ser
                565                 570                 575

Val Val Asp Asp Leu Ser His Ala Gly Gln Ile His Phe Thr Ser Ser
                580                 585                 590

Arg Thr Gly Thr Phe Val Pro Ala Thr Leu Lys Val Lys Asn Leu Asn
                595                 600                 605

Gly Gln Asn Gly Thr Ile Ser Leu Arg Val Arg Pro Asp Met Ala Gln
            610                 615                 620

Asn Asn Ala Asp Arg Leu Val Ile Asp Gly Arg Ala Thr Gly Lys
625                 630                 635                 640

Thr Ile Leu Asn Leu Val Asn Ala Gly Asn Ser Ala Ser Gly Leu Ala
                645                 650                 655

Thr Ser Gly Lys Gly Ile Gln Val Val Glu Ala Ile Asn Gly Ala Thr
            660                 665                 670

Thr Glu Glu Gly Ala Phe Val Gln Gly Asn Arg Leu Gln Ala Gly Ala
        675                 680                 685

Phe Asn Tyr Ser Leu Asn Arg Asp Ser Asp Glu Ser Trp Tyr Leu Arg
    690                 695                 700

Ser Glu Asn Ala Tyr Arg Ala Glu Val Pro Leu Tyr Ala Ser Met Leu
705                 710                 715                 720

Thr Gln Ala Met Asp Tyr Asp Arg Ile Leu Ala Gly Ser Arg Ser His
                725                 730                 735

Gln Thr Gly Val Asn Gly Glu Asn Asn Ser Val Arg Leu Ser Ile Gln
            740                 745                 750

Gly Gly His Leu Gly His Asp Asn Asn Gly Gly Ile Ala Arg Gly Ala
        755                 760                 765

Thr Pro Glu Ser Ser Gly Ser Tyr Gly Phe Val Arg Leu Glu Gly Asp
    770                 775                 780

Leu Leu Arg Thr Asp Val Ala Gly Met Ser Val Thr Ala Gly Ile Tyr
785                 790                 795                 800

Gly Ala Ala Gly His Ser Ser Val Asp Val Lys Asp Asp Gly Ser
                805                 810                 815

Arg Ala Gly Thr Val Arg Asp Asp Ala Gly Ser Leu Gly Gly Tyr Met
                820                 825                 830

Asn Leu Thr His Thr Ser Ser Gly Leu Trp Ala Asp Ile Val Ala Gln
            835                 840                 845

Gly Thr Arg His Ser Met Lys Ala Ser Ser Gly Asn Asn Asp Phe Arg
        850                 855                 860

Ala Arg Gly Arg Gly Trp Leu Gly Ser Leu Glu Thr Gly Leu Pro Phe
865                 870                 875                 880

Ser Ile Thr Asp Asn Leu Met Leu Glu Pro Arg Leu Gln Tyr Thr Trp
                885                 890                 895

Gln Gly Leu Ser Leu Asp Asp Gly Lys Asp Asn Ala Gly Tyr Val Lys
            900                 905                 910

Phe Gly His Gly Ser Ala Gln His Val Arg Ala Gly Phe Arg Leu Gly
        915                 920                 925

Ser His Asn Asp Met Thr Phe Gly Glu Gly Thr Ser Ser Arg Ala Pro
    930                 935                 940

Leu Arg Asp Ser Ala Lys His Ser Val Arg Glu Leu Pro Val Asn Trp
945                 950                 955                 960

Trp Val Gln Pro Ser Val Ile Arg Thr Phe Ser Ser Arg Gly Asp Met
                965                 970                 975
```

```
Arg Val Gly Thr Ser Thr Ala Gly Ser Gly Met Thr Phe Ser Pro Ser
            980                 985                 990

Gln Asn Gly Thr Ser Leu Asp Leu Gln Ala Gly Leu Glu Ala Arg Val
            995                1000                1005

Arg Glu Asn Ile Thr Leu Gly Val Gln Ala Gly Tyr Ala His Ser
       1010                1015                1020

Val Ser Gly Ser Ser Ala Glu Gly Tyr Asn Gly Gln Ala Thr Leu
       1025                1030                1035

Asn Val Thr Phe
       1040

<210> SEQ ID NO 2
<211> LENGTH: 500
<212> TYPE: PRT
<213> ORGANISM: Escherichia coli

<400> SEQUENCE: 2

Ala Asp Ile Val Val His Pro Gly Glu Thr Val Asn Gly Gly Thr Leu
1               5                   10                  15

Val Asn His Asp Asn Gln Phe Val Ser Gly Thr Ala Asn Gly Val Thr
            20                  25                  30

Val Ser Thr Gly Leu Glu Leu Gly Pro Asp Ser Asp Glu Asn Thr Gly
        35                  40                  45

Gly Gln Trp Ile Lys Ala Gly Thr Gly Arg Asn Thr Thr Val Thr
    50                  55                  60

Ala Asn Gly Arg Gln Ile Val Gln Ala Gly Thr Ala Ser Asp Thr
65                  70                  75                  80

Val Ile Arg Asp Gly Gly Gln Ser Leu Asn Gly Leu Ala Val Asn
                85                  90                  95

Thr Thr Leu Asp Asn Arg Gly Glu Gln Trp Val His Gly Gly Gly Lys
                100                 105                 110

Ala Ala Gly Thr Ile Ile Asn Gln Asp Gly Tyr Gln Thr Ile Lys His
            115                 120                 125

Gly Gly Leu Ala Thr Gly Thr Ile Val Asn Thr Gly Ala Glu Gly Gly
        130                 135                 140

Pro Glu Ser Glu Asn Val Ser Ser Gly Gln Met Val Gly Gly Thr Ala
145                 150                 155                 160

Glu Ser Thr Thr Ile Asn Lys Asn Gly Arg Gln Val Ile Trp Ser Ser
                165                 170                 175

Gly Met Ala Arg Asp Thr Leu Ile Tyr Ala Gly Gly Asp Gln Thr Val
            180                 185                 190

His Gly Glu Ala His Asn Thr Arg Leu Glu Gly Gly Asn Gln Tyr Val
        195                 200                 205

His Asn Gly Gly Thr Ala Thr Glu Thr Leu Ile Asn Arg Asp Gly Trp
    210                 215                 220

Gln Val Ile Lys Glu Gly Gly Thr Ala Ala His Thr Thr Ile Asn Gln
225                 230                 235                 240

Lys Gly Lys Leu Gln Val Asn Ala Gly Gly Lys Ala Ser Asp Val Thr
                245                 250                 255

Gln Asn Thr Gly Gly Ala Leu Val Thr Ser Thr Ala Ala Thr Val Thr
            260                 265                 270

Gly Thr Asn Arg Leu Gly Ala Phe Ser Val Ala Gly Lys Ala Asp
        275                 280                 285

Asn Val Val Leu Glu Asn Gly Gly Arg Leu Asp Val Leu Ser Gly His
```

```
                290                 295                 300

Thr Ala Thr Asn Thr Arg Val Asp Asp Gly Gly Thr Leu Asp Ile Arg
305                 310                 315                 320

Asn Gly Gly Ala Ala Thr Thr Val Ser Met Gly Asn Gly Gly Val Leu
                325                 330                 335

Leu Ala Asp Ser Gly Ala Ala Val Ser Gly Thr Arg Ser Asp Gly Lys
                340                 345                 350

Ala Phe Ser Ile Gly Gly Gln Ala Asp Ala Leu Met Leu Glu Lys
            355                 360                 365

Gly Ser Ser Phe Thr Leu Asn Ala Gly Asp Thr Ala Thr Asp Thr Thr
        370                 375                 380

Val Asn Gly Gly Leu Phe Thr Ala Arg Gly Gly Thr Leu Ala Gly Thr
385                 390                 395                 400

Thr Thr Leu Asn Asn Gly Ala Ile Leu Thr Leu Ser Gly Lys Thr Val
                405                 410                 415

Asn Asn Asp Thr Leu Thr Ile Arg Glu Gly Asp Ala Leu Leu Gln Gly
                420                 425                 430

Gly Ser Leu Thr Gly Asn Gly Ser Val Glu Lys Ser Gly Ser Gly Thr
        435                 440                 445

Leu Thr Val Ser Asn Thr Thr Leu Thr Gln Lys Ala Val Asn Leu Asn
    450                 455                 460

Glu Gly Thr Leu Thr Leu Asn Asp Ser Thr Val Thr Thr Asp Val Ile
465                 470                 475                 480

Ala Gln Arg Gly Thr Ala Leu Lys Leu Thr Gly Ser Thr Val Leu Asn
                485                 490                 495

Gly Ala Ile Asp
        500

<210> SEQ ID NO 3
<211> LENGTH: 9
<212> TYPE: PRT
<213> ORGANISM: Artificial Sequence
<220> FEATURE:
<223> OTHER INFORMATION: Fab7D10 CDRH1

<400> SEQUENCE: 3

Tyr Thr Phe Thr Asp Tyr Trp Leu Tyr
1               5

<210> SEQ ID NO 4
<211> LENGTH: 14
<212> TYPE: PRT
<213> ORGANISM: Artificial Sequence
<220> FEATURE:
<223> OTHER INFORMATION: Fab7D10 CDRH2

<400> SEQUENCE: 4

Trp Ile Gly Asn Ile Ile Pro Phe Asn Gly Gly Ser Asn Tyr
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Fab7D10 CDRH3

<400> SEQUENCE: 5

Arg Arg Gly Thr Arg Ala Met Asp Tyr
1               5
```

<210> SEQ ID NO 6
<211> LENGTH: 8
<212> TYPE: PRT
<213> ORGANISM: Artificial Sequence
<220> FEATURE:
<223> OTHER INFORMATION: Fab7D10 CDRL1

<400> SEQUENCE: 6

Gln Ser Val Ser Tyr Asp Val Ala
1               5

<210> SEQ ID NO 7
<211> LENGTH: 11
<212> TYPE: PRT
<213> ORGANISM: Artificial Sequence
<220> FEATURE:
<223> OTHER INFORMATION: Fab7D10 CDRL2

<400> SEQUENCE: 7

Leu Leu Ile Phe Tyr Val Ser Asn Arg Ser Thr
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Fab7D10 CDRL3

<400> SEQUENCE: 8

Gln Gln Asp Tyr Ser Ser Pro Phe
1               5

<210> SEQ ID NO 9
<211> LENGTH: 117
<212> TYPE: PRT
<213> ORGANISM: Artificial Sequence
<220> FEATURE:
<223> OTHER INFORMATION: Fab7D10 VH

<400> SEQUENCE: 9

Gln Val Gln Leu Gln Gln Pro Gly Thr Glu Val Val Lys Pro Gly Ala
1               5                   10                  15

Ser Val Lys Leu Ser Cys Lys Ala Ser Gly Tyr Thr Phe Thr Asp Tyr
            20                  25                  30

Trp Leu Tyr Trp Val Lys Gln Arg Pro Gly Gln Gly Leu Asp Trp Ile
        35                  40                  45

Gly Asn Ile Ile Pro Phe Asn Gly Gly Ser Asn Tyr Asn Glu Lys Phe
    50                  55                  60

Lys Asn Lys Ala Thr Leu Thr Val Asp Glu Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Thr Arg Ala Met Asp Tyr Trp Gly Gln Gly Thr Ser
            100                 105                 110

Val Thr Val Ser Ser
        115

<210> SEQ ID NO 10
<211> LENGTH: 107
<212> TYPE: PRT
<213> ORGANISM: Artificial Sequence

```
<220> FEATURE:
<223> OTHER INFORMATION: Fab7D10 VL

<400> SEQUENCE: 10

Ser Ile Val Met Thr Gln Thr Pro Lys Ser Leu Leu Val Ser Ala Gly
1               5                   10                  15

Asp Arg Val Ser Ile Thr Cys Lys Ala Ser Gln Ser Val Ser Tyr Asp
            20                  25                  30

Val Ala Trp Tyr Gln Gln Lys Pro Gly Gln Ser Pro Lys Leu Leu Ile
        35                  40                  45

Phe Tyr Val Ser Asn Arg Ser Thr Gly Val Pro Glu Arg Phe Thr Gly
    50                  55                  60

Ser Gly Tyr Gly Thr Asp Phe Thr Phe Thr Ile Ser Thr Val Gln Pro
65                  70                  75                  80

Glu Asp Leu Ala Val Tyr Phe Cys Gln Gln Asp Tyr Ser Ser Pro Phe
                85                  90                  95

Thr Phe Gly Gly Gly Thr Lys Leu Glu Leu Lys
            100                 105

<210> SEQ ID NO 11
<211> LENGTH: 102
<212> TYPE: PRT
<213> ORGANISM: Artificial Sequence
<220> FEATURE:
<223> OTHER INFORMATION: Fab7D10 CH1

<400> SEQUENCE: 11

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys
            100

<210> SEQ ID NO 12
<211> LENGTH: 107
<212> TYPE: PRT
<213> ORGANISM: Artificial Sequence
<220> FEATURE:
<223> OTHER INFORMATION: Fab7D10 CL

<400> SEQUENCE: 12

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60
```

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 13
<211> LENGTH: 225
<212> TYPE: PRT
<213> ORGANISM: Artificial Sequence
<220> FEATURE:
<223> OTHER INFORMATION: Fab7D10 heavy chain

<400> SEQUENCE: 13

Gln Val Gln Leu Gln Gln Pro Gly Thr Glu Val Val Lys Pro Gly Ala
1               5                   10                  15

Ser Val Lys Leu Ser Cys Lys Ala Ser Gly Tyr Thr Phe Thr Asp Tyr
            20                  25                  30

Trp Leu Tyr Trp Val Lys Gln Arg Pro Gly Gln Gly Leu Asp Trp Ile
        35                  40                  45

Gly Asn Ile Ile Pro Phe Asn Gly Gly Ser Tyr Asn Glu Lys Phe
50                  55                  60

Lys Asn Lys Ala Thr Leu Thr Val Asp Glu Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Thr Arg Ala Met Asp Tyr Trp Gly Gln Gly Thr Ser
            100                 105                 110

Val Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Gln Thr Val Thr Cys Asn Val Ala His Pro Ala Ser Ser Thr
            195                 200                 205

Lys Val Asp Lys Lys Ile Val Pro Arg Asp Cys His His His His
210                 215                 220

His
225

<210> SEQ ID NO 14
<211> LENGTH: 214
<212> TYPE: PRT
<213> ORGANISM: Artificial Sequence
<220> FEATURE:
<223> OTHER INFORMATION: Fab7D10 light chain

<400> SEQUENCE: 14

Ser Ile Val Met Thr Gln Thr Pro Lys Ser Leu Leu Val Ser Ala Gly
1               5                   10                  15

Asp Arg Val Ser Ile Thr Cys Lys Ala Ser Gln Ser Val Ser Tyr Asp
            20                  25                  30

Val Ala Trp Tyr Gln Gln Lys Pro Gly Gln Ser Pro Lys Leu Leu Ile
            35                  40                  45

Phe Tyr Val Ser Asn Arg Ser Thr Gly Val Pro Glu Arg Phe Thr Gly
        50                  55                  60

Ser Gly Tyr Gly Thr Asp Phe Thr Phe Thr Ile Ser Thr Val Gln Pro
65                  70                  75                  80

Glu Asp Leu Ala Val Tyr Phe Cys Gln Gln Asp Tyr Ser Ser Pro Phe
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210

<210> SEQ ID NO 15
<211> LENGTH: 9
<212> TYPE: PRT
<213> ORGANISM: Artificial Sequence
<220> FEATURE:
<223> OTHER INFORMATION: Fab10C12 CDRH1

<400> SEQUENCE: 15

Tyr Thr Phe Thr Asn Tyr Trp Met His
1               5

<210> SEQ ID NO 16
<211> LENGTH: 14
<212> TYPE: PRT
<213> ORGANISM: Artificial Sequence
<220> FEATURE:
<223> OTHER INFORMATION: Fab10C12 CDRH2

<400> SEQUENCE: 16

Trp Ile Gly Asn Ile Gly Pro Ser Ser Gly Asn Thr Asn Tyr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Fab10C12 CDRH3

<400> SEQUENCE: 17

Arg Trp Gly Ser Ile Arg Ala Met Asp Tyr
1               5                   10

<210> SEQ ID NO 18
<211> LENGTH: 8

<212> TYPE: PRT
<213> ORGANISM: Artificial Sequence
<220> FEATURE:
<223> OTHER INFORMATION: Fab10C12 CDRL1

<400> SEQUENCE: 18

Gln Ser Val Asn Asn Asp Val Ala
1               5

<210> SEQ ID NO 19
<211> LENGTH: 11
<212> TYPE: PRT
<213> ORGANISM: Artificial Sequence
<220> FEATURE:
<223> OTHER INFORMATION: Fab10C12 CDRL2

<400> SEQUENCE: 19

Leu Leu Ile Tyr Phe Ala Ser Asn Arg Tyr Thr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Fab10C12 CDRL3

<400> SEQUENCE: 20

Gln Gln Asp Tyr Ser Ser Pro Gln
1               5

<210> SEQ ID NO 21
<211> LENGTH: 118
<212> TYPE: PRT
<213> ORGANISM: Artificial Sequence
<220> FEATURE:
<223> OTHER INFORMATION: Fab10C12 VH

<400> SEQUENCE: 21

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Asn Ile Gly Pro Ser Ser Gly Asn Thr Asn Tyr Asn Glu Asn Phe
    50                  55                  60

Lys Thr Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Ser Ile Arg Ala Met Asp Tyr Trp Gly Gln Gly Thr
            100                 105                 110

Ser Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: Fab10C12 VL

<400> SEQUENCE: 22

Ser Ile Val Met Thr Gln Thr Pro Lys Phe Leu Phe Val Ser Val Gly
1               5                   10                  15

Asp Arg Val Thr Ile Thr Cys Lys Ala Ser Gln Ser Val Asn Asn Asp
            20                  25                  30

Val Ala Trp Tyr Gln Gln Lys Pro Gly Gln Ser Pro Lys Leu Leu Ile
            35                  40                  45

Tyr Phe Ala Ser Asn Arg Tyr Thr Gly Val Pro Asp Arg Phe Thr Gly
50                  55                  60

Ser Gly Tyr Gly Thr Asp Phe Thr Phe Thr Ile Asn Thr Val Gln Ala
65              70                  75                  80

Glu Asp Leu Ala Val Tyr Phe Cys Gln Gln Asp Tyr Ser Ser Pro Gln
                85                  90                  95

Thr Phe Gly Gly Gly Thr Lys Leu Glu Val Thr
            100                 105

<210> SEQ ID NO 23
<211> LENGTH: 97
<212> TYPE: PRT
<213> ORGANISM: Artificial Sequence
<220> FEATURE:
<223> OTHER INFORMATION: Fab10C12 CH1

<400> SEQUENCE: 23

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
            35                  40                  45

Ser Val His Thr Phe Pro Ala Leu Leu Gln Ser Gly Leu Tyr Thr Met
50                  55                  60

Ser Ser Ser Val Thr Val Pro Ser Ser Thr Trp Pro Ser Gln Thr Val
65              70                  75                  80

Thr Cys Ser Val Ala His Pro Ala Ser Ser Thr Thr Val Asp Lys Lys
                85                  90                  95

Leu

<210> SEQ ID NO 24
<211> LENGTH: 107
<212> TYPE: PRT
<213> ORGANISM: Artificial Sequence
<220> FEATURE:
<223> OTHER INFORMATION: Fab10C12 CL

<400> SEQUENCE: 24

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
50                  55                  60

Thr Tyr Ser Met Ser Ser Thr Leu Thr Leu Thr Lys Asp Glu Tyr Glu
65              70                  75                  80

Arg His Asn Ser Tyr Thr Cys Glu Ala Thr His Lys Thr Ser Thr Ser
                85                  90                  95

-continued

```
Pro Ile Val Lys Ser Phe Asn Arg Asn Glu Cys
            100                 105
```

<210> SEQ ID NO 25
<211> LENGTH: 221
<212> TYPE: PRT
<213> ORGANISM: Artificial Sequence
<220> FEATURE:
<223> OTHER INFORMATION: Fab10C12 heavy chain

<400> SEQUENCE: 25

```
Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Asn Ile Gly Pro Ser Ser Gly Asn Thr Asn Tyr Asn Glu Asn Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Gly Ser Ile Arg Ala Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu His His His His His
    210                 215                 220
```

<210> SEQ ID NO 26
<211> LENGTH: 214
<212> TYPE: PRT
<213> ORGANISM: Artificial Sequence
<220> FEATURE:
<223> OTHER INFORMATION: Fab10C12 light chain

<400> SEQUENCE: 26

```
Ser Ile Val Met Thr Gln Thr Pro Lys Phe Leu Phe Val Ser Val Gly
1               5                   10                  15

Asp Arg Val Thr Ile Thr Cys Lys Ala Ser Gln Ser Val Asn Asn Asp
            20                  25                  30

Val Ala Trp Tyr Gln Gln Lys Pro Gly Gln Ser Pro Lys Leu Leu Ile
        35                  40                  45

Tyr Phe Ala Ser Asn Arg Tyr Thr Gly Val Pro Asp Arg Phe Thr Gly
    50                  55                  60

Ser Gly Tyr Gly Thr Asp Phe Thr Phe Thr Ile Asn Thr Val Gln Ala
```

```
                65                  70                  75                  80
Glu Asp Leu Ala Val Tyr Phe Cys Gln Gln Asp Tyr Ser Ser Pro Gln
                    85                  90                  95
Thr Phe Gly Gly Gly Thr Lys Leu Glu Val Thr Arg Ala Asp Ala Ala
                100                 105                 110
Pro Thr Val Ser Ile Phe Pro Pro Ser Ser Glu Gln Leu Thr Ser Gly
            115                 120                 125
Gly Ala Ser Val Val Cys Phe Leu Asn Asn Phe Tyr Pro Lys Asp Ile
        130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 27
<211> LENGTH: 11
<212> TYPE: PRT
<213> ORGANISM: Escherichia coli

<400> SEQUENCE: 27

Leu Glu Leu Gly Pro Asp Ser Asp Glu Asn Thr
1               5                   10

<210> SEQ ID NO 28
<211> LENGTH: 11
<212> TYPE: PRT
<213> ORGANISM: Escherichia coli

<400> SEQUENCE: 28

Ala Glu Gly Gly Pro Glu Ser Glu Asn Val Ser
1               5                   10

<210> SEQ ID NO 29
<211> LENGTH: 17
<212> TYPE: PRT
<213> ORGANISM: Escherichia coli

<400> SEQUENCE: 29

Ala Ala Thr Val Thr Gly Thr Asn Arg Leu Gly Ala Phe Ser Val Val
1               5                   10                  15
Ala

<210> SEQ ID NO 30
<211> LENGTH: 17
<212> TYPE: PRT
<213> ORGANISM: Escherichia coli

<400> SEQUENCE: 30

Gly Ala Ala Val Ser Gly Thr Arg Ser Asp Gly Lys Ala Phe Ser Ile
1               5                   10                  15
Gly

<210> SEQ ID NO 31
```

<211> LENGTH: 948
<212> TYPE: PRT
<213> ORGANISM: Escherichia coli

<400> SEQUENCE: 31

```
Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Gly Ala Gly Val Ala Val Ala Leu Ser Leu Ala Ala Val Thr Ser Val
        35                  40                  45

Pro Ala Leu Ala Ala Asp Thr Val Gln Ala Gly Glu Thr Val Asn
    50                  55                  60

Gly Gly Thr Leu Thr Asn His Asp Asn Gln Ile Val Leu Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Val Asn Thr Gly Ala
            180                 185                 190

Glu Gly Gly Pro Asp Ala Glu Asn Gly Asp Thr Gly Gln Thr Val Tyr
        195                 200                 205

Gly Asp Ala Val Arg Thr Thr Ile Asn Lys Asn Gly Arg Gln Ile Val
210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255

Gln Tyr Val His Asn Gly Gly Thr Ala Ser Asp Thr Val Val Asn Ser
            260                 265                 270

Asp Gly Trp Gln Ile Ile Lys Glu Gly Gly Leu Ala Asp Phe Thr Thr
        275                 280                 285

Val Asn Gln Lys Gly Lys Leu Gln Val Asn Ala Gly Gly Thr Ala Thr
290                 295                 300

Asn Val Thr Leu Thr Gln Gly Gly Ala Leu Val Thr Ser Thr Ala Ala
305                 310                 315                 320

Thr Val Thr Gly Ser Asn Arg Leu Gly Asn Phe Thr Val Glu Asn Gly
                325                 330                 335

Asn Ala Asp Gly Val Val Leu Glu Ser Gly Gly Arg Leu Asp Val Leu
            340                 345                 350

Glu Gly His Ser Ala Trp Lys Thr Leu Val Asp Gly Gly Thr Leu
        355                 360                 365

Ala Val Ser Ala Gly Gly Lys Ala Thr Asp Val Thr Met Thr Ser Gly
370                 375                 380

Gly Ala Leu Ile Ala Asp Ser Gly Ala Thr Val Glu Gly Thr Asn Ala
```

```
                385                 390                 395                 400
        Ser Gly Lys Phe Ser Ile Asp Gly Ile Ser Gly Gln Ala Ser Gly Leu
                        405                 410                 415

Leu Leu Glu Asn Gly Gly Ser Phe Thr Val Asn Ala Gly Gly Leu Ala
                        420                 425                 430

Ser Asn Thr Thr Val Gly His Arg Gly Thr Leu Thr Leu Ala Ala Gly
                        435                 440                 445

Gly Ser Leu Ser Gly Arg Thr Gln Leu Ser Lys Gly Ala Ser Met Val
                        450                 455                 460

Leu Asn Gly Asp Val Val Ser Thr Gly Asp Ile Val Asn Ala Gly Glu
        465                 470                 475                 480

Ile Arg Phe Asp Asn Gln Thr Thr Pro Asp Ala Ala Leu Ser Arg Ala
                        485                 490                 495

Val Ala Lys Gly Asp Ser Pro Val Thr Phe His Lys Leu Thr Thr Ser
                        500                 505                 510

Asn Leu Thr Gly Gln Gly Gly Thr Ile Asn Met Arg Val Arg Leu Asp
                        515                 520                 525

Gly Ser Asn Ala Ser Asp Gln Leu Val Ile Asn Gly Gly Gln Ala Thr
                        530                 535                 540

Gly Lys Thr Trp Leu Ala Phe Thr Asn Val Gly Asn Ser Asn Leu Gly
        545                 550                 555                 560

Val Ala Thr Ser Gly Gln Gly Ile Arg Val Val Asp Ala Gln Asn Gly
                        565                 570                 575

Ala Thr Thr Glu Glu Gly Ala Phe Ala Leu Ser Arg Pro Leu Gln Ala
                        580                 585                 590

Gly Ala Phe Asn Tyr Thr Leu Asn Arg Asp Ser Asp Glu Asp Trp Tyr
                        595                 600                 605

Leu Arg Ser Glu Asn Ala Tyr Arg Ala Glu Val Pro Leu Tyr Ala Ser
                        610                 615                 620

Met Leu Thr Gln Ala Met Asp Tyr Asp Arg Ile Leu Ala Gly Ser Arg
        625                 630                 635                 640

Ser His Gln Ser Gly Val Ser Gly Glu Asn Asn Ser Val Arg Leu Ser
                        645                 650                 655

Ile Gln Gly Gly His Leu Gly His Asp Asn Asn Gly Ile Ala Arg
                        660                 665                 670

Gly Ala Thr Pro Glu Ser Asn Gly Ser Tyr Gly Phe Val Arg Leu Glu
                        675                 680                 685

Gly Asp Leu Leu Arg Thr Glu Val Ala Gly Met Ser Leu Thr Thr Gly
                        690                 695                 700

Val Tyr Gly Ala Ala Gly His Ser Ser Val Asp Val Lys Asp Asp Asp
        705                 710                 715                 720

Gly Ser Arg Ala Gly Thr Val Arg Asp Ala Gly Ser Leu Gly Gly
                        725                 730                 735

Tyr Leu His Leu Val His Thr Ser Ser Gly Leu Trp Ala Asp Ile Val
                        740                 745                 750

Ala Gln Gly Thr Arg His Ser Met Lys Ala Ser Ser Asp Asn Asn Asp
                        755                 760                 765

Phe Arg Ala Arg Gly Trp Gly Trp Leu Gly Ser Leu Glu Thr Gly Leu
                        770                 775                 780

Pro Phe Ser Ile Thr Asp Asn Leu Met Leu Glu Pro Gln Leu Gln Tyr
        785                 790                 795                 800

Thr Trp Gln Gly Leu Ser Leu Asp Asp Gly Gln Asp Asn Ala Gly Tyr
                        805                 810                 815
```

```
Val Lys Phe Gly His Gly Ser Ala Gln His Val Arg Ala Gly Phe Arg
            820                 825                 830

Leu Gly Ser His Asn Asp Met Asn Phe Gly Lys Gly Thr Ser Ser Arg
            835                 840                 845

Asp Thr Leu His Asp Ser Ala Lys His Ser Val Arg Glu Leu Pro Val
            850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
            885                 890                 895

Pro Ser Arg Asn Gly Thr Ser Leu Asp Leu Gln Ala Gly Leu Glu Ala
            900                 905                 910

Arg Val Arg Glu Asn Ile Thr Leu Gly Val Gln Ala Gly Tyr Ala His
            915                 920                 925

Ser Val Ser Gly Ser Ser Ala Glu Gly Tyr Asn Gly Gln Ala Thr Leu
            930                 935                 940

Asn Val Thr Phe
945

<210> SEQ ID NO 32
<211> LENGTH: 553
<212> TYPE: PRT
<213> ORGANISM: Escherichia coli

<400> SEQUENCE: 32

Ala Asp Thr Val Val Gln Ala Gly Glu Thr Val Asn Gly Gly Thr Leu
1               5                   10                  15

Thr Asn His Asp Asn Gln Ile Val Leu Gly Thr Ala Asn Gly Met Thr
            20                  25                  30

Ile Ser Thr Gly Leu Glu Tyr Gly Pro Asp Asn Glu Ala Asn Thr Gly
            35                  40                  45

Gly Gln Trp Ile Gln Asn Gly Gly Ile Ala Asn Asn Thr Thr Val Thr
    50                  55                  60

Gly Gly Gly Leu Gln Arg Val Asn Ala Gly Gly Ser Val Ser Asp Thr
65              70                  75                  80

Val Ile Ser Ala Gly Gly Gln Ser Leu Gln Gly Gln Ala Val Asn
            85                  90                  95

Thr Thr Leu Asn Gly Gly Glu Gln Trp Val His Glu Gly Gly Ile Ala
            100                 105                 110

Thr Gly Thr Val Ile Asn Glu Lys Gly Trp Gln Ala Val Lys Ser Gly
            115                 120                 125

Ala Met Ala Thr Asp Thr Val Val Asn Thr Gly Ala Glu Gly Gly Pro
            130                 135                 140

Asp Ala Glu Asn Gly Asp Thr Gly Gln Thr Val Tyr Gly Asp Ala Val
145                 150                 155                 160

Arg Thr Thr Ile Asn Lys Asn Gly Arg Gln Ile Val Ala Ala Glu Gly
            165                 170                 175

Thr Ala Asn Thr Thr Val Val Tyr Ala Gly Gly Asp Gln Thr Val His
            180                 185                 190

Gly His Ala Leu Asp Thr Thr Leu Asn Gly Gly Tyr Gln Tyr Val His
            195                 200                 205

Asn Gly Gly Thr Ala Ser Asp Thr Val Val Asn Ser Asp Gly Trp Gln
            210                 215                 220

Ile Ile Lys Glu Gly Gly Leu Ala Asp Phe Thr Thr Val Asn Gln Lys
```

```
                225                 230                 235                 240
Gly Lys Leu Gln Val Asn Ala Gly Gly Thr Ala Thr Asn Val Thr Leu
                    245                 250                 255
Thr Gln Gly Gly Ala Leu Val Thr Ser Thr Ala Thr Val Thr Gly
        260                 265                 270
Ser Asn Arg Leu Gly Asn Phe Thr Val Glu Asn Gly Asn Ala Asp Gly
            275                 280                 285
Val Val Leu Glu Ser Gly Gly Arg Leu Asp Val Leu Glu Gly His Ser
    290                 295                 300
Ala Trp Lys Thr Leu Val Asp Asp Gly Gly Thr Leu Ala Val Ser Ala
305                 310                 315                 320
Gly Gly Lys Ala Thr Asp Val Thr Met Thr Ser Gly Gly Ala Leu Ile
                325                 330                 335
Ala Asp Ser Gly Ala Thr Val Glu Gly Thr Asn Ala Ser Gly Lys Phe
            340                 345                 350
Ser Ile Asp Gly Ile Ser Gly Gln Ala Ser Gly Leu Leu Leu Glu Asn
        355                 360                 365
Gly Gly Ser Phe Thr Val Asn Ala Gly Gly Leu Ala Ser Asn Thr Thr
    370                 375                 380
Val Gly His Arg Gly Thr Leu Thr Leu Ala Ala Gly Gly Ser Leu Ser
385                 390                 395                 400
Gly Arg Thr Gln Leu Ser Lys Gly Ala Ser Met Val Leu Asn Gly Asp
                405                 410                 415
Val Val Ser Thr Gly Asp Ile Val Asn Ala Gly Glu Ile Arg Phe Asp
            420                 425                 430
Asn Gln Thr Thr Pro Asp Ala Ala Leu Ser Arg Ala Val Ala Lys Gly
        435                 440                 445
Asp Ser Pro Val Thr Phe His Lys Leu Thr Thr Ser Asn Leu Thr Gly
    450                 455                 460
Gln Gly Gly Thr Ile Asn Met Arg Val Arg Leu Asp Gly Ser Asn Ala
465                 470                 475                 480
Ser Asp Gln Leu Val Ile Asn Gly Gly Gln Ala Thr Gly Lys Thr Trp
                485                 490                 495
Leu Ala Phe Thr Asn Val Gly Asn Ser Asn Leu Gly Val Ala Thr Ser
            500                 505                 510
Gly Gln Gly Ile Arg Val Asp Ala Gln Asn Gly Ala Thr Thr Glu
        515                 520                 525
Glu Gly Ala Phe Ala Leu Ser Arg Pro Leu Gln Ala Gly Ala Phe Asn
    530                 535                 540
Tyr Thr Leu Asn Arg Asp Ser Asp Glu
545                 550

<210> SEQ ID NO 33
<211> LENGTH: 949
<212> TYPE: PRT
<213> ORGANISM: Escherichia coli

<400> SEQUENCE: 33

Met Lys Arg His Leu Asn Thr Ser Tyr Arg Leu Val Trp Asn His Ile
1               5                   10                  15
Thr Gly Thr Leu Val Val Ala Ser Glu Leu Ala Arg Ser Arg Gly Lys
                20                  25                  30
Arg Ala Gly Val Ala Val Ala Leu Ser Leu Ala Ala Val Thr Ser Val
            35                  40                  45
```

```
Pro Ala Leu Ala Ala Asp Lys Val Val Gln Ala Gly Glu Thr Val Asn
    50              55                  60

Asp Gly Thr Leu Thr Asn His Asp Asn Gln Ile Val Phe Gly Thr Ala
65              70                  75                  80

Asn Gly Met Thr Ile Ser Thr Gly Leu Glu Leu Gly Pro Asp Ser Glu
                85                  90                  95

Glu Asn Thr Gly Gly Gln Trp Ile Gln Asn Gly Gly Ile Ala Gly Asn
                100                 105                 110

Thr Thr Val Thr Thr Asn Gly Arg Gln Val Val Leu Glu Gly Gly Thr
            115                 120                 125

Ala Ser Asp Thr Val Ile Arg Asp Gly Gly Gln Ser Leu Asn Gly
    130                 135                 140

Leu Ala Val Asn Thr Thr Leu Asn Asn Arg Gly Glu Gln Trp Val His
145                 150                 155                 160

Glu Gly Gly Val Ala Thr Gly Thr Ile Ile Asn Arg Asp Gly Tyr Gln
                165                 170                 175

Ser Val Lys Ser Gly Gly Leu Ala Thr Gly Thr Ile Ile Asn Thr Gly
            180                 185                 190

Ala Glu Gly Gly Pro Asp Ser Asp Asn Ser Tyr Thr Gly Gln Lys Val
        195                 200                 205

Gln Gly Thr Ala Glu Ser Thr Thr Ile Asn Lys Asn Gly Arg Gln Ile
    210                 215                 220

Ile Leu Phe Ser Gly Leu Ala Arg Asp Thr Leu Ile Tyr Ala Gly Gly
225                 230                 235                 240

Asp Gln Ser Val His Gly Arg Ala Leu Asn Thr Thr Leu Asn Gly Gly
        245                 250                 255

Tyr Gln Tyr Val His Arg Asp Gly Leu Ala Leu Asn Thr Val Ile Asn
            260                 265                 270

Glu Gly Gly Trp Gln Val Val Lys Ala Gly Ala Ala Gly Asn Thr
        275                 280                 285

Thr Ile Asn Gln Asn Gly Glu Leu Arg Val His Ala Gly Gly Glu Ala
    290                 295                 300

Thr Ala Val Thr Gln Asn Thr Gly Gly Ala Leu Val Thr Ser Thr Ala
305                 310                 315                 320

Ala Thr Val Ile Gly Thr Asn Arg Leu Gly Asn Phe Thr Val Glu Asn
                325                 330                 335

Gly Lys Ala Asp Gly Val Val Leu Glu Ser Gly Gly Arg Leu Asp Val
            340                 345                 350

Leu Glu Ser His Ser Ala Gln Asn Thr Leu Val Asp Asp Gly Gly Thr
        355                 360                 365

Leu Ala Val Ser Ala Gly Gly Lys Ala Thr Ser Val Thr Ile Thr Ser
370                 375                 380

Gly Gly Ala Leu Ile Ala Asp Ser Gly Ala Thr Val Glu Gly Thr Asn
385                 390                 395                 400

Ala Ser Gly Lys Phe Ser Ile Asp Gly Thr Ser Gln Ala Ser Gly
            405                 410                 415

Leu Leu Leu Glu Asn Gly Gly Ser Phe Thr Val Asn Ala Gly Gly Gln
                420                 425                 430

Ala Gly Asn Thr Thr Val Gly His Arg Gly Thr Leu Thr Leu Ala Ala
            435                 440                 445

Gly Gly Ser Leu Ser Gly Arg Thr Gln Leu Ser Lys Gly Ala Ser Met
    450                 455                 460

Val Leu Asn Gly Asp Val Val Ser Thr Gly Asp Ile Val Asn Ala Gly
```

-continued

```
465                 470                 475                 480
Glu Ile Arg Phe Asp Asn Gln Thr Thr Pro Asn Ala Ala Leu Ser Arg
                485                 490                 495
Ala Val Ala Lys Ser Asn Ser Pro Val Thr Phe His Lys Leu Thr Thr
                500                 505                 510
Thr Asn Leu Thr Gly Gln Gly Thr Ile Asn Met Arg Val Arg Leu
                515                 520                 525
Asp Gly Ser Asn Ala Ser Asp Gln Leu Val Ile Asn Gly Gly Gln Ala
                530                 535                 540
Thr Gly Lys Thr Trp Leu Ala Phe Thr Asn Val Gly Asn Ser Asn Leu
545                 550                 555                 560
Gly Val Ala Thr Thr Gly Gln Gly Ile Arg Val Val Asp Ala Gln Asn
                565                 570                 575
Gly Ala Thr Thr Glu Glu Gly Ala Phe Ala Leu Ser Arg Pro Leu Gln
                580                 585                 590
Ala Gly Ala Phe Asn Tyr Thr Leu Asn Arg Asp Ser Asp Glu Asp Trp
                595                 600                 605
Tyr Leu Arg Ser Glu Asn Ala Tyr Arg Ala Glu Val Pro Leu Tyr Thr
                610                 615                 620
Ser Met Leu Thr Gln Ala Met Asp Tyr Asp Arg Ile Leu Ala Gly Ser
625                 630                 635                 640
Arg Ser His Gln Thr Gly Val Asn Gly Glu Asn Asn Ser Val Arg Leu
                645                 650                 655
Ser Ile Gln Gly Gly His Leu Gly His Asp Asn Asn Gly Gly Ile Ala
                660                 665                 670
Arg Gly Ala Thr Pro Glu Ser Ser Gly Ser Tyr Gly Phe Val Arg Leu
                675                 680                 685
Glu Gly Asp Leu Leu Arg Thr Glu Val Ala Gly Met Ser Leu Thr Thr
                690                 695                 700
Gly Val Tyr Gly Ala Ala Gly His Ser Ser Val Asp Val Lys Asp Asp
705                 710                 715                 720
Asp Gly Ser Arg Ala Gly Thr Val Arg Asp Asp Ala Gly Ser Leu Gly
                725                 730                 735
Gly Tyr Leu Asn Leu Val His Thr Ser Ser Gly Leu Trp Ala Asp Ile
                740                 745                 750
Val Ala Gln Gly Thr Arg His Ser Met Lys Ala Ser Ser Asp Asn Asn
                755                 760                 765
Asp Phe Arg Ala Arg Gly Trp Gly Trp Leu Gly Ser Leu Glu Thr Gly
                770                 775                 780
Leu Pro Phe Ser Ile Thr Asp Asn Leu Met Leu Glu Pro Gln Leu Gln
785                 790                 795                 800
Tyr Thr Trp Gln Gly Leu Ser Leu Asp Asp Gly Gln Asp Asn Ala Gly
                805                 810                 815
Tyr Val Lys Phe Gly His Gly Ser Ala Gln His Val Arg Ala Gly Phe
                820                 825                 830
Arg Leu Gly Ser His Asn Asp Met Thr Phe Gly Glu Gly Thr Ser Ser
                835                 840                 845
Arg Asp Thr Leu Arg Asp Ser Ala Lys His Ser Val Ser Glu Leu Pro
                850                 855                 860
Val Asn Trp Trp Val Gln Pro Ser Val Ile Arg Thr Phe Ser Ser Arg
865                 870                 875                 880
Gly Asp Met Ser Met Gly Thr Ala Ala Ala Gly Ser Asn Met Thr Phe
                885                 890                 895
```

```
Ser Pro Ser Arg Asn Gly Thr Ser Leu Asp Leu Gln Ala Gly Leu Glu
            900                 905                 910

Ala Arg Ile Arg Glu Asn Ile Thr Leu Gly Val Gln Ala Gly Tyr Ala
        915                 920                 925

His Ser Val Ser Gly Ser Ser Ala Glu Gly Tyr Asn Gly Gln Ala Thr
    930                 935                 940

Leu Asn Met Thr Phe
945

<210> SEQ ID NO 34
<211> LENGTH: 554
<212> TYPE: PRT
<213> ORGANISM: Escherichia coli

<400> SEQUENCE: 34

Ala Asp Lys Val Val Gln Ala Gly Glu Thr Val Asn Asp Gly Thr Leu
1               5                   10                  15

Thr Asn His Asp Asn Gln Ile Val Phe Gly Thr Ala Asn Gly Met Thr
            20                  25                  30

Ile Ser Thr Gly Leu Glu Leu Gly Pro Asp Ser Glu Glu Asn Thr Gly
        35                  40                  45

Gly Gln Trp Ile Gln Asn Gly Gly Ile Ala Gly Asn Thr Thr Val Thr
    50                  55                  60

Thr Asn Gly Arg Gln Val Val Leu Glu Gly Gly Thr Ala Ser Asp Thr
65                  70                  75                  80

Val Ile Arg Asp Gly Gly Gln Ser Leu Asn Gly Leu Ala Val Asn
                85                  90                  95

Thr Thr Leu Asn Asn Arg Gly Glu Gln Trp Val His Glu Gly Gly Val
            100                 105                 110

Ala Thr Gly Thr Ile Ile Asn Arg Asp Gly Tyr Gln Ser Val Lys Ser
        115                 120                 125

Gly Gly Leu Ala Thr Gly Thr Ile Ile Asn Thr Gly Ala Glu Gly Gly
    130                 135                 140

Pro Asp Ser Asp Asn Ser Tyr Thr Gly Gln Lys Val Gln Gly Thr Ala
145                 150                 155                 160

Glu Ser Thr Thr Ile Asn Lys Asn Gly Arg Gln Ile Ile Leu Phe Ser
                165                 170                 175

Gly Leu Ala Arg Asp Thr Leu Ile Tyr Ala Gly Gly Asp Gln Ser Val
            180                 185                 190

His Gly Arg Ala Leu Asn Thr Thr Leu Asn Gly Gly Tyr Gln Tyr Val
        195                 200                 205

His Arg Asp Gly Leu Ala Leu Asn Thr Val Ile Asn Glu Gly Gly Trp
    210                 215                 220

Gln Val Val Lys Ala Gly Gly Ala Ala Gly Asn Thr Thr Ile Asn Gln
225                 230                 235                 240

Asn Gly Glu Leu Arg Val His Ala Gly Gly Glu Ala Thr Ala Val Thr
                245                 250                 255

Gln Asn Thr Gly Gly Ala Leu Val Thr Ser Thr Ala Ala Thr Val Ile
            260                 265                 270

Gly Thr Asn Arg Leu Gly Asn Phe Thr Val Glu Asn Gly Lys Ala Asp
        275                 280                 285

Gly Val Val Leu Glu Ser Gly Gly Arg Leu Asp Val Leu Glu Ser His
    290                 295                 300

Ser Ala Gln Asn Thr Leu Val Asp Asp Gly Gly Thr Leu Ala Val Ser
```

```
            305                 310                 315                 320
Ala Gly Gly Lys Ala Thr Ser Val Thr Ile Thr Ser Gly Gly Ala Leu
                325                 330                 335

Ile Ala Asp Ser Gly Ala Thr Val Glu Gly Thr Asn Ala Ser Gly Lys
                340                 345                 350

Phe Ser Ile Asp Gly Thr Ser Gly Gln Ala Ser Gly Leu Leu Leu Glu
                355                 360                 365

Asn Gly Gly Ser Phe Thr Val Asn Ala Gly Gly Gln Ala Gly Asn Thr
                370                 375                 380

Thr Val Gly His Arg Gly Thr Leu Thr Leu Ala Ala Gly Gly Ser Leu
385                 390                 395                 400

Ser Gly Arg Thr Gln Leu Ser Lys Gly Ala Ser Met Val Leu Asn Gly
                405                 410                 415

Asp Val Val Ser Thr Gly Asp Ile Val Asn Ala Gly Glu Ile Arg Phe
                420                 425                 430

Asp Asn Gln Thr Thr Pro Asn Ala Ala Leu Ser Arg Ala Val Ala Lys
                435                 440                 445

Ser Asn Ser Pro Val Thr Phe His Lys Leu Thr Thr Thr Asn Leu Thr
                450                 455                 460

Gly Gln Gly Gly Thr Ile Asn Met Arg Val Arg Leu Asp Gly Ser Asn
465                 470                 475                 480

Ala Ser Asp Gln Leu Val Ile Asn Gly Gly Gln Ala Thr Gly Lys Thr
                485                 490                 495

Trp Leu Ala Phe Thr Asn Val Gly Asn Ser Asn Leu Gly Val Ala Thr
                500                 505                 510

Thr Gly Gln Gly Ile Arg Val Val Asp Ala Gln Asn Gly Ala Thr Thr
                515                 520                 525

Glu Glu Gly Ala Phe Ala Leu Ser Arg Pro Leu Gln Ala Gly Ala Phe
                530                 535                 540

Asn Tyr Thr Leu Asn Arg Asp Ser Asp Glu
545                 550

<210> SEQ ID NO 35
<211> LENGTH: 989
<212> TYPE: PRT
<213> ORGANISM: Escherichia coli

<400> SEQUENCE: 35

Met Asn Lys Val Tyr Asn Thr Val Trp Asn Glu Ser Thr Gly Thr Trp
1               5                   10                  15

Val Val Thr Ser Glu Leu Thr Arg Lys Gly Gly Leu Arg Pro Arg Gln
                20                  25                  30

Ile Lys Arg Thr Val Leu Ala Gly Leu Ile Ala Gly Leu Leu Met Pro
                35                  40                  45

Ser Met Pro Ala Leu Ala Ala Ala Tyr Asp Asn Gln Thr Ile Gly Arg
                50                  55                  60

Gly Glu Thr Ser Lys Ser Met His Leu Ser Ala Gly Asp Thr Ala Lys
65                  70                  75                  80

Asn Thr Thr Ile Asn Ser Gly Gly Lys Gln Tyr Val Ser Ser Gly Gly
                85                  90                  95

Ser Ala Thr Ser Thr Thr Ile Asn Ile Gly Gly Val Gln His Val Ser
                100                 105                 110

Ser Gly Gly Ser Ala Thr Ser Ser Thr Ile Asn Ser Gly Gly His Gln
                115                 120                 125
```

His Val Ser Ser Gly Gly Ser Ala Thr Asn Thr Thr Val Asn Asn Gly
    130                 135                 140

Gly Arg Gln Thr Val Phe Ser Gly Gly Ser Ala Met Gly Thr Ile Ile
145                 150                 155                 160

Asn Ser Gly Gly Asp Gln Tyr Val Ile Ser Gly Gly Ser Ala Thr Ser
                165                 170                 175

Ala Ser Val Thr Ser Gly Ala Arg Gln Phe Val Ser Ser Gly Gly Ile
            180                 185                 190

Val Lys Ala Thr Ser Val Asn Ser Gly Gly Arg Gln Tyr Val Arg Asp
        195                 200                 205

Gly Gly Ser Ala Thr Asp Thr Val Leu Asn Asn Thr Gly Arg Gln Phe
    210                 215                 220

Val Ser Ser Gly Gly Ser Ala Ala Lys Thr Thr Ile Asn Ser Gly Gly
225                 230                 235                 240

Gly Met Tyr Leu Tyr Gly Gly Ser Ala Thr Gly Thr Ser Ile Tyr Asn
                245                 250                 255

Gly Gly Arg Gln Tyr Val Ser Ser Gly Gly Ser Ala Thr Asn Thr Thr
            260                 265                 270

Val Tyr Ser Gly Gly Arg Gln His Val Tyr Ile Asp Gly Asn Val Thr
        275                 280                 285

Glu Thr Thr Ile Thr Ser Gly Gly Met Leu Gln Val Glu Ala Gly Gly
    290                 295                 300

Ser Ala Ser Lys Val Ile Gln Asn Ser Gly Gly Ala Val Ile Thr Asn
305                 310                 315                 320

Thr Ser Ala Ala Val Ser Gly Thr Asn Asp Asn Gly Ser Phe Ser Ile
                325                 330                 335

Ala Gly Gly Ser Ala Val Asn Met Leu Leu Glu Asn Gly Gly Tyr Leu
            340                 345                 350

Thr Val Phe Asp Gly His Gln Ala Ser Asp Thr Met Val Gly Ser Asp
        355                 360                 365

Gly Thr Leu Asp Val Arg Ser Gly Gly Val Leu Tyr Gly Thr Thr Thr
    370                 375                 380

Leu Thr Asp Lys Gly Ala Leu Val Gly Asp Val Val Thr Asn Glu Gly
385                 390                 395                 400

Asn Leu Tyr Tyr Leu Asn Asn Ser Thr Ala Thr Phe Thr Gly Thr Leu
                405                 410                 415

Thr Gly Thr Gly Thr Leu Thr Gln Glu Gly Gly Asn Thr Arg Phe Ser
            420                 425                 430

Gly Leu Leu Ser Gln Asp Gly Gly Ile Phe Leu Gln Ser Gly Gly Ala
        435                 440                 445

Met Thr Met Asp Ala Leu Gln Ala Lys Ala Asn Val Thr Thr Gln Ser
    450                 455                 460

Gly Thr Thr Leu Thr Leu Asp Asn Gly Thr Ile Leu Thr Gly Asn Val
465                 470                 475                 480

Ala Gly Asp Ser Thr Gly Ala Gly Asp Met Ala Val Lys Gly Ala Ser
                485                 490                 495

Val Trp His Leu Asp Gly Asp Ser Thr Val Gly Ala Leu Thr Leu Asp
            500                 505                 510

Asn Gly Thr Val Asp Phe Arg Pro Ser Thr Thr Arg Met Thr Pro
        515                 520                 525

Ala Phe Gln Ala Val Ser Leu Ala Leu Gly Ser Leu Ser Gly Ser Gly
    530                 535                 540

Thr Phe Gln Met Asn Thr Asp Ile Ala Ser His Thr Gly Asp Met Leu

-continued

```
              545                 550                 555                 560
Asn Val Ala Gly Asn Ala Ser Gly Asn Phe Val Leu Asp Ile Lys Asn
              565                 570                 575
Thr Gly Leu Glu Pro Val Ser Ala Gly Ala Pro Leu Gln Val Val Gln
              580                 585                 590
Thr Gly Gly Gly Asp Ala Ala Phe Thr Leu Lys Gly Lys Val Asp
              595                 600                 605
Ala Gly Thr Trp Glu Tyr Gly Leu Ser Lys Glu Asn Thr Asn Trp Tyr
              610                 615                 620
Leu Lys Ala Asp Thr Pro Pro Val Thr Pro Thr Asn Pro Asp
625                 630                 635                 640
Ala Asp Asn Pro Asp Ala Gly Asn Pro Asp Ala Gly Asn Pro Asp Ala
                  645                 650                 655
Gly Asn Pro Asp Ala Gly Asn Pro Asp Ala Gly Lys Pro Gly Thr Gly
                  660                 665                 670
Lys Pro Asp Ala Gly Thr Ser Ser Pro Val Arg Arg Thr Thr Lys
                  675                 680                 685
Ser Val Asp Ala Val Leu Gly Met Ala Thr Ala Pro Ala Tyr Val Phe
              690                 695                 700
Asn Ser Glu Leu Asp Asn Leu Arg Phe Arg His Gly Asp Val Met Gln
705                 710                 715                 720
Asn Thr Arg Ala Pro Gly Gly Val Trp Gly Arg Tyr Thr Gly Ser Asp
                  725                 730                 735
Asn Arg Ile Ser Gly Gly Ala Ser Ser Gly Tyr Thr Leu Thr Gln Asn
                  740                 745                 750
Gly Phe Glu Thr Gly Ala Asp Met Val Phe Asp Leu Ser Asp Ser Ser
              755                 760                 765
Leu Ala Val Gly Thr Phe Phe Ser Tyr Ser Asp Asn Ser Ile Lys His
              770                 775                 780
Ala Arg Gly Gly Lys Ser Asn Val Asp Ser Ser Gly Gly Leu Tyr
785                 790                 795                 800
Ala Thr Trp Phe Asp Asn Asp Gly Tyr Tyr Val Asp Gly Val Leu Lys
                  805                 810                 815
Tyr Asn Arg Phe Asn Asn Glu Leu Arg Thr Trp Met Ser Asp Gly Thr
                  820                 825                 830
Ala Val Lys Gly Asp Tyr Ser Gln Asn Gly Phe Gly Ser Leu Glu
                  835                 840                 845
Ala Gly Arg Thr Phe Ser Leu Asn Glu Asn Ala Trp Ala Gln Pro Tyr
              850                 855                 860
Val Arg Thr Thr Ala Phe Arg Ala Asp Lys Lys Glu Ile Arg Leu Asn
865                 870                 875                 880
Asn Gly Met Lys Ala Ser Ile Gly Ala Thr Lys Ser Leu Gln Ala Glu
                  885                 890                 895
Ala Gly Leu Lys Leu Gly Met Thr Leu Asp Val Ala Gly Lys Glu Val
                  900                 905                 910
Lys Pro Tyr Leu Ser Ala Ala Val Ser His Glu Phe Ser Asp Asn Asn
              915                 920                 925
Lys Val Arg Ile Asn Asp Thr Tyr Asp Phe Arg Asn Asp Ile Ser Gly
              930                 935                 940
Thr Thr Gly Lys Tyr Gly Leu Gly Val Asn Ala Gln Leu Thr Pro Asn
945                 950                 955                 960
Ala Gly Val Trp Ala Glu Ala Arg Tyr Glu Asn Gly Lys Gln Thr Glu
                  965                 970                 975
```

```
Ser Pro Ile Thr Gly Gly Val Gly Phe Arg Ile Asn Phe
            980                 985
```

<210> SEQ ID NO 36
<211> LENGTH: 573
<212> TYPE: PRT
<213> ORGANISM: Escherichia coli

<400> SEQUENCE: 36

```
Tyr Asp Asn Gln Thr Ile Gly Arg Gly Glu Thr Ser Lys Ser Met His
1               5                   10                  15

Leu Ser Ala Gly Asp Thr Ala Lys Asn Thr Thr Ile Asn Ser Gly Gly
            20                  25                  30

Lys Gln Tyr Val Ser Ser Gly Gly Ser Ala Thr Ser Thr Thr Ile Asn
        35                  40                  45

Ile Gly Gly Val Gln His Val Ser Ser Gly Gly Ser Ala Thr Ser Ser
    50                  55                  60

Thr Ile Asn Ser Gly Gly His Gln His Val Ser Ser Gly Gly Ser Ala
65                  70                  75                  80

Thr Asn Thr Thr Val Asn Asn Gly Gly Arg Gln Thr Val Phe Ser Gly
                85                  90                  95

Gly Ser Ala Met Gly Thr Ile Ile Asn Ser Gly Gly Asp Gln Tyr Val
            100                 105                 110

Ile Ser Gly Gly Ser Ala Thr Ser Ala Ser Val Thr Ser Gly Ala Arg
        115                 120                 125

Gln Phe Val Ser Ser Gly Gly Ile Val Lys Ala Thr Ser Val Asn Ser
    130                 135                 140

Gly Gly Arg Gln Tyr Val Arg Asp Gly Gly Ser Ala Thr Asp Thr Val
145                 150                 155                 160

Leu Asn Asn Thr Gly Arg Gln Phe Val Ser Ser Gly Ser Ala Ala
                165                 170                 175

Lys Thr Thr Ile Asn Ser Gly Gly Gly Met Tyr Leu Tyr Gly Gly Ser
            180                 185                 190

Ala Thr Gly Thr Ser Ile Tyr Asn Gly Gly Arg Gln Tyr Val Ser Ser
        195                 200                 205

Gly Gly Ser Ala Thr Asn Thr Thr Val Tyr Ser Gly Gly Arg Gln His
    210                 215                 220

Val Tyr Ile Asp Gly Asn Val Thr Glu Thr Thr Ile Thr Ser Gly Gly
225                 230                 235                 240

Met Leu Gln Val Glu Ala Gly Gly Ser Ala Ser Lys Val Ile Gln Asn
                245                 250                 255

Ser Gly Gly Ala Val Ile Thr Asn Thr Ser Ala Ala Val Ser Gly Thr
            260                 265                 270

Asn Asp Asn Gly Ser Phe Ser Ile Ala Gly Gly Ser Ala Val Asn Met
        275                 280                 285

Leu Leu Glu Asn Gly Gly Tyr Leu Thr Val Phe Asp Gly His Gln Ala
    290                 295                 300

Ser Asp Thr Met Val Gly Ser Asp Gly Thr Leu Asp Val Arg Ser Gly
305                 310                 315                 320

Gly Val Leu Tyr Gly Thr Thr Leu Thr Asp Lys Gly Ala Leu Val
                325                 330                 335

Gly Asp Val Val Thr Asn Glu Gly Asn Leu Tyr Tyr Leu Asn Asn Ser
            340                 345                 350

Thr Ala Thr Phe Thr Gly Thr Leu Thr Gly Thr Gly Thr Leu Thr Gln
```

```
                355                 360                 365
Glu Gly Gly Asn Thr Arg Phe Ser Gly Leu Leu Ser Gln Asp Gly Gly
            370                 375                 380

Ile Phe Leu Gln Ser Gly Gly Ala Met Thr Met Asp Ala Leu Gln Ala
385                 390                 395                 400

Lys Ala Asn Val Thr Thr Gln Ser Gly Thr Thr Leu Thr Leu Asp Asn
                405                 410                 415

Gly Thr Ile Leu Thr Gly Asn Val Ala Gly Asp Ser Thr Gly Ala Gly
            420                 425                 430

Asp Met Ala Val Lys Gly Ala Ser Val Trp His Leu Asp Gly Asp Ser
            435                 440                 445

Thr Val Gly Ala Leu Thr Leu Asp Asn Gly Thr Val Asp Phe Arg Pro
        450                 455                 460

Ser Thr Thr Thr Arg Met Thr Pro Ala Phe Gln Ala Val Ser Leu Ala
465                 470                 475                 480

Leu Gly Ser Leu Ser Gly Ser Gly Thr Phe Gln Met Asn Thr Asp Ile
                485                 490                 495

Ala Ser His Thr Gly Asp Met Leu Asn Val Ala Gly Asn Ala Ser Gly
            500                 505                 510

Asn Phe Val Leu Asp Ile Lys Asn Thr Gly Leu Glu Pro Val Ser Ala
            515                 520                 525

Gly Ala Pro Leu Gln Val Val Gln Thr Gly Gly Asp Ala Ala Phe
        530                 535                 540

Thr Leu Lys Gly Gly Lys Val Asp Ala Gly Thr Trp Glu Tyr Gly Leu
545                 550                 555                 560

Ser Lys Glu Asn Thr Asn Trp Tyr Leu Lys Ala Asp Thr
                565                 570

<210> SEQ ID NO 37
<211> LENGTH: 41
<212> TYPE: DNA
<213> ORGANISM: Artificial Sequence
<220> FEATURE:
<223> OTHER INFORMATION: mVh1_For primer

<400> SEQUENCE: 37
accgccaccg gtgtccactc ccaggtccaa ctgcagcagc c                    41

<210> SEQ ID NO 38
<211> LENGTH: 56
<212> TYPE: DNA
<213> ORGANISM: Artificial Sequence
<220> FEATURE:
<223> OTHER INFORMATION: mG2b_Ch1_Rev primer

<400> SEQUENCE: 38
gggccctcta gattagtgat ggtgatggtg atgaagtttt ttgtccaccg tggtgc     56

<210> SEQ ID NO 39
<211> LENGTH: 45
<212> TYPE: DNA
<213> ORGANISM: Artificial Sequence
<220> FEATURE:
<223> OTHER INFORMATION: mVk6_For primer

<400> SEQUENCE: 39
accgccaccg gtgtccactc cagtattgtg atgacccaga ctccc                45

<210> SEQ ID NO 40
```

<211> LENGTH: 40
<212> TYPE: DNA
<213> ORGANISM: Artificial Sequence
<220> FEATURE:
<223> OTHER INFORMATION: mKappa_Rev primer

<400> SEQUENCE: 40
gggccctcta gattaacact cattcctgtt gaagctcttg          40

<210> SEQ ID NO 41
<211> LENGTH: 1091
<212> TYPE: PRT
<213> ORGANISM: Escherichia coli

<400> SEQUENCE: 41

```
Met Gln Thr His Arg His Glu Ile Gln Gly Thr Thr Glu Pro His Val
1               5                   10                  15

Arg Asn Phe His Gln Pro Asp Leu Arg His Cys Asn Pro Ser Pro Ala
            20                  25                  30

Gly Ile His Ile Cys Gly Tyr Arg Leu Phe Ile His Pro His Ser Asp
        35                  40                  45

Lys Glu Met Leu Met Lys Arg His Leu Asn Thr Ser Tyr Arg Leu Val
50                  55                  60

Trp Asn His Ile Thr Gly Ala Phe Val Val Ala Ser Glu Leu Ala Arg
65                  70                  75                  80

Ala Arg Gly Lys Arg Ala Gly Val Ala Val Ala Leu Ser Leu Ala Ala
                85                  90                  95

Ala Thr Ser Leu Pro Ala Leu Ala Ala Asp Ser Val Val Pro Ala Gly
            100                 105                 110

Glu Thr Val Asn Gly Gly Thr Leu Ile Asn His Asp Arg Gln Phe Val
        115                 120                 125

Ser Gly Thr Ala Asp Gly Met Thr Val Ser Thr Gly Leu Glu Leu Gly
130                 135                 140

Ala Asp Ser Asp Asn Asn Thr Gly Gly Gln Gln Ile Ala Arg Gly Gly
145                 150                 155                 160

Thr Ala Arg Asn Thr Arg Val Thr Ala Asn Gly Leu Gln Asp Val Met
                165                 170                 175

Ala Gly Gly Ser Thr Ser Asp Thr Val Ile Ser Thr Gly Gly Gln
            180                 185                 190

Asn Leu Arg Gly Lys Ala Ser Gly Thr Val Leu Asn Gly Gly Asp Gln
        195                 200                 205

Trp Ile His Ala Gly Gly Arg Ala Ser Gly Thr Val Ile Asn Gln Asp
210                 215                 220

Gly Tyr Gln Thr Ile Lys His Gly Gly Leu Val Thr Gly Thr Ile Val
225                 230                 235                 240

Asn Thr Gly Ala Glu Gly Gly Pro Asp Ser Glu Asn Val Ser Thr Gly
                245                 250                 255

Gln Met Val Gly Gly Ile Ala Glu Ser Thr Thr Ile Asn Lys Asn Gly
            260                 265                 270

Arg Gln Val Ile Trp Ser Ser Gly Ile Ala Arg Asp Thr Leu Ile Tyr
        275                 280                 285

Thr Gly Gly Asp Gln Thr Val His Gly Glu Ala His Asn Thr Arg Leu
290                 295                 300

Glu Gly Gly Asn Gln Tyr Val His Lys Tyr Gly Leu Ala Leu Asn Thr
305                 310                 315                 320

Val Ile Asn Glu Gly Gly Trp Gln Val Val Lys Ala Gly Gly Thr Ala
```

```
                    325                 330                 335
Gly Asn Thr Thr Ile Asn Gln Asn Gly Glu Leu Arg Val His Ala Gly
                340                 345                 350
Gly Glu Ala Ser Asp Val Thr Gln Asn Thr Gly Gly Ala Leu Val Thr
                355                 360                 365
Ser Thr Ala Ala Thr Val Thr Gly Thr Asn Arg Leu Gly Ala Phe Ser
            370                 375                 380
Val Val Glu Gly Lys Ala Asp Asn Val Val Leu Glu Asn Gly Gly Arg
385                 390                 395                 400
Leu Asp Val Leu Ser Gly His Thr Ala Thr Arg Thr Leu Val Asp Asp
                405                 410                 415
Gly Gly Thr Leu Asp Val Arg Asn Gly Gly Thr Ala Thr Ala Val Ser
                420                 425                 430
Met Gly Asn Gly Val Leu Leu Ala Asp Ser Gly Ala Ala Val Ser
                435                 440                 445
Gly Thr Arg Ser Asp Gly Thr Ala Phe Arg Ile Gly Gly Gln Ala
            450                 455                 460
Asp Ala Leu Met Leu Glu Lys Gly Ser Ser Phe Thr Leu Asn Ala Gly
465                 470                 475                 480
Asp Thr Ala Thr Asp Thr Thr Val Asn Gly Leu Phe Thr Ala Arg
                485                 490                 495
Gly Gly Ser Leu Ala Gly Thr Thr Thr Leu Asn Asn Gly Ala Thr Phe
                500                 505                 510
Thr Leu Ala Gly Lys Thr Val Asn Asn Asp Thr Leu Thr Ile Arg Glu
                515                 520                 525
Gly Asp Ala Leu Leu Gln Gly Gly Ala Leu Thr Gly Asn Gly Arg Val
                530                 535                 540
Glu Lys Ser Gly Ser Gly Thr Leu Thr Val Ser Asn Thr Thr Leu Thr
545                 550                 555                 560
Gln Lys Ala Val Asn Leu Asn Glu Gly Thr Leu Thr Leu Asn Asp Ser
                565                 570                 575
Thr Val Thr Thr Asp Ile Ile Ala His Arg Gly Thr Ala Leu Lys Leu
                580                 585                 590
Thr Gly Ser Thr Val Leu Asn Gly Ala Ile Asp Pro Thr Asn Val Thr
            595                 600                 605
Leu Thr Ser Gly Ala Thr Trp Asn Ile Pro Asp Asn Ala Thr Val Gln
            610                 615                 620
Ser Val Val Asp Asp Leu Ser His Ala Gly Gln Ile His Phe Thr Ser
625                 630                 635                 640
Ala Arg Thr Gly Lys Phe Val Pro Thr Thr Leu Gln Val Lys Asn Leu
                645                 650                 655
Asn Gly Gln Asn Gly Thr Ile Ser Leu Arg Val Arg Pro Asp Met Ala
                660                 665                 670
Gln Asn Asn Ala Asp Arg Leu Val Ile Asp Gly Gly Arg Ala Thr Gly
                675                 680                 685
Lys Thr Ile Leu Asn Leu Val Asn Ala Gly Asn Ser Gly Thr Gly Leu
            690                 695                 700
Ala Thr Thr Gly Lys Gly Ile Gln Val Val Glu Ala Ile Asn Gly Ala
705                 710                 715                 720
Thr Thr Glu Glu Gly Ala Phe Val Gln Gly Asn Met Leu Gln Ala Gly
                725                 730                 735
Ala Phe Asn Tyr Thr Leu Asn Arg Asp Ser Asp Glu Ser Trp Tyr Leu
                740                 745                 750
```

Arg Ser Glu Glu Arg Tyr Arg Ala Glu Val Pro Leu Tyr Ala Ser Met
   755                 760                 765

Leu Thr Gln Ala Met Asp Tyr Asp Arg Ile Leu Ala Gly Ser Arg Ser
   770                 775                 780

His Gln Thr Gly Val Asn Gly Glu Asn Ser Val Arg Leu Ser Ile
785                 790                 795                 800

Gln Gly Gly His Leu Gly His Asp Asn Gly Gly Ile Ala Arg Gly
                805                 810                 815

Ala Thr Pro Glu Ser Ser Gly Ser Tyr Gly Phe Val Arg Leu Glu Gly
            820                 825                 830

Asp Leu Leu Arg Thr Glu Val Ala Gly Met Ser Leu Thr Thr Gly Val
                835                 840                 845

Tyr Gly Ala Ala Gly His Ser Ser Val Asp Val Lys Asp Asp Asp Gly
            850                 855                 860

Ser Arg Ala Gly Thr Val Arg Asp Asp Ala Gly Ser Leu Gly Gly Tyr
865                 870                 875                 880

Met Asn Leu Thr His Thr Ser Ser Gly Leu Trp Ala Asp Ile Val Ala
                885                 890                 895

Gln Gly Thr Arg His Ser Met Lys Ala Ser Ser Asp Asn Asn Asp Phe
            900                 905                 910

Arg Ala Arg Gly Arg Gly Trp Leu Gly Ser Leu Glu Thr Gly Leu Pro
        915                 920                 925

Phe Ser Ile Thr Asp Asn Leu Met Leu Glu Pro Arg Leu Gln Tyr Thr
   930                 935                 940

Trp Gln Gly Leu Ser Leu Asp Asp Gly Lys Asp Asn Ala Gly Tyr Val
945                 950                 955                 960

Lys Phe Gly His Gly Ser Ala Gln His Val Arg Ala Gly Phe Arg Leu
                965                 970                 975

Gly Ser His Asn Asp Met Thr Phe Gly Glu Gly Thr Ser Ser Arg Ala
            980                 985                 990

Pro Leu Arg Asp Ser Ala Lys His Ser Val Arg Glu Leu Pro Val Asn
        995                 1000                1005

Trp Trp Val Gln Pro Ser Val Ile Arg Thr Phe Ser Ser Arg Gly
   1010                1015                1020

Asp Met Arg Val Gly Thr Ser Thr Ala Gly Ser Gly Met Thr Phe
   1025                1030                1035

Ser Pro Ser Gln Asn Gly Thr Ser Leu Asp Leu Gln Ala Gly Leu
   1040                1045                1050

Glu Ala Arg Val Arg Glu Asn Ile Thr Leu Gly Val Gln Ala Gly
   1055                1060                1065

Tyr Ala His Ser Ile Asn Gly Ser Ser Ala Glu Gly Tyr Asn Ser
   1070                1075                1080

Gln Ala Thr Leu Asn Val Thr Phe
   1085                1090

<210> SEQ ID NO 42
<211> LENGTH: 652
<212> TYPE: PRT
<213> ORGANISM: Escherichia coli

<400> SEQUENCE: 42

Ala Asp Ser Val Val Pro Ala Gly Glu Thr Val Asn Gly Gly Thr Leu
1               5                   10                  15

Ile Asn His Asp Arg Gln Phe Val Ser Gly Thr Ala Asp Gly Met Thr

-continued

```
                20                  25                  30
Val Ser Thr Gly Leu Glu Leu Gly Ala Asp Ser Asp Asn Asn Thr Gly
             35                  40                  45
Gly Gln Gln Ile Ala Arg Gly Gly Thr Ala Arg Asn Thr Arg Val Thr
 50                  55                  60
Ala Asn Gly Leu Gln Asp Val Met Ala Gly Ser Thr Ser Asp Thr
 65                  70                  75                  80
Val Ile Ser Thr Gly Gly Gln Asn Leu Arg Gly Lys Ala Ser Gly
                 85                  90                  95
Thr Val Leu Asn Gly Gly Asp Gln Trp Ile His Ala Gly Gly Arg Ala
                100                 105                 110
Ser Gly Thr Val Ile Asn Gln Asp Gly Tyr Gln Thr Ile Lys His Gly
            115                 120                 125
Gly Leu Val Thr Gly Thr Ile Val Asn Thr Gly Ala Glu Gly Gly Pro
            130                 135                 140
Asp Ser Glu Asn Val Ser Thr Gly Gln Met Val Gly Gly Ile Ala Glu
145                 150                 155                 160
Ser Thr Thr Ile Asn Lys Asn Gly Arg Gln Val Ile Trp Ser Ser Gly
                165                 170                 175
Ile Ala Arg Asp Thr Leu Ile Tyr Thr Gly Gly Asp Gln Thr Val His
            180                 185                 190
Gly Glu Ala His Asn Thr Arg Leu Glu Gly Gly Asn Gln Tyr Val His
            195                 200                 205
Lys Tyr Gly Leu Ala Leu Asn Thr Val Ile Asn Glu Gly Gly Trp Gln
            210                 215                 220
Val Val Lys Ala Gly Gly Thr Ala Gly Asn Thr Thr Ile Asn Gln Asn
225                 230                 235                 240
Gly Glu Leu Arg Val His Ala Gly Gly Glu Ala Ser Asp Val Thr Gln
                245                 250                 255
Asn Thr Gly Gly Ala Leu Val Thr Ser Thr Ala Ala Thr Val Thr Gly
            260                 265                 270
Thr Asn Arg Leu Gly Ala Phe Ser Val Val Glu Gly Lys Ala Asp Asn
            275                 280                 285
Val Val Leu Glu Asn Gly Gly Arg Leu Asp Val Leu Ser Gly His Thr
            290                 295                 300
Ala Thr Arg Thr Leu Val Asp Asp Gly Gly Thr Leu Asp Val Arg Asn
305                 310                 315                 320
Gly Gly Thr Ala Thr Ala Val Ser Met Gly Asn Gly Val Leu Leu
            325                 330                 335
Ala Asp Ser Gly Ala Ala Val Ser Gly Thr Arg Ser Asp Gly Thr Ala
            340                 345                 350
Phe Arg Ile Gly Gly Gln Ala Asp Ala Leu Met Leu Glu Lys Gly
            355                 360                 365
Ser Ser Phe Thr Leu Asn Ala Gly Asp Thr Ala Thr Asp Thr Thr Val
            370                 375                 380
Asn Gly Gly Leu Phe Thr Ala Arg Gly Gly Ser Leu Ala Gly Thr Thr
385                 390                 395                 400
Thr Leu Asn Asn Gly Ala Thr Phe Thr Leu Ala Gly Lys Thr Val Asn
                405                 410                 415
Asn Asp Thr Leu Thr Ile Arg Glu Gly Asp Ala Leu Leu Gln Gly Gly
            420                 425                 430
Ala Leu Thr Gly Asn Gly Arg Val Glu Lys Ser Gly Ser Gly Thr Leu
            435                 440                 445
```

-continued

```
Thr Val Ser Asn Thr Thr Leu Thr Gln Lys Ala Val Asn Leu Asn Glu
    450                 455                 460

Gly Thr Leu Thr Leu Asn Asp Ser Thr Val Thr Asp Ile Ile Ala
465                 470                 475                 480

His Arg Gly Thr Ala Leu Lys Leu Thr Gly Ser Thr Val Leu Asn Gly
                    485                 490                 495

Ala Ile Asp Pro Thr Asn Val Thr Leu Thr Ser Gly Ala Thr Trp Asn
                500                 505                 510

Ile Pro Asp Asn Ala Thr Val Gln Ser Val Val Asp Leu Ser His
            515                 520                 525

Ala Gly Gln Ile His Phe Thr Ser Ala Arg Thr Gly Lys Phe Val Pro
    530                 535                 540

Thr Thr Leu Gln Val Lys Asn Leu Asn Gly Gln Asn Gly Thr Ile Ser
545                 550                 555                 560

Leu Arg Val Arg Pro Asp Met Ala Gln Asn Asn Ala Asp Arg Leu Val
                565                 570                 575

Ile Asp Gly Gly Arg Ala Thr Gly Lys Thr Ile Leu Asn Leu Val Asn
            580                 585                 590

Ala Gly Asn Ser Gly Thr Gly Leu Ala Thr Thr Gly Lys Gly Ile Gln
    595                 600                 605

Val Val Glu Ala Ile Asn Gly Ala Thr Thr Glu Glu Gly Ala Phe Val
610                 615                 620

Gln Gly Asn Met Leu Gln Ala Gly Ala Phe Asn Tyr Thr Leu Asn Arg
625                 630                 635                 640

Asp Ser Asp Glu Ser Trp Tyr Leu Arg Ser Glu Glu
                645                 650

<210> SEQ ID NO 43
<211> LENGTH: 776
<212> TYPE: PRT
<213> ORGANISM: Escherichia coli

<400> SEQUENCE: 43

Met Lys Leu Val Thr Arg Met Glu Asn Phe Phe Met Lys Asn Ser Lys
1               5                   10                  15

Val Phe Tyr Arg Ser Ala Leu Ala Thr Ala Ile Val Met Ala Leu Ser
            20                  25                  30

Ala Pro Ala Phe Ala Thr Asp Ser Thr Val Ser Thr Asp Pro Val Thr
        35                  40                  45

Leu Asn Thr Glu Lys Thr Thr Leu Asp Gln Asp Val Val Ile Asn Gly
    50                  55                  60

Asp Asn Lys Ile Thr Ala Val Thr Ile Glu Thr Ser Asp Ser Asp Lys
65                  70                  75                  80

Asp Leu Asn Val Thr Phe Gly Gly His Asp Ile Thr Ala Ala Ser Thr
                85                  90                  95

Val Asn Gln Asp Phe Val Glu Gly Val Lys Val Ser Gly Asn Lys Asn
            100                 105                 110

Val Val Ile Asn Ala Thr Asp Ser Thr Ile Thr Ala Gln Gly Glu Gly
        115                 120                 125

Thr Tyr Val Arg Thr Ala Met Val Ile Asp Ser Thr Gly Asp Val Val
    130                 135                 140

Val Asn Gly Gly Asn Phe Val Ala Lys Asn Glu Lys Gly Ser Ala Thr
145                 150                 155                 160

Gly Ile Ser Leu Glu Ala Thr Thr Gly Asn Asn Leu Thr Leu Asn Gly
```

```
                    165                 170                 175
Thr Thr Ile Asn Ala Gln Gly Asn Lys Ser Tyr Ser Asn Gly Ser Thr
                180                 185                 190

Ala Ile Phe Ala Gln Lys Gly Asn Leu Leu Gln Gly Phe Asp Gly Asp
            195                 200                 205

Ala Thr Asp Asn Ile Thr Leu Ala Asp Ser Asn Ile Ile Asn Gly Gly
        210                 215                 220

Ile Glu Thr Ile Val Thr Ala Gly Asn Lys Thr Gly Ile His Thr Val
225                 230                 235                 240

Asn Leu Asn Ile Lys Asp Gly Ser Val Ile Gly Ala Ala Asn Asn Lys
                245                 250                 255

Gln Thr Ile Tyr Ala Ser Ala Ser Ala Gln Gly Ala Gly Ser Ala Thr
            260                 265                 270

Gln Asn Leu Asn Leu Ser Val Ala Asp Ser Thr Ile Tyr Ser Asp Val
        275                 280                 285

Leu Ala Leu Ser Glu Ser Glu Asn Ser Ala Ser Thr Thr Thr Asn Val
    290                 295                 300

Asn Met Asn Val Ala Arg Ser Tyr Trp Glu Gly Asn Ala Tyr Thr Phe
305                 310                 315                 320

Asn Ser Gly Asp Lys Ala Gly Ser Asp Leu Asp Ile Asn Leu Ser Asp
                325                 330                 335

Ser Ser Val Trp Lys Gly Lys Val Ser Gly Ala Gly Asp Ala Ser Val
            340                 345                 350

Ser Leu Gln Asn Gly Ser Val Trp Asn Val Thr Gly Ser Ser Thr Val
        355                 360                 365

Asp Ala Leu Ala Val Lys Asp Ser Thr Val Asn Ile Thr Lys Ala Thr
    370                 375                 380

Val Asn Thr Gly Thr Phe Ala Ser Gln Asn Gly Thr Leu Ile Val Asp
385                 390                 395                 400

Ala Ser Ser Glu Asn Thr Leu Asp Ile Ser Gly Lys Ala Ser Gly Asp
                405                 410                 415

Leu Arg Val Tyr Ser Ala Gly Ser Leu Asp Leu Ile Asn Glu Gln Thr
            420                 425                 430

Ala Phe Ile Ser Thr Gly Lys Asp Ser Thr Leu Lys Ala Thr Gly Thr
        435                 440                 445

Thr Glu Gly Gly Leu Tyr Gln Tyr Asp Leu Thr Gln Gly Ala Asp Gly
    450                 455                 460

Asn Phe Tyr Phe Val Lys Asn Thr His Lys Ala Ser Asn Ala Ser Ser
465                 470                 475                 480

Val Ile Gln Ala Met Ala Ala Pro Ala Asn Val Ala Asn Leu Gln
                485                 490                 495

Ala Asp Thr Leu Ser Ala Arg Gln Asp Ala Val Arg Leu Ser Glu Asn
            500                 505                 510

Asp Lys Gly Gly Val Trp Ile Gln Tyr Phe Gly Gly Lys Gln Lys His
        515                 520                 525

Thr Thr Ala Gly Asn Ala Ser Tyr Asp Leu Asp Val Asn Gly Val Met
    530                 535                 540

Leu Gly Gly Asp Thr Arg Phe Met Thr Glu Asp Gly Ser Trp Leu Ala
545                 550                 555                 560

Gly Val Ala Met Ser Ser Ala Lys Gly Asp Met Thr Met Gln Ser
                565                 570                 575

Lys Gly Asp Thr Glu Gly Tyr Ser Phe His Ala Tyr Leu Ser Arg Gln
            580                 585                 590
```

-continued

```
Tyr Asn Asn Gly Ile Phe Ile Asp Thr Ala Ala Gln Phe Gly His Tyr
            595                 600                 605

Ser Asn Thr Ala Asp Val Arg Leu Met Asn Gly Gly Thr Ile Lys
    610                 615                 620

Ala Asp Phe Asn Thr Asn Gly Phe Gly Ala Met Val Lys Gly Tyr
625                 630                 635                 640

Thr Trp Lys Asp Gly Asn Gly Leu Phe Ile Gln Pro Tyr Ala Lys Leu
                645                 650                 655

Ser Ala Leu Thr Leu Glu Gly Val Asp Tyr Gln Leu Asn Gly Val Asp
            660                 665                 670

Val His Ser Asp Ser Tyr Asn Ser Val Leu Gly Glu Ala Gly Thr Arg
            675                 680                 685

Val Gly Tyr Asp Phe Ala Val Gly Asn Ala Thr Val Lys Pro Tyr Leu
            690                 695                 700

Asn Leu Ala Ala Leu Asn Glu Phe Ser Asp Gly Asn Lys Val Arg Leu
705                 710                 715                 720

Gly Asp Glu Ser Val Asn Ala Ser Ile Asp Gly Ala Ala Phe Arg Val
                725                 730                 735

Gly Ala Gly Val Gln Ala Asp Ile Thr Lys Asn Met Gly Ala Tyr Ala
            740                 745                 750

Ser Leu Asp Tyr Thr Lys Gly Asp Asp Ile Glu Asn Pro Leu Gln Gly
            755                 760                 765

Val Val Gly Ile Asn Val Thr Trp
            770                 775

<210> SEQ ID NO 44
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is any amino acid such as a polar or
      charged amino acid
<220> FEATURE:
<221> NAME/KEY: MISC_FEATURE
<222> LOCATION: (8)..(8)
<223> OTHER INFORMATION: Xaa is any amino acid such as a non-polar amino
      acid
<220> FEATURE:
<221> NAME/KEY: MISC_FEATURE
<222> LOCATION: (9)..(9)
<223> OTHER INFORMATION: Xaa is any amino acid such as a polar amino
      acid;

<400> SEQUENCE: 44

Tyr Thr Phe Thr Xaa Tyr Trp Xaa Xaa
1               5

<210> SEQ ID NO 45
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is any amino acid such as a non-polar amino
      acid
<220> FEATURE:
<221> NAME/KEY: MISC_FEATURE
```

```
<222> LOCATION: (8)..(8)
<223> OTHER INFORMATION: Xaa is any amino acid such as a non-polar or
      polar amino acid
<220> FEATURE:
<221> NAME/KEY: MISC_FEATURE
<222> LOCATION: (9)..(9)
<223> OTHER INFORMATION: Xaa is any amino acid such as a polar amino
      acid
<220> FEATURE:
<221> NAME/KEY: MISC_FEATURE
<222> LOCATION: (11)..(11)
<223> OTHER INFORMATION: Xaa is any amino acid such as a non-polar or
      polar amino acid
<220> FEATURE:
<221> NAME/KEY: MISC_FEATURE
<222> LOCATION: (12)..(12)
<223> OTHER INFORMATION: Xaa is any amino acid such as a polar amino
      acid

<400> SEQUENCE: 45

Trp Ile Gly Asn Ile Xaa Pro Xaa Xaa Gly Xaa Xaa Asn Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is any amino acid such as a charged or
      non-polar amino acid
<220> FEATURE:
<221> NAME/KEY: MISC_FEATURE
<222> LOCATION: (4)..(4)
<223> OTHER INFORMATION: Xaa is any amino acid such as a polar amino
      acid
<220> FEATURE:
<221> NAME/KEY: MISC_FEATURE
<222> LOCATION: (5)..(5)
<223> OTHER INFORMATION: Xaa is either absent or is any amino acid such
      as a non-polar amino acid

<400> SEQUENCE: 46

Arg Xaa Gly Xaa Xaa Arg Ala Met Asp Tyr
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid such as a polar amino
      acid
<220> FEATURE:
<221> NAME/KEY: MISC_FEATURE
<222> LOCATION: (5)..(5)
<223> OTHER INFORMATION: Xaa is any amino acid such as a polar amino
      acid

<400> SEQUENCE: 47

Gln Ser Val Xaa Xaa Asp Val Ala
1               5

<210> SEQ ID NO 48
<211> LENGTH: 11
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is any amino acid such as a polar or
      non-polar amino acid
<220> FEATURE:
<221> NAME/KEY: MISC_FEATURE
<222> LOCATION: (5)..(5)
<223> OTHER INFORMATION: Xaa is any amino acid such as a polar or
      non-polar amino acid
<220> FEATURE:
<221> NAME/KEY: MISC_FEATURE
<222> LOCATION: (6)..(6)
<223> OTHER INFORMATION: Xaa is any amino acid such as a non-polar amino
      acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa is any amino acid such as a polar amino
      acid

<400> SEQUENCE: 48

Leu Leu Ile Xaa Xaa Xaa Ser Asn Arg Xaa Thr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa is any amino acid such as a polar or
      non-polar amino acid

<400> SEQUENCE: 49

Gln Gln Asp Tyr Ser Ser Pro Xaa
1               5
```

COMPOSITIONS AND METHODS FOR REDUCING BACTERIAL AGGREGATION

RELATED APPLICATIONS PARAGRAPH

This application is a continuation of International Patent Application No. PCT/AU2019/050893, filed Aug. 23, 2019, entitled "Compositions and Methods for Reducing Bacterial Aggregation". Foreign priority benefits are claimed under 35 U.S.C. § 119(a)-(d) or 35 U.S.C. § 365(b) of Australian Application No. 2018903096, filed Aug. 23, 2018. The contents of each of these applications are incorporated herein by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 13, 2022, is named L089570000US00-SEQ-JAV and is 97,926 bytes in size.

FIELD OF THE DISCLOSURE

The present disclosure relates to compositions and methods for inhibiting bacterial aggregation and in particular to compositions and methods that inhibit autotransporter-mediated bacterial aggregation or attachment.

BACKGROUND OF THE DISCLOSURE

Any discussion of the prior art throughout the specification should in no way be considered as an admission that such prior art is widely known or forms part of the common general knowledge in the field.

Biofilms are complex communities of bacteria living in close association with each other and a surface. Compared to planktonic cells, bacteria which are protected within a biofilm display resistance to conventional antibiotics, biocides and hydrodynamic shear forces (Bjarnsholt et al., Nat. Rev. Drug Discov. 2013. 12: 791-806).

Biofilms are significant threats in medical, industrial and environmental settings. Biofilms in the environment can lead to the persistence of foodborne pathogens. For example, biofilm formation by enterohemorrhagic *E. coli* (EHEC) O157:H7 can occur on plant surfaces (Torres et al., Appl. Environ. Microbiol. 2005. 71: 8008-15; Choi et al., J. Appl. Microbiol. 2011. 111: 1465-72), and more than 25% of outbreaks caused by these zoonotic shiga toxin-producing pathogens originate from contamination of commercial produce such as lettuce, spinach, cabbage, sprouts or tomatoes (Rangel et al., Emerg. Infect. Dis. 2005. 11(5): 603-9). In industrial settings, EHEC biofilm formation has also been observed on abiotic surfaces such as stainless steel, glass and plastic (Torres et al., Appl. Environ. Microbiol. 2005. 71: 8008-15; Dourou et al., Int. J. Food Microbiol. 2011. 149: 262-8).

Many bacterial infections in humans are associated with bacterial aggregation and biofilms. Respiratory and urinary tract infections, infections on medical devices and infections of the ear, gums and heart have all been associated with bacterial biofilms. Uropathogenic *E. coli*, for example, are responsible for 75 to 95% of all uncomplicated urinary tract infection (UTI) cases (Hooton, N. Engl. J. Med. 2012. 366(11): 1028-37). These infections cause significant morbidity and are of increasing concern due to the emergence of multi-drug-resistant strains (Totsika et al. 2012. Curr. Drug Targets 13(11): 1386-99).

Biofilms act to shield bacteria from host immune factors, as well as from antibiotic agents such as antimicrobial drugs and chemical detergents. Infections caused by bacteria that grow as aggregates in biofilms are therefore often chronic as they resist innate and adaptive defence mechanisms as well as antibiotics. Moreover, it has been suggested that as the aggregated bacteria in chronic infections are in close proximity to one another, genes coding for resistance to antibiotic agents can be passed horizontally from one bacterium to another (Bjarnsholt et al., Nat. Rev. Drug Discov. 2013. 12: 791-806). Current treatments for biofilm-associated infections include surgical removal of infected tissue or medical indwelling. Antibiotic agents are also used, however, they are often ineffective due to the shielding effect of the biofilm and due to the reduced metabolic activity of the aggregated bacteria.

In this context, there is a need for compositions and methods for reducing bacterial aggregation or biofilm formation.

SUMMARY OF THE DISCLOSURE

In work leading to the present disclosure, the inventors observed that a class of outer membrane and secreted proteins called autotransporters contribute to bacterial aggregation, biofilm formation and bacterial attachment to surfaces. Using structural, biochemical and functional techniques, the inventors found that homodimerisation of bacterial autotransporter proteins enables bacteria to aggregate and form biofilms. The inventors also found that autotransporter proteins contribute to bacterial attachment to surfaces. As described herein, the inventors have developed autotransporter-binding molecules which block autotransporter interactions and inhibit bacterial aggregation and biofilm formation.

In a first aspect, the present disclosure provides an isolated antibody or antigen binding fragment thereof comprising:

a) a CDRH3 comprising the sequence set forth in SEQ ID NO: 5 or a CDRL3 comprising the sequence set forth in SEQ ID NO: 8; or b) a CDRH3 comprising the sequence set forth in SEQ ID NO: 17 or a CDRL3 comprising the sequence set forth in SEQ ID NO: 20.

The isolated antibody or antigen binding fragment may comprise:

a) a CDRH3 comprising the sequence set forth in SEQ ID NO: 5 and a CDRL3 comprising the sequence set forth in SEQ ID NO: 8; or b) a CDRH3 comprising the sequence set forth in SEQ ID NO: 17 and a CDRL3 comprising the sequence set forth in SEQ ID NO: 20.

The isolated antibody or antigen binding fragment may comprise:

a) a CDRH1 comprising the sequence set forth in SEQ ID NO: 3;

a CDRH2 comprising the sequence set forth in SEQ ID NO: 4;

a CDRH3 comprising the sequence set forth in SEQ ID NO: 5;

a CDRL1 comprising the sequence set forth in SEQ ID NO: 6;

a CDRL2 comprising the sequence set forth in SEQ ID NO: 7; and a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

In certain examples, the isolated antibody or antigen binding fragment comprises:
a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8.

In certain examples, the isolated antibody or antigen binding fragment comprises:
a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

In a second aspect, the present disclosure provides an isolated antibody or antigen binding fragment thereof comprising:
a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or
b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

In some examples, the isolated antibody or antigen binding fragment comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

The isolated antibody or antigen binding fragment may comprise:
a) a VH comprising the sequence set forth in SEQ ID NO: 9 and a VL comprising the sequence set forth in SEQ ID NO: 10; or
b) a VH comprising the sequence set forth in SEQ ID NO: 21 and a VL comprising the sequence set forth in SEQ ID NO: 22.

The isolated antibody or antigen binding fragment may comprise:
a) a heavy chain comprising the sequence set forth in SEQ ID NO: 13 and a light chain comprising the sequence set forth in SEQ ID NO: 14; or
b) a heavy chain comprising the sequence set forth in SEQ ID NO: 25 and a light chain comprising the sequence set forth in SEQ ID NO: 26.

In a third aspect, the present disclosure provides an isolated antibody or antigen binding fragment thereof comprising:
a CDRH1 comprising the sequence set forth as formula (I)

$$YTFTX_1YWX_2X_3 \quad (I);$$

a CDRH2 comprising the sequence set forth as formula (II)

$$WIGNIX_4PX_5X_6GX_7X_8NY \quad (II);$$

a CDRH3 comprising the sequence set forth as formula (III)

$$RX_9GX_{10}X_{11}RAMDY \quad (III);$$

a CDRL1 comprising the sequence set forth as formula (IV)

$$QSVX_{12}X_{13}DVA \quad (IV);$$

a CDRL2 comprising the sequence set forth as formula (V)

$$LLIX_{14}X_{15}X_{16}SNRX_{17}T \quad (V); \text{ and}$$

a CDRL3 comprising the sequence set forth as formula (VI)

$$QQDYSSPX_{18} \quad (VI),$$

wherein:
$X_1$ is any amino acid such as a polar or charged amino acid;
$X_2$ is any amino acid such as a non-polar amino acid;
$X_3$ is any amino acid such as a polar amino acid;
$X_4$ is any amino acid such as a non-polar amino acid;
$X_5$ is any amino acid such as a non-polar or polar amino acid;
$X_6$ is any amino acid such as a polar amino acid;
$X_7$ is any amino acid such as a non-polar or polar amino acid;
$X_8$ is any amino acid such as a polar amino acid;

$X_9$ is any amino acid such as a charged or non-polar amino acid;
$X_{10}$ is any amino acid such as a polar amino acid;
$X_{11}$ is either absent or is any amino acid such as a non-polar amino acid;
$X_{12}$ is any amino acid such as a polar amino acid;
$X_{13}$ is any amino acid such as a polar amino acid;
$X_{14}$ is any amino acid such as a polar or non-polar amino acid;
$X_{15}$ is any amino acid such as a polar or non-polar amino acid;
$X_{16}$ is any amino acid such as a non-polar amino acid;
$X_{17}$ is any amino acid such as a polar amino acid; and
$X_{18}$ is any amino acid such as a polar or non-polar amino acid.

In certain examples:
$X_1$ is a polar or charged amino acid;
$X_2$ is a non-polar amino acid;
$X_3$ is a polar amino acid;
$X_4$ is a non-polar amino acid;
$X_5$ is a non-polar or polar amino acid;
$X_6$ is a polar amino acid;
$X_7$ is a non-polar or polar amino acid;
$X_8$ is a polar amino acid;
$X_9$ is a charged or non-polar amino acid;
$X_{10}$ is a polar amino acid;
$X_{11}$ is either absent or is a non-polar amino acid;
$X_{12}$ is a polar amino acid;
$X_{13}$ is a polar amino acid;
$X_{14}$ is a polar or non-polar amino acid;
$X_{15}$ is a polar or non-polar amino acid;
$X_{16}$ is a non-polar amino acid;
$X_{17}$ is a polar amino acid; and
$X_{18}$ is a polar or non-polar amino acid.

In certain examples:
$X_1$ is D or N;
$X_2$ is L or M;
$X_3$ is Y or H;
$X_4$ is I or G;
$X_5$ is F or S;
$X_6$ is N or S;
$X_7$ is G or N;
$X_8$ is S or T;
$X_9$ is R or W;
$X_{10}$ is T or S;
$X_{11}$ is either absent or is I;
$X_{12}$ is S or N;
$X_{13}$ is Y or N;
$X_{14}$ is F or Y;
$X_{15}$ is Y or F;
$X_{16}$ is V or A;
$X_{17}$ is S or Y; and
$X_{18}$ is F or Q.

In some examples, the isolated antibody or antigen binding fragment comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

According to a fourth aspect, the present disclosure provides an isolated antibody or antigen binding fragment thereof that binds to Ag43a (SEQ ID NO: 1) at an epitope comprising one or more residues selected from the group consisting of N83, R113, N114, D133, N150, T151, T152, G169, R254, E270, T291, T310, R330, G332, A333, S335, T361, N362, R364, T380, T381, S383, N386, S399, T401, D404 and G405.

The isolated antibody or antigen binding fragment may bind to one or more residues selected from the group consisting of R330, G332, A333, S335, T361, N362, R364, T380, T381, S383, N386, S399, T401, D404 and G405 of Ag43a (SEQ ID NO: 1).

In certain examples, the antibody or antigen binding fragment binds to one or more amino acid residues within amino acids 330 to 405 of Ag43a (SEQ ID NO: 1).

In certain examples, the antibody or antigen binding fragment binds to residues R330, G332, A333, S335, T361, N362, R364, T380, T381, S383, N386, S399, T401, D404 and G405 of Ag43a (SEQ ID NO: 1).

The antibody or antigen binding fragment may bind to Ag43a (SEQ ID NO: 1) with a $K_D$ of less than about 10 nM. In certain examples, the antibody or antigen binding fragment binds to Ag43a (SEQ ID NO: 1) with a $K_D$ of less than about 8 nM.

In some examples, the isolated antibody or antigen binding fragment comprises:
a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or
b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

In certain examples, the isolated antibody or antigen binding fragment comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;

a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

In a fifth aspect, the present disclosure provides an isolated antibody or antigen binding fragment thereof that competes for binding to Ag43a with an antibody or antigen binding fragment of any one of the first to fourth aspects.

In a sixth aspect, the present disclosure provides an isolated antibody or antigen binding fragment thereof that binds to the same epitope as the antibody or antigen binding fragment of any one of the first to fourth aspects.

In a seventh aspect, the present disclosure provides an isolated antibody or antigen binding fragment thereof that specifically binds to an autotransporter.

The isolated antibody or antigen binding fragment may specifically bind to a passenger domain of the autotransporter. In certain examples, the autotransporter is a homodimerising autotransporter. In certain examples, the antibody or antigen binding fragment inhibits homodimerisation of the autotransporter. In certain examples, the autotransporter is an AIDA-I type autotransporter. The autotransporter may be Ag43a, Ag43b, Ag43 or TibA. In certain examples, the autotransporter is Ag43a.

In certain examples, the antibody is a monoclonal antibody or an antigen binding fragment thereof.

The isolated antibody or antigen binding fragment may bind to the autotransporter with a $K_D$ of less than about 10 nM. In certain examples, the isolated antibody or antigen binding fragment binds to the autotransporter with a $K_D$ of less than about 8 nM.

In some examples, the isolated antibody or antigen binding fragment comprises:
a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or
b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

In certain examples, the isolated antibody or antigen binding fragment comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

In an eighth aspect, the present disclosure provides an isolated antibody or antigen binding fragment thereof that reduces binding of one autotransporter molecule to another autotransporter molecule.

The autotransporter may be an AIDA-I type autotransporter. In certain examples, the autotransporter molecule is Ag43a, Ag43b, Ag43 or TibA. In certain examples, the autotransporter molecule is Ag43a.

In some examples, the isolated antibody or antigen binding fragment comprises:
a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or
b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

In some examples, the isolated antibody or antigen binding fragment comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and
a CDRL3 comprising the sequence set forth in SEQ ID NO: 8; or
b) a CDRH1 comprising the sequence set forth in SEQ ID NO: 15;
a CDRH2 comprising the sequence set forth in SEQ ID NO: 16;
a CDRH3 comprising the sequence set forth in SEQ ID NO: 17;
a CDRL1 comprising the sequence set forth in SEQ ID NO: 18;
a CDRL2 comprising the sequence set forth in SEQ ID NO: 19; and
a CDRL3 comprising the sequence set forth in SEQ ID NO: 20.

In a ninth aspect, the present disclosure provides an isolated antibody or antigen binding fragment thereof that competes for binding to Ag43a with a control antibody, wherein the control antibody comprises:
a) a CDRH1 comprising the sequence set forth in SEQ ID NO: 3;
a CDRH2 comprising the sequence set forth in SEQ ID NO: 4;
a CDRH3 comprising the sequence set forth in SEQ ID NO: 5;
a CDRL1 comprising the sequence set forth in SEQ ID NO: 6;
a CDRL2 comprising the sequence set forth in SEQ ID NO: 7; and a CDRL3 comprising the sequence set forth in SEQ ID NO: 8; or b) a CDRH1 comprising the sequence set forth in SEQ ID NO: 15;

a CDRH2 comprising the sequence set forth in SEQ ID NO: 16;

a CDRH3 comprising the sequence set forth in SEQ ID NO: 17;

a CDRL1 comprising the sequence set forth in SEQ ID NO: 18;

a CDRL2 comprising the sequence set forth in SEQ ID NO: 19; and a CDRL3 comprising the sequence set forth in SEQ ID NO: 20.

In some examples, the control antibody reduces binding of the isolated antibody or antigen binding fragment to Ag43a by at least 20% when the control antibody and the isolated antibody or antigen binding fragment are used at approximately equal molar concentrations. In certain examples, the control antibody reduces binding of the isolated antibody or antigen binding fragment to Ag43a by at least 50% when the control antibody and the isolated antibody or antigen binding fragment are used at approximately equal molar concentrations.

In certain examples, the control antibody comprises:

a CDRH1 comprising the sequence set forth in SEQ ID NO: 3;

a CDRH2 comprising the sequence set forth in SEQ ID NO: 4;

a CDRH3 comprising the sequence set forth in SEQ ID NO: 5;

a CDRL1 comprising the sequence set forth in SEQ ID NO: 6;

a CDRL2 comprising the sequence set forth in SEQ ID NO: 7; and a CDRL3 comprising the sequence set forth in SEQ ID NO: 8.

In certain examples, the control antibody comprises:

a CDRH1 comprising the sequence set forth in SEQ ID NO: 15;

a CDRH2 comprising the sequence set forth in SEQ ID NO: 16;

a CDRH3 comprising the sequence set forth in SEQ ID NO: 17;

a CDRL1 comprising the sequence set forth in SEQ ID NO: 18;

a CDRL2 comprising the sequence set forth in SEQ ID NO: 19; and a CDRL3 comprising the sequence set forth in SEQ ID NO: 20.

In certain examples, the control antibody comprises:

a) a VH comprising the sequence set forth in SEQ ID NO: 9 and a VL comprising the sequence set forth in SEQ ID NO: 10; or b) a VH comprising the sequence set forth in SEQ ID NO: 21 and a VL comprising the sequence set forth in SEQ ID NO: 22.

In certain examples, the control antibody comprises:

a) a heavy chain comprising the sequence set forth in SEQ ID NO: 13 and a light chain comprising the sequence set forth in SEQ ID NO: 14; or b) a heavy chain comprising the sequence set forth in SEQ ID NO: 25 and a light chain comprising the sequence set forth in SEQ ID NO: 26.

In certain examples, the isolated antibody is a monoclonal antibody or an antigen binding fragment thereof. The isolated antibody may be a murine antibody or an antigen binding fragment thereof. The isolated antibody may be a chimeric antibody or an antigen binding fragment thereof. The isolated antibody may be a humanised antibody or an antigen binding fragment thereof. The isolated antibody may be a fully human antibody or antigen binding fragment thereof. The isolated antibody may be a bispecific or bivalent antibody or an antigen binding fragment thereof. The isolated antibody may be a multivalent antibody or an antigen binding fragment thereof. The isolated antibody or antigen binding fragment may be an antigen binding protein selected from the group consisting of a Fab fragment, a F(ab')2 fragment, a scFv, a scAb, a dAb, a diabody, a single domain heavy chain antibody and a single domain light chain antibody. In certain examples, the isolated antibody or antigen binding fragment is a Fab fragment. The isolated antibody or antigen binding fragment may be a full length IgG antibody. The isolated antibody or antigen binding fragment may be conjugated to a detectable moiety, a diagnostic agent or an antibiotic agent.

In a tenth aspect, the present disclosure provides an isolated nucleic acid encoding the antibody or antigen binding fragment of any one of the preceding aspects.

In an eleventh aspect, the present disclosure provides an isolated nucleic acid encoding a heavy chain variable region or a light chain variable region of the antibody or antigen binding fragment of any one of the first to ninth aspects.

In a twelfth aspect, the present disclosure provides an isolated nucleic acid encoding:

a VH comprising the sequence set forth in SEQ ID NO: 9 or SEQ ID NO: 21 or a sequence having at least 90% identity to SEQ ID NO: 9 or SEQ ID NO: 21; or a VL comprising the sequence set forth in SEQ ID NO: 10 or SEQ ID NO: 22 or a sequence having at least 90% identity to SEQ ID NO: 10 or SEQ ID NO: 22.

In certain examples, the isolated nucleic acid encodes:

a VH comprising the sequence set forth in SEQ ID NO: 9 or SEQ ID NO: 21; or a VL comprising the sequence set forth in SEQ ID NO: 10 or SEQ ID NO: 22.

In certain examples, the isolated nucleic acid encodes:

a heavy chain comprising the sequence set forth in SEQ ID NO: 13 or SEQ ID NO: 25 or a sequence having at least 90% identity to SEQ ID NO: 13 or SEQ ID NO: 25; or a light chain comprising the sequence set forth in SEQ ID NO: 14 or SEQ ID NO: 26 or a sequence having at least 90% identity to SEQ ID NO: 14 or SEQ ID NO: 26.

In a thirteenth aspect, the present disclosure provides an isolated expression vector comprising the isolated nucleic acid of any one of the tenth to twelfth aspects.

In a fourteenth aspect, the present disclosure provides a host cell comprising the isolated nucleic acid of any one of the tenth to twelfth aspects or the expression vector of the thirteenth aspect.

In a fifteenth aspect, the present disclosure provides a method of producing an antibody or antigen binding fragment the method comprising culturing the host cell of the fourteenth aspect under conditions that allow production of the antibody or antigen binding fragment and purifying the antibody or antigen binding fragment from the host cell.

In a sixteenth aspect, the present disclosure provides a composition comprising the isolated antibody or antigen binding fragment of any one of the first to ninth aspects and an antibiotic agent.

The antibiotic agent may be selected from the group consisting of aminoglycoside, polyene, nitroimidazole, rifamycin, bacitracin, a beta-lactam, cephalosporin, chloramphenicol, a glycopeptide, a macrolide, a lincosamide, penicillin, a quinolone, rifampicin, tetracycline, trimethoprim a sulfonamide, amoxicillin, augmentin, amoxicillin, ampicillin, azlocillin, flucloxacillin, mezlocillin, methicillin, cephalexin, cefazedone, cefuroxime, loracarbef, cemetazole, cefotetan, cefoxitin, ciprofloxacin, levaquin, floxacin, doxycycline, minocycline, gentamycin, amikacin, tobramycin, clarithromycin, azithromycin, erythromycin, daptomycin, neomycin, kanamycin, streptomycin, nisin, epidermin, gallidennin, cinnamycin, duramycin, lacticin 481, amoxicillin, amoxicillin/clavulanic acid, metronidazole, clindamycine, chlortetracycline, dcmeclocycline, oxytetracycline, amikacin, netilmicin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, claforan, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, clofazimine, colistimethate, colistin, cycloserine, fosfomycin, furazolidone, methenamine, nitrofurantoin, pentamidine, rifabutin, spectinomycin, tigecycline, trimethoprim, trimetrexate glucuronate, vancomycin, chlorhexidine, carbapenem, imipenem, cilastatin and ertapenem.

In a seventeenth aspect, the present disclosure provides a method of reducing aggregation of two or more bacteria the method comprising contacting the two or more bacteria with an effective amount of the antibody or antigen binding fragment of any one of the first to ninth aspects or the composition of the sixteenth aspect.

In certain examples, the two or more bacteria are *E. coli*. In some examples, the two or more bacteria are selected from the group consisting of avian pathogenic *E. coli* (APEC), diffusely adhering *E. coli* (DAEC), enterohemorrhagic *E. coli* (EHEC), enterotoxigenic *E. coli* (ETEC), shiga toxin-producing *E. coli* (STEC), enteropathogenic *E. coli* (EPEC) and uropathogenic *E. coli* (UPEC). The two or more bacteria may be UPEC. In certain examples, the two or more bacteria are UPEC strain CFT037.

In an eighteenth aspect, the present disclosure provides a method of inhibiting interaction between two or more autotransporter molecules the method comprising contacting at least one of said two or more autotransporter molecules with the antibody or antigen binding fragment of any one of the first to ninth aspects.

The two or more autotransporter molecules may be AIDA-I type autotransporters. In certain examples, the two or more autotransporter molecules are one of Ag43a, Ag43b, Ag43 or TibA. In certain examples, the two or more autotransporter molecules are Ag43a.

In a nineteenth aspect, the present disclosure provides a method of inhibiting homodimerisation between two autotransporter molecules the method comprising contacting at least one of said two autotransporter molecules with an autotransporter-binding molecule wherein the autotransporter-binding molecule binds to the at least one autotransporter molecule and thereby blocks homodimerisation between the two autotransporter molecules.

The autotransporter-binding molecule may be an antibody or an antigen binding fragment thereof. In certain examples, the antibody or antigen binding fragment is the antibody or antigen binding fragment of any one of the first to ninth aspects.

In some examples, the autotransporter-binding molecule binds to a passenger domain of the at least one autotransporter molecule. In some examples, the two autotransporter molecules are AIDA-I type autotransporters. The two autotransporter molecules may be one of Ag43a, Ag43b, Ag43 or TibA. In certain examples, the two autotransporter molecules are Ag43a.

In a twentieth aspect, the present disclosure provides a method of treating a bacterial infection in a subject, the method comprising administering to the subject a therapeutically effective amount of the antibody or antigen binding fragment of any one of the first to ninth aspects or the composition of the sixteenth aspect.

The bacterial infection may be a urinary tract infection, a respiratory tract infection, a gastrointestinal tract infection, a pulmonary infection, a throat infection, a mouth infection, a medical device related infection, an orthopaedic implant infection, a biliary stent related infection or a catheter related infection. In some examples, the bacterial infection is an *E. coli* infection. In certain examples, the *E. coli* is a strain of avian pathogenic *E. coli* (APEC), diffusely adhering *E. coli* (DAEC), enterohemorrhagic *E. coli* (EHEC), enterotoxigenic *E. coli* (ETEC), shiga toxin-producing *E. coli* (STEC), enteropathogenic *E. coli* (EPEC) or uropathogenic *E. coli* (UPEC). In certain examples, the *E. coli* is UPEC. In certain examples, the UPEC is strain CFT037.

In some examples, the bacterial infection is a urinary tract infection.

In a twenty-first aspect, the present disclosure provides a method of treating a disease or disorder associated with a bacterial infection in a subject the method comprising administering to the subject a therapeutically effective amount of the antibody or antigen binding fragment of any one of the first to ninth aspects or the composition of the sixteenth aspect.

The disease or disorder may be aerosacculitis, pneumonia, polyserositis, septicemia, diarrhoea, edema, a urinary tract infection, a respiratory tract infection, a gastrointestinal tract infection or a pulmonary infection. In certain examples, the disease or disorder is a urinary tract infection.

In a twenty-second aspect, the present disclosure provides a method of removing a bacterium from a surface the method comprising contacting the bacterium with an effective amount of an autotransporter-binding molecule wherein the autotransporter-binding molecule binds to an autotransporter molecule expressed by the bacterium.

In some examples, the autotransporter-binding molecule is the antibody or antigen binding fragment of any one of the first to ninth aspects.

In a twenty-third aspect, the present disclosure provides a method of inhibiting autotransporter-mediated attachment of a bacterium to a surface, the method comprising contacting the bacterium with an effective amount of an autotransporter-binding molecule, wherein the autotransporter-binding molecule binds to an autotransporter molecule expressed by the bacterium and thereby inhibits an interaction between the autotransporter molecule and the surface.

In some examples, the autotransporter-binding molecule is an antibody or antigen binding fragment thereof.

In some examples, the autotransporter-binding molecule binds to a passenger domain of the autotransporter molecule. In certain examples, the autotransporter is an AIDA-I type autotransporter. In certain examples, the autotransporter molecule is UpaB.

In some examples, the surface is a medical device surface or personal care device surface. The surface may be a surface of an orthopaedic implant, a stent, a catheter, a prosthesis, a pacemaker or a contact lens.

In some examples, the surface is a cellular surface of a eukaryotic organism. In certain examples, the eukaryotic organism is an animal. The cellular surface may be a urinary tract surface or a gastrointestinal tract surface.

In a twenty-fourth aspect, the present disclosure provides a method of inhibiting autotransporter-mediated aggregation of two or more bacteria wherein the two or more bacteria express an autotransporter molecule, the method comprising contacting the two or more bacteria with an effective amount of an autotransporter-binding molecule, wherein the autotransporter-binding molecule binds to the autotransporter molecule and thereby inhibits aggregation of the two or more bacteria.

In some examples, the autotransporter-binding molecule binds to a passenger domain of the autotransporter molecule. The autotransporter may be an AIDA-I type autotransporter. In certain examples, the autotransporter molecule is Ag43a, Ag43b, Ag43 or TibA. In certain examples, the autotransporter molecule is Ag43a.

In some examples, the autotransporter-binding molecule may an antibody or antigen binding fragment thereof. The antibody or antigen binding fragment thereof may be the antibody or antigen binding fragment of any one of the first to ninth aspects.

In a twenty-fifth aspect, the present disclosure provides use of the antibody or antigen binding fragment of any one of the first to ninth aspects or the composition of the sixteenth aspect in the manufacture of a medicament for reducing aggregation of two or more bacteria.

In a twenty-sixth aspect, the present disclosure provides use of the antibody or antigen binding fragment of any one of the first to ninth aspects or the composition of the sixteenth aspect in the manufacture of a medicament for inhibiting interaction between two or more autotransporter molecules.

In a twenty-seventh aspect, the present disclosure provides use of an autotransporter-binding molecule in the manufacture of a medicament for inhibiting homodimerisation between two autotransporter molecules wherein the autotransporter-binding molecule binds to at least one of the autotransporter molecules and thereby blocks homodimerisation between the two autotransporter molecules.

In a twenty-eighth aspect, the present disclosure provides use of the antibody or antigen binding fragment of any one of the first to ninth aspects or the composition of the sixteenth aspect in the manufacture of a medicament for treating a bacterial infection in a subject.

In a twenty-ninth aspect, the present disclosure provides use of the antibody or antigen binding fragment of any one of the first to ninth aspects or the composition of the sixteenth aspect in the manufacture of a medicament for treating a disease or disorder associated with a bacterial infection in a subject.

In a thirtieth aspect, the present disclosure provides use of an autotransporter-binding molecule in the manufacture of a medicament for removing a bacterium from a surface wherein the autotransporter-binding molecule binds to an autotransporter molecule expressed by the bacterium.

In a thirty-first aspect, the present disclosure provides use of an autotransporter-binding molecule in the manufacture of a medicament for inhibiting autotransporter-mediated attachment of a bacterium to a surface wherein the autotransporter-binding molecule binds to an autotransporter molecule expressed by the bacterium and thereby inhibits an interaction between the autotransporter molecule and the surface.

In a thirty-second aspect, the present disclosure provides use of an autotransporter-binding molecule in the manufacture of a medicament for inhibiting autotransporter-mediated aggregation of two or more bacteria wherein the two or more bacteria express an autotransporter molecule, and wherein the autotransporter-binding molecule binds to the autotransporter molecule and thereby inhibits aggregation of the two or more bacteria.

BRIEF DESCRIPTION OF THE DRAWINGS

FIG. 1. Structural and functional characterisation of the Ag43a passenger domain. A. Surface representation and ribbon structure of the Ag43a passenger domain. B. Head-to-tail self-association between Ag43a$^\alpha$ molecules. C. Interface between Ag43a$^\alpha$ molecules. D. Crystal packing of Ag43a$^\alpha$. E. *E. coli* cell aggregation assay and Western blot using the agn43 null strain MS427 transformed with an empty vector, a vector expressing wild-type Ag43a or a vector expressing a mutant version of Ag43a.

DETAILED DESCRIPTION

Definitions

Figure 1:
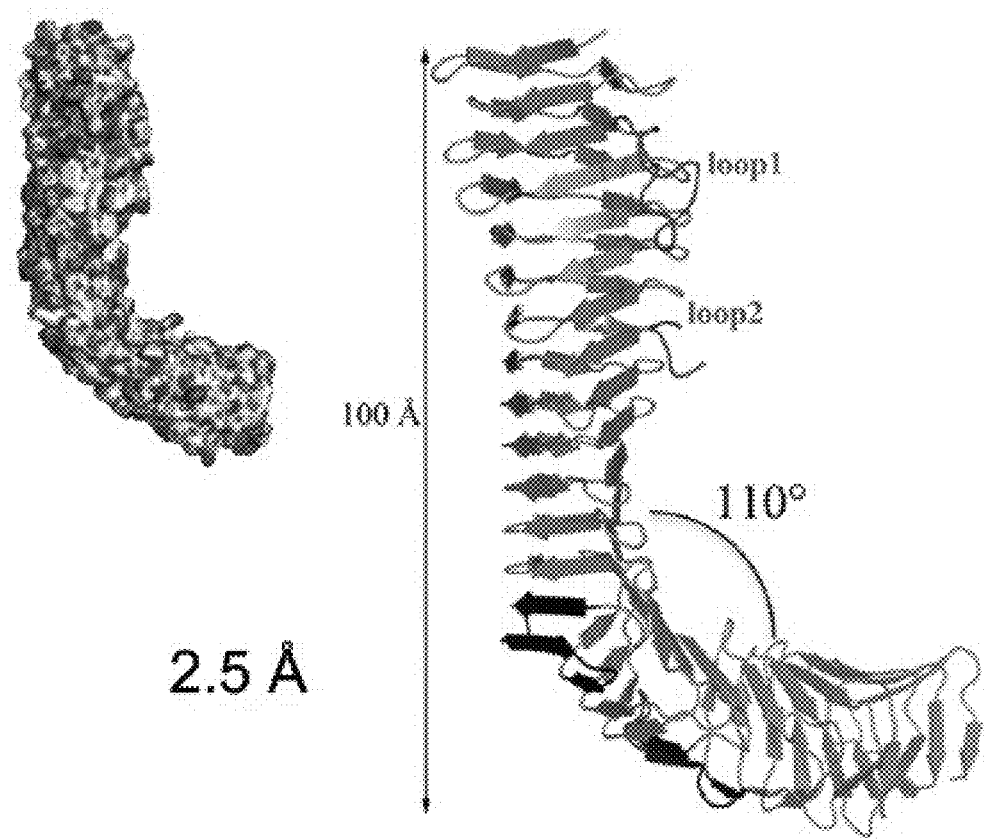
Figure 1:
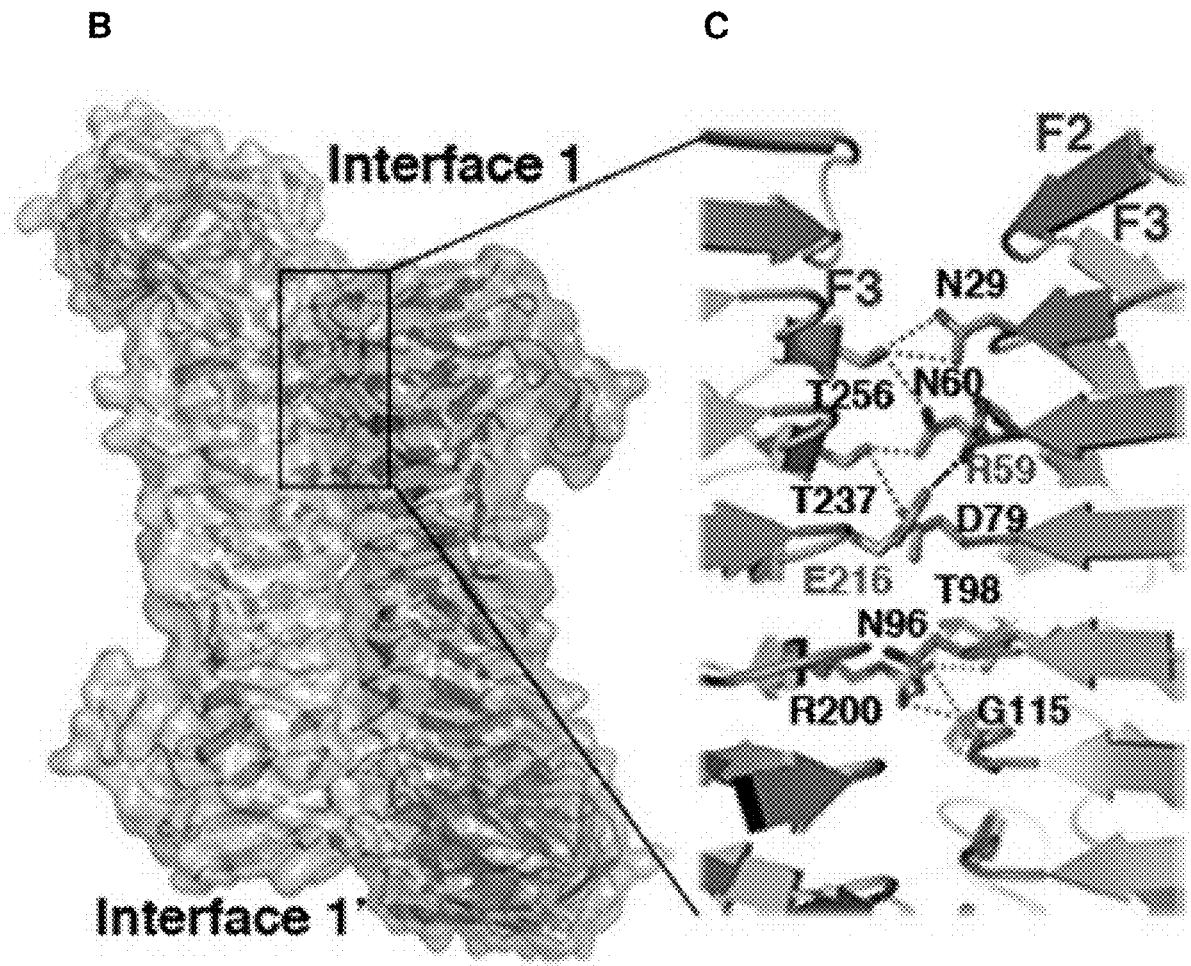
Figure 1:
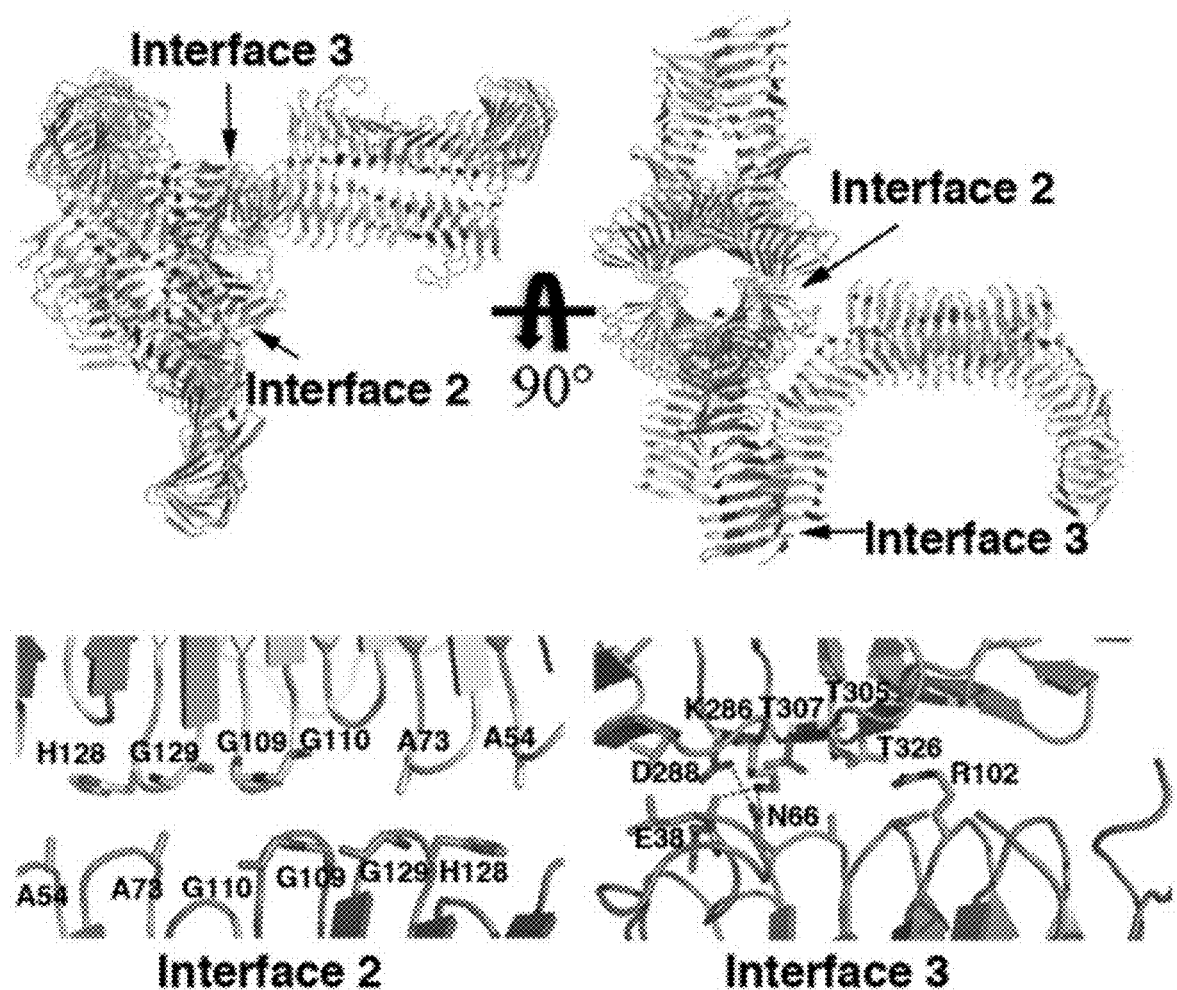
Figure 1:
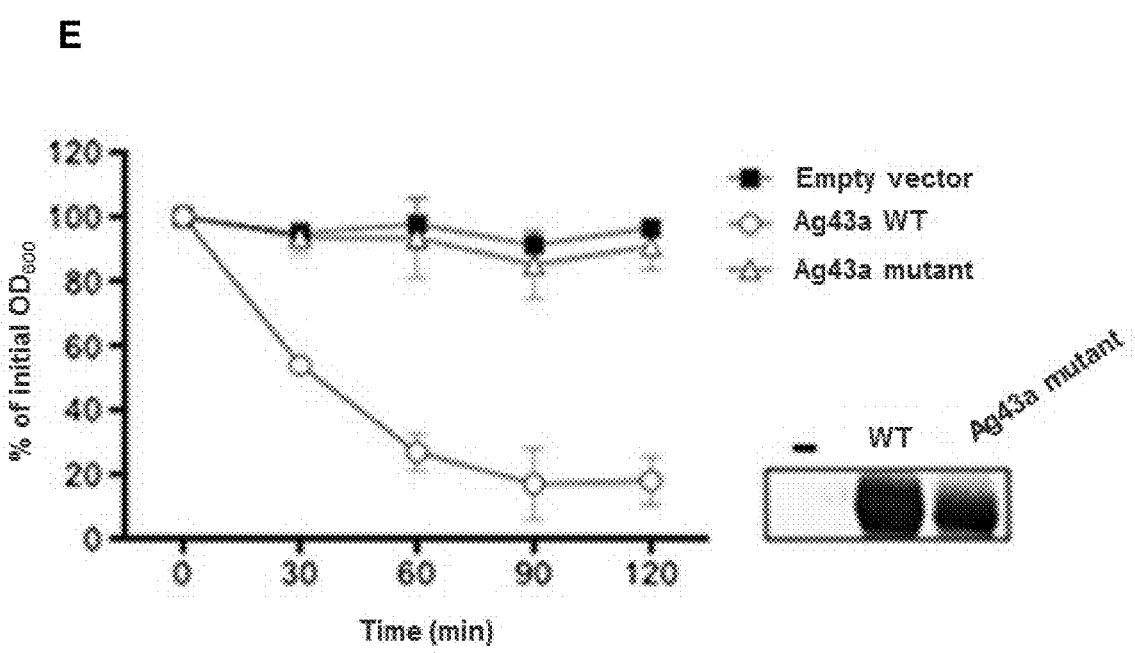

In the context of this specification, the terms "a" and "an" are used herein to refer to one or to more than one (i.e. to at least one) of the grammatical object of the article. By way of example, "an element" means one element or more than one element.

The term "about" is understood to refer to a range of +/−10%, preferably +/−5% or +/−1% or, more preferably, +/−0.1%.

The terms "administration concurrently" or "administering concurrently" or "co-administering" and the like refer to the administration of a single composition containing two or more actives, such as an autotransporter-binding molecule and an antibiotic, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation.

As used herein, the term "antibody" refers to any form of antibody that exhibits the desired biological activity. Thus, it is used in a broad sense and includes, but is not limited to, monoclonal antibodies (including full length monoclonal antibodies comprising two light chains and two heavy chains), polyclonal antibodies, multispecific antibodies (eg, bispecific antibodies), humanized antibodies, fully human antibodies, chimeric antibodies and camelized single domain antibodies. Single domain antibodies are composed of single VH or VL domains.

Naturally occurring antibody structural units typically comprise a tetramer. Each such tetramer typically comprises two pairs of polypeptide chains, each pair having one full-length "light" and one full-length "heavy" chain. The amino-terminal portion of each chain typically includes a variable region of about 100 to 110 or more amino acids that is usually responsible for antigen recognition. The carboxy-terminal portion of each chain typically includes a constant region that may be responsible for effector function. Human light chains are typically classified as kappa and lambda light chains. Heavy chains are typically classified as mu, delta, gamma, alpha or epsilon, and define the antibody's isotype as IgM, IgD, IgG, IgA and IgE, respectively. IgG has several subclasses, including IgG1, IgG2, IgG3 and IgG4. IgM has subclasses including IgM1 and IgM2. IgA is similarly subdivided into subclasses including IgA1 and IgA2. Within full-length light and heavy chains, often, the variable and constant regions are joined by a "J" region of about 12 or more amino acids, with the heavy chain also including a "D" region of about 10 more amino acids (see, eg, Fundamental Immunology, Ch. 7 (Paul, W., ed., 2nd ed. Raven Press, N.Y. 1989). The variable regions of each light/heavy chain pair typically comprise the antigen binding site.

The term "antigen" as used herein refers to all, or part of, a molecule (eg, a protein, peptide, or other molecule or macromolecule) that is capable of being bound by an antibody or an antigen binding protein.

As used herein, the term "antigen binding protein" refers to a protein that specifically binds to one or more target antigens. An antigen binding protein can include an antibody and binding fragments thereof. An "antigen binding fragment" or "antigen binding portion" used interchangeably in certain contexts herein with "binding fragment" or "fragment" is a portion of an antibody that lacks at least some of the amino acids present in a full-length heavy chain and/or light chain, but which is still capable of specifically binding to an antigen. An antigen binding fragment includes, but is not limited to, a single-chain variable fragment (scFv), a nanobody (eg, VH domain of camelid heavy chain antibodies; VHH fragment), a Fab fragment, a Fab' fragment, a F(ab')2 fragment, a Fv fragment and a Fd fragment, and may be derived, for example, from a mammalian source, such as human, mouse, rat, rabbit or camelid. Antigen binding fragments may compete for binding to a target antigen with an intact antibody and the fragments may be produced by the modification of intact antibodies (eg, enzymatic or chemical cleavage) or synthesized de novo using recombinant DNA technologies or peptide synthesis.

An antigen binding protein may also include a protein comprising one or more antigen binding fragments incorporated into a single polypeptide chain or into multiple polypeptide chains. For example, antigen binding proteins may include, but are not limited to, a diabody (see, eg, EP 404,097; WO 93/11161; and Hollinger et al, Proc. Natl. Acad. Sci. USA. 1993. Vol. 90: 6444-6448), an intrabody, a domain antibody (single VL or VH domain or two or more VH domains joined by a peptide linker; see, eg, Ward et al, Nature. 1989. Vol. 341:544-546), a maxibody (2 scFvs fused to Fc region, see, eg, Fredericks et al. Prot. Eng. Des. Sel. 2004. 17:95-106; and Powers et al. J. Immunol. Meth. 2001. 251: 123-135), a triabody, a tetrabody, a minibody (scFv fused to CH3 domain; see, eg, Olafsen et al. Prot. Eng. Des. Sel. 2004. 17:315-23), a peptibody (one or more peptides attached to an Fc region, see, eg, WO 00/24782), a linear antibody (a pair of tandem Fd segments (VH-$CH_1$-VH-$CH_1$) which, together with complementary light chain polypeptides, form a pair of antigen binding regions, see, eg, Zapata et al., Protein Eng., Vol. 8: 1057-1062, 1995), a small modular immunopharmaceutical (see, eg, U.S. Patent Publication No. 20030133939), and immunoglobulin fusion proteins (e.g. IgG-scFv, IgG-Fab, 2scFv-IgG, 4scFv-IgG, VH-IgG, IgG-VH, and Fab-scFv-Fc; see, eg, Spiess et al, Mol. Immunol., Vol. 2015. 67(2 Pt A):95-106).

By "autologous" is meant something (eg, cells, tissues etc) derived from the same organism.

The term "bispecific" as used herein refers to an antibody or antigen binding protein which comprises at least a first binding domain and a second binding domain, wherein the first binding domain binds to one antigen or target, and the second binding domain binds to another antigen or target. The term "bispecific" may also encompass multispecific antibody constructs such as trispecific antibody constructs, the latter including three binding domains having three specificities.

A "bivalent antigen binding protein" or "bivalent antibody" comprises two antigen binding sites. In some instances, the two binding sites have the same antigen specificities. Bivalent antigen binding proteins and bivalent antibodies can be bispecific.

As used herein, a "chimeric antibody" is an antibody having the variable domain from a first antibody and the constant domain from a second antibody, where the first and second antibodies are from different species. (U.S. Pat. No. 4,816,567; and Morrison et al. Proc. Natl. Acad. Sci. USA. 1984. 81: 6851-6855). Typically, the variable domains are obtained from an antibody of an experimental animal such as a rodent, and the constant domain sequences are often obtained from human antibodies, so that the resulting chimeric antibody will be less likely to elicit an adverse immune response in a human subject than the parental (eg, mouse) antibody.

The terms "complementarity determining region" and "CDR" refer to the complementarity determining region, of which, up to three make up the binding character of a light chain variable region (CDRL1, CDRL2 and CDRL3) and up to three make up the binding character of a heavy chain variable region (CDRH1, CDRH2 and CDRH3). CDRs contain most of the residues responsible for specific interactions of an antibody with an antigen and hence contribute to the functional activity of an antibody molecule.

The CDR regions may be delineated by different classification and numbering systems, however the Kabat system is generally preferred (see, eg, Kabat, E. A. et al, 1991, Sequences of Proteins of Immunological Interest, Fifth Edition, U.S. Department of Health and Human Services, NTH Publication No, 91-3242).

The CDR3 of the light chain and, particularly, the CDR3 of the heavy chain may constitute the most important determinants in antigen binding within the light and heavy chain variable regions. In some instances, the heavy chain CDR3 may constitute the major area of contact between the antigen and the antibody. In vitro selection schemes in which the CDR3 alone is varied can be used to vary the binding properties of an antibody or determine which residues contribute to the binding of an antigen. Hence, CDR3 is typically the greatest source of molecular diversity within the antibody-binding site.

The terms "comprise", "comprises", "comprised" or "comprising", "including" or "having" and the like in the present specification and claims are used in an inclusive sense, ie, to specify the presence of the stated features but not preclude the presence of additional or further features.

As used herein, the term "diabodies" refers to small antibody fragments with two antigen-binding sites, which fragments comprise a heavy chain variable domain (VH) connected to a light chain variable domain (VL) in the same polypeptide chain (VH-VL or VL-VH). By using a linker that is too short to allow pairing between the two domains on the same chain, the domains may be forced to pair with the complementary domains of another chain and create two antigen-binding sites. Diabodies are described further in, eg, EP 404,097; WO93/11161; and Holliger et al. Proc. Natl. Acad. Sci. USA. 1993. 90: 6444-6448.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

The term "epitope" refers to a site on an antigen to which a binding domain, such as from an antibody, fragment or antigen binding protein, specifically binds. An epitope may be formed both by contiguous amino acids or non-contiguous amino acids juxtaposed by folding of a protein.

The term "epitope mapping" refers to the process of identifying the molecular determinants on the antigen involved in antibody-antigen recognition.

A "Fab fragment" comprises one light chain and the CH1 and variable regions of one heavy chain. Generally, the heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule.

A "F(ab')$_2$ fragment" comprises two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

An "Fc" region comprises two heavy chain fragments comprising the CH2 and CH3 domains of an antibody. The two heavy chain fragments are typically held together by two or more disulfide bonds and by hydrophobic interactions of the CH3 domains.

The "Fv" region comprises the variable regions from both the heavy and light chains, but lacks the constant regions.

The term "host cell" includes an individual cell or cell culture which can be or has been a recipient of a recombinant vector or isolated polynucleotide of the disclosure. Host cells include progeny of a single host cell, and the progeny may not necessarily be completely identical (genetically or morphologically) to the original parent cell due to natural, accidental, or deliberate mutation and/or change. A host cell includes cells transfected or infected in vivo or in vitro with a recombinant vector or a polynucleotide of the disclosure.

"Humanized" antibodies are antibodies or immunoglobulins that largely comprise human sequences, and which contain (a) minimal sequence(s) derived from non-human immunoglobulin. Humanized antibodies are largely human immunoglobulins (recipient antibody) in which residues from a hypervariable region of the recipient are replaced with residues from a hypervariable region of a non-human (eg, rodent) species (donor antibody) such as mouse, rat, hamster or rabbit having the desired specificity. In some instances, Fv framework region residues of the human immunoglobulin are replaced with corresponding non-human residues. Furthermore, humanized antibodies may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin (see, eg, Jones et al. Nature. 1986. 321: 522-525; Reichmann et al. Nature. 1988. 332: 323-329; and Presta, Curr. Op. Struct. Biol. 1992. 2: 593-596).

The term "identity" refers to a relationship between the sequences of two or more polypeptide molecules or two or more nucleic acid molecules, as determined by aligning and comparing the sequences. The percent identity between two sequences is a function of the number of identical positions shared by the sequences when the sequences are optimally aligned, with optimal alignment determined taking into account the number of gaps, and the length of each gap, which need to be introduced for optimal alignment of the two sequences. The comparison of sequences and determination of percent identity between two sequences can be accomplished using a mathematical algorithm.

The percent identity between two nucleotide sequences can be determined using the GAP program in the GCG software package, using a NWSgapdna.CMP matrix and a gap weight of 40, 50, 60, 70 or 80 and a length weight of 1, 2, 3, 4, 5 or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 1970. 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The term "isolated" as used herein refers to material that is substantially or essentially free from components that normally accompany it in its native state. For example, an isolated polynucleotide as used herein refers to a polynucleotide which has been purified from the sequences which flank it in a naturally-occurring state, eg, a DNA fragment which has been removed from the sequences that are normally adjacent to the fragment. Alternatively, an isolated antibody or antigen binding fragment thereof and the like, as used herein, refer to in vitro isolation and/or purification of the antibody or fragment from its cellular environment, and from association with other components of the cell, ie, it is not associated with in vivo substances. An isolated antibody or antigen binding fragment will generally encompass recombinantly expressed antibodies and antigen binding fragments.

The term "monoclonal antibody" (mAb) as used herein refers to an antibody obtained from a population of substantially homogeneous antibodies, ie, the individual antibodies comprising the population are identical except for possible naturally occurring mutations and/or post-translation modifications (eg, isomerizations, amidations) that may be present in minor amounts. Monoclonal antibodies are highly specific, being directed against a single antigenic site or determinant on the antigen (epitope), in contrast to polyclonal antibody preparations which typically include different antibodies directed against different epitopes. Monoclonal antibodies are typically synthesized by hybridoma culture, and are hence uncontaminated by other immunoglobulins. The term "monoclonal" indicates the character of the antibody as being obtained from a substantially homogeneous population of antibodies, and is not to be construed as requiring production of the antibody by any particular method.

The term "operably connected" or "operably linked" as used herein refers to the functional relationship between two or more nucleic acid segments such as a gene and a regulatory element including but not limited to a promoter, which then regulates the expression of the gene.

The term "oligonucleotide" as used herein refers to a polymer of nucleotides (eg, deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes analogues including, but not restricted to, peptide nucleic acids (PNAs), phosphoramidates, phosphorothioates, methyl phosphonates, 2-O-methyl ribonucleic acids, and the like. The size of an oligonucleotide can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "pharmaceutically acceptable" as used herein refers to substances that do not cause substantial adverse allergic or immunological reactions when administered to a subject. A "pharmaceutically acceptable carrier" includes, but is not limited to, solvents, coatings, dispersion agents, wetting agents, isotonic and absorption delaying agents and disintegrants.

The term "polynucleotide variant" refers to polynucleotides displaying substantial sequence identity with a reference polynucleotide sequence or polynucleotides that hybridize with a reference sequence under stringent conditions. The term also encompasses polynucleotides that are distinguished from a reference polynucleotide by the addition, deletion or substitution of at least one nucleotide. Accordingly, the term "polynucleotide variant" includes polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The term "polynucleotide variant" also includes naturally occurring allelic variants. The terms "peptide variant" and "polypeptide variant" and the like includes peptides and polypeptides that are distinguished from a reference peptide or polypeptide by the addition, deletion or substitution of at least one amino acid residue. In certain embodiments, a peptide or polypeptide variant is distinguished from a reference peptide or polypeptide by one or more substitutions, which may be conservative or non-conservative. In certain embodiments, the peptide or polypeptide variant comprises conservative substitutions and, in this regard, it is well understood in the art that some amino acids may be changed to others with broadly similar properties without changing the nature of the activity of the peptide or polypeptide. Peptide and polypeptide variants also encompass peptides and polypeptides in which one or more amino acids have been added or deleted, or replaced with different amino acid residues The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

The term "recombinant polypeptide" as used herein refers to a polypeptide made using recombinant techniques, ie, through the expression of a recombinant polynucleotide.

The term "regulatory element" or "regulatory sequence" refers to a nucleic acid sequence which regulates expression of an operably linked coding sequence in a particular host cell. Regulatory sequences that are suitable for prokaryotic cells for example, include a promoter, and optionally a cis-acting sequence such as an operator sequence and a ribosome binding site. Control sequences that may be suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

"Single-chain antibodies" are Fv molecules in which the heavy and light chain variable regions have been connected by a flexible linker to form a single polypeptide chain, which forms an antigen binding region. Single chain antibodies are discussed further in WO 88/01649 and U.S. Pat. Nos. 4,946,778 and 5,260,203. The term "single-chain Fv" or "scFv" antibody refers to antibody fragments comprising the VH and VL domains of an antibody, wherein these domains are present in a single polypeptide chain. The Fv polypeptide often further comprises a polypeptide linker between the VH and VL domains which enables the scFv to form the desired structure for antigen-binding.

In the context of this specification, the term "therapeutically effective amount" refers to a non-toxic but sufficient amount of the composition or agent to which it refers to provide the desired therapeutic effect.

The term "vector" refers to a polynucleotide molecule, suitably a DNA molecule derived, for example, from a plasmid, bacteriophage, yeast or virus, into which a polynucleotide is, or can be, inserted or cloned. A vector may contain one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, ie, a vector that exists as an extra-chromosomal entity, the replication of which is independent of chromosomal replication, eg, a linear or closed circular plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector may depend on the compatibility of the vector with the host cell into which the vector is to be introduced. The vector may also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

Autotransporter Proteins

Autotransporter proteins are a large family of non-fimbrial adhesins and are the largest group of cell surface and secreted proteins in gram negative bacteria. They mediate several ecological and virulence phenotypes including surface adhesion, host cell adhesion, host cell invasion, toxicity, bacterial aggregation and biofilm formation.

Autotransporter proteins (also referred to herein as autotransporter molecules and autotransporters) have a shared domain architecture which comprises an N-terminal signal sequence that directs secretion of the protein across the inner membrane via the general secretory pathway, a passenger (a) domain that is either anchored to the cell surface or released into the external milieu and determines the functional characteristics of the protein, and a translocation (13) domain that inserts into the outer membrane (Busscher et al. FEMS Microbiol. Lett. 1995. 128: 129). The translocation domain comprises a β-barrel structure, which is embedded in the outer membrane and assists in the transport of the passenger domain to the cell surface.

*Escherichia coli* autotransporters can be classified into three groups, namely, the serine protease autotransporters of Enterobacteriaceae (SPATEs), the trimeric autotransporter adhesins, and the AIDA-I-type autotransporter adhesins. The AIDA-I-type autotransporters are the largest group within the autotransporter family. These proteins play a crucial role in surface adhesion as well as bacterial pathogenesis by promoting colonisation and invasion of host cells, and by facilitating the persistence of infections through the formation of bacterial aggregates and biofilms.

All AIDA-I-type autotransporters are predicted to adopt a common domain architecture; the translocation domain folds into a canonical β-barrel, and the passenger domain generally incorporates a right-handed β-helix (Leyton et al. Nat. Rev. Microbiol. 2012. 10(3): 213-225). The AIDA-I-type group of autotransporters includes Ag43, Ag43a, Ag43b, AatA, AIDA-I, EhaA, EhaB, EhaC, EhaD, TibA, UpaB, UpaC, UpaH, YfaL, YejO, YdeK and YcgV.

AatA exhibits the greatest prevalence in extraintestinal *E. coli*, particularly in avian pathogenic *E. coli* (APEC). It functions as an adhesin to fibroblasts and connective tissue, and aids bacterial aggregation and biofilm formation (Dai et al. BMC Microbiol. 2010. 10: 236; Wang et al. FEMS Immunol. Med. Microbiol. 2011. 63: 328). AatA contributes to a variety of disorders including aerosacculitis, pneumonia, polyserositis and septicemia. AIDA-I is present in many types of *E. coli*, including diffusely adhering *E. coli* (DAEC) in humans, and enterotoxigenic *E. coli* (ETEC), shiga toxin-producing *E. coli* (STEC) and enteropathogenic *E. coli* (EPEC) in pigs. AIDA-I promotes adhesion to, and invasion of, epithelial cells, intestinal colonisation, bacterial aggregation and biofilm formation, contributing to diarrhoeal diseases such as edema (Jallat et al. J. Clin. Microbiol. 1993. 31: 2031; Zhang et al. Vet. Microbiol. 2007. 123: 145; Niewerth et al. Clin. Diagn. Lab. Immunol. 2001. 8: 143; Zhao et al. Vet. J. 2009. 180: 124). TibA is primarily present in ETEC strains and self-associates to form bacterial aggregates and biofilms, to promote colonisation and invasion of intestinal epithelia and to protect bacteria from host immune factors and antimicrobial agents (Elsinghorst et al. Infect. Immun. 1994. 62: 3463; Sherlock et al. Infect. Immun. 2005. 73: 1954). TibA contributes to a range of diarrhoeal diseases. UpaB is present in many pathogenic and extraintestinal strains of *E. coli* including uropathogenic *E. coli* (UPEC), APEC as well as commensal strains (Zude et al. Int. J. Med. Microbiol. 2014. 304: 243). It contributes to urinary tract infections, aerosacculitis, pneumonia, polyserositis, septicemia and diarrhoeal diseases. Similar to UpaB, UpaC is found in many pathogenic and commensal strains of *E. coli* (Zude et al. Int. J. Med. Microbiol. 2014. 304: 243; Allsopp et al. Infect. Immun. 2012. 80: 321). It facilitates biofilm formation and contributes to UTIs. UpaH is most prevalent in UPEC isolates where it facilitates adhesion to ECM proteins and promotes biofilm formation (Zude et al. Int. J. Med. Microbiol. 2014. 304: 243; Allsopp et al. Infect. Immun. 2010. 78: 1659; Allsopp et al. J. Bacteriol. 2012. 194: 5769). UpaH also contributes to UTIs. EhaA, EhaB, EhaC and EhaD are among the most widespread and prevalent AIDA-type autotransporters throughout *E. coli*. EhaA promotes adhesion to epithelial cells, and facilitates bacterial cell aggregation and biofilm formation (Wells et al. Environ. Microbiol. 2008. 10: 589). It is found in enterohemorrhagic *E. coli* (EHEC) and contributes to haemorrhagic colitis. EhaB promotes adhesion to ECM proteins and facilitates biofilm formation (Wells et al. Environ. Microbiol. 2008. 10: 589; Wells et al. Environ. Microbiol. 2009. 11: 1803). It is found in EHEC and STEC, and contributes to haemorrhagic colitis and foodborne disease. YfaL, YcgV and YpjA are present in several *E. coli* strains including K-12, and contribute to biofilm formation and adhesion to abiotic surfaces such as glass and PVC (Roux et al. J. Bacteriol. 2005. 187: 1001).

Antigen 43 (Ag43) is a member of the AIDA-I-type autotransporter proteins, and is produced as a preprotein including an N-terminal signal peptide that directs translocation across the cytoplasmic membrane into the periplasm and a classical passenger ($\alpha^{43}$)-translocation ($\beta^{43}$) domain structure (Heras et al. Proc. Natl. Acad. Sci. USA. 2014. 111(1): 457-462). Processing of Ag43 occurs between the $\alpha^{43}$ and $\beta^{43}$ domains, however, the two subunits remain in contact via noncovalent interactions (Henderson et al. Microbiol. Mol. Biol. Rev. 2004. 68(4): 692-744), with the $\alpha^{43}$ domain protruding about 10 nm from the cell surface. Ag43 is found in most *E. coli* pathotypes including uropathogenic *E. coli*(UPEC). Ag43a from the UPEC strain CFT073 mediates aggregation, biofilm formation and urinary tract colonisation. Ag43 from the UPEC strain UT189 is also associated with the formation of intracellular bacterial communities that resemble biofilms and contribute to chronic urinary tract infection (Anderson et al. Science. 2003. 301(5629): 105-107).

Antibody Generation

Those skilled in the art will be aware of various methods that may be used to generate antibodies and antigen binding proteins of the present disclosure. For example, antibodies of the present disclosure may be produced by immunising a non-human animal, eg, a rodent, with a target autotransporter or a fragment thereof. In certain embodiments, the antibodies of the present disclosure are monoclonal antibodies. Monoclonal antibodies can be produced using a variety of techniques known in the art including by using hybridoma technologies, recombinant DNA technologies, and phage display technologies, or a combination thereof. Other techniques for producing human monoclonal antibodies include the trioma technique, the human B-cell hybridoma technique and the EBV-hybridoma technique.

Phage display is described in U.S. Pat. No. 5,223,409; Smith, Science. 1985. 228:1315-1317, Clackson et al. Nature. 1991. 352: 624-628 and Marks et al. J. Mol. Biol. 1991. 222: 581-597.

Those skilled in the art will be aware of several techniques for producing monoclonal antibodies using hybridoma technology. By way of non-limiting example, splenocytes and/or lymph node cells from immunized mice may be isolated and fused to an appropriate immortalized cell line, such as a mouse myeloma cell line. The resulting hybridomas can be screened for the production of antigen-specific antibodies (see, eg Example 3).

Hybridomas may be screened using standard methods, such as enzyme-linked immunosorbent assay (ELISA) and surface plasmon resonance (BIACORE), to identify hybridomas that produce an antibody that specifically binds to a particular autotransporter. Surface plasmon resonance may also be used to increase the efficiency of phage antibodies which bind to an epitope of an autotransporter.

Chimeric or humanized antibodies can be prepared based on the sequence of a murine monoclonal antibody. DNA encoding the heavy and light chain immunoglobulins can be obtained from the murine hybridoma of interest and engineered to contain non-murine (eg, human) immunoglobulin sequences using standard molecular biology techniques. For example, to create a chimeric antibody, the murine variable regions can be linked to human constant regions using methods known in the art. To create a humanized antibody, the murine CDR regions can be inserted into a human framework using methods known in the art (see, eg, U.S. Pat. Nos. 5,225,539; 5,530,101; 5,585,089; 5,693,762 and 6,180,370).

For antibodies expressed by hybridomas, DNA encoding the light and heavy chains of the antibody may be obtained by standard PCR amplification or DNA cloning techniques. For antibodies obtained from an immunoglobulin gene library (eg, using phage display techniques), nucleic acid encoding the antibody may be recovered from the library. Once DNA fragments encoding VH and VL segments are obtained, they may be manipulated by standard recombinant DNA techniques, for example, to convert the variable region genes to full-length antibody chain genes, to Fab fragment genes or to a scFv gene. In these manipulations, a VL- or VH-encoding DNA fragment may be linked to another DNA fragment encoding another protein, such as an antibody constant region or a flexible linker.

The isolated DNA encoding the VH region may be converted to a full-length heavy chain gene by linking the VH-encoding DNA to another DNA molecule encoding heavy chain constant regions (hinge, CH1, CH2 and/or CH3), the sequences of which for humans are known (see, eg, Kabat, E. A., el al. (1991) Sequences of Proteins of Immunological Interest, Fifth Edition, U.S. Department of Health and Human Services, NIH Publication No. 91-3242). The heavy chain constant region may be, for example, an IgG1, IgG2, IgG3, IgG4, IgA, IgE, IgM or IgD constant region. For a Fab fragment heavy chain gene, the VH-encoding DNA may be linked to another DNA molecule encoding only the heavy chain CH1 constant region. The isolated DNA encoding the VL region may also be used to express a full-length light chain gene (as well as a Fab light chain gene) by linking the VL-encoding DNA to another DNA molecule encoding the light chain constant region, CL.

To create a scFv gene, the VH- and VL-encoding DNA fragments may be linked to another fragment encoding a flexible linker such that the VH and VL sequences can be expressed as a contiguous single-chain protein, with the VL and VH regions joined by the flexible linker.

Humanized antibodies or fragments thereof may be generated by replacing sequences of the Fv variable domain that are not directly involved in antigen binding with equivalent sequences from human Fv variable domains. The humanized antibodies may be expressed from nucleic acid sequences that encode all or part of immunoglobulin Fv variable domains from at least one of a heavy or light chain. Such nucleic acids may be obtained from a hybridoma producing an antibody against a predetermined autotransporter, as well as from other sources. The recombinant DNA encoding the humanized antibody molecule can then be cloned into an appropriate expression vector.

Humanized antibodies may also be produced using transgenic animals (eg, mice) which are engineered to express human heavy and light chain genes, but are incapable of expressing endogenous mouse immunoglobulin heavy and light chain genes. All of the CDRs of a particular human antibody may be replaced with at least a portion of a non-human CDR, or only some of the CDRs may be replaced with non-human CDRs.

Antibodies of the present disclosure may also be produced in a host cell transfectoma using, for example, a combination of recombinant DNA techniques and gene transfection methods as is well known in the art (Morrison. Science. 1985, 229:1202).

Alternatively, antibodies and fragments can be synthesized using other DNA techniques well known in the art. For example, DNA molecules encoding an antibody fragment can be cloned into a suitable expression vector, which is then introduced into a suitable eukaryotic or prokaryotic host that will then express the fragment. Methods of producing humanized or chimeric antibodies or fragments using recombinant DNA techniques are also well known in the art. In certain embodiments, a chimeric antibody of the present disclosure is produced by obtaining nucleic sequences encoding the murine VL and VH domains, and constructing a chimeric antibody expression vector by inserting those nucleic acid sequences into an expression vector encoding human CH and CL. The expression vector may then be introduced into a suitable host cell.

Suitable host cells may include, for example, Chinese hamster ovary (CHO) cells, NSO, SP2 cells, HeLa cells, baby hamster kidney (BHK) cells, monkey kidney cells (COS), human hepatocellular carcinoma cells, A549 cells, 3T3 cells and HEK-293 cells among others. Mammalian host cells include human, mouse, rat, dog, monkey, pig, goat, bovine, horse and hamster cells. Other cell lines that may be used are insect cell lines, such as Sf9 cells, amphibian cells, bacterial cells, plant cells and fungal cells.

A variety of host-expression vector systems may be employed to express the antibodies and antigen binding proteins described herein. Suitable systems may include, for example, microorganisms such as bacteria (eg, *E. coli* and *B. subtilis*) transformed with recombinant bacteriophage DNA, plasmid DNA or cosmid DNA expression vectors comprising immunoglobulin coding sequences; yeast (eg, *Saccharomyces, Pichia*) transformed with recombinant yeast expression vectors comprising immunoglobulin coding sequences; insect cell systems infected with recombinant virus expression vectors (eg, baculovirus) comprising the immunoglobulin coding sequences; plant cell systems infected with recombinant virus expression vectors (eg, cauliflower mosaic virus and tobacco mosaic virus) or transformed with recombinant plasmid expression vectors (eg, using a Ti plasmid) comprising immunoglobulin coding sequences; or mammalian cell systems (eg, COS, CHO, BHK, 293, 293T, 3T3 cells, lymphotic cells) harbouring recombinant expression constructs.

Those skilled in the art will be familiar with various methods of producing antibody fragments. For example, a Fab may be produced by treating an antibody with papaine, or by expressing both chains of the Fab in a prokaryotic or eukaryotic cell. A F(ab')2 may be produced by treating an antibody with pepsin, or by binding Fab' via a thioether or a disulfide bond. On the other hand, a Fab' can be produced by treating F(ab')2 with a reducing agent such as dithiothreitol (DTT), or by expressing the Fab' chains in a prokaryotic or eukaryotic cell. An scFv may be produced by expressing the CDRs or VH and VL domains in a prokaryotic or eukaryotic cell. CDR grafting may also be employed to generate a humanised scFv fragment. A single chain antibody or VHH may be generated by immunising a Camelidae mammal with the target antigen (eg, the passenger domain of an autotransporter), taking a sample from the immunised Camelidae mammal and isolating heavy chain antibody sequences and/or VHH sequences directed against the target antigen. Single chain antibodies or VHH may also be produced by screening a library comprising heavy chain antibody sequences and/or VHH sequences. Other methods of producing antibody fragments will be well known by those skilled in the art.

Modified and Variant Antibodies

The antibodies and antigen binding proteins described herein may be engineered or modified to generate antibodies and antigen binding proteins having desirable properties in addition to their autotransporter binding capabilities, or to modify those capabilities. For example, the variable regions of an antibody may be engineered by CDR grafting. CDR grafting may be employed to generate humanized antibodies as described above. Because CDR sequences are responsible for most antibody-antigen interactions, it is possible to express recombinant antibodies that mimic the properties of specific reference antibodies by constructing expression vectors that include CDR sequences from the reference antibody grafted onto framework sequences from a different antibody having different properties.

Framework modifications may involve mutating one or more residues within the framework region, or even within one or more CDR regions, to remove T cell epitopes and thereby reduce the potential immunogenicity of the antibody. This approach is sometimes referred to as "deimmunization". In certain instances, it may be beneficial to mutate residues within the framework regions in order to maintain or enhance the antigen binding ability of an antibody. Framework sequences can be obtained from publicly available DNA databases or published references. For example, germline DNA sequences for human heavy and light chain variable region genes can be found in the VBASE human germline sequence database, as well as in: Kabat, E. A., et al. (1991) Sequences of Proteins of Immunological Interest, Fifth Edition, U.S. Department of Health and Human Services, NIH Publication No. 91-3242; Tomlinson, I. M., et al. J. Mol. Biol. 1992. 227:776-798; and Cox, J. P. L. et al. Eur. J. Immunol. 1994. 24:827-836.

An antibody may also be obtained from a non-human animal, and then modified, (eg, humanized, deimmunized, rendered chimeric) using recombinant DNA techniques which are known in the art. Examples of modified antibody constructs include humanized variants of non-human antibodies, affinity matured antibodies and antibody mutants having altered effector functions. Affinity maturation is the process by which B cells produce antibodies having increased affinity for an antigen during an immune response. With repeated exposures to the same antigen, a host may produce antibodies having greater affinities. In vitro affinity maturation has been employed to optimise antibodies and fragments thereof. Genetic diversity may be introduced by way of random mutagenesis within the CDRs using radiation, chemical mutagens or error-prone PCR. Genetic diversity may also be enhanced by chain shuffling. Two or three rounds of mutation and selection using display methods such as phage display may result in antibody fragments with increased affinities.

To identify candidate hypervariable region sites for modification, alanine scanning mutagenesis can be performed to identify residues which significantly contribute to antigen binding. Alternatively, or in addition, a crystal structure of the antigen-antibody complex may be analysed to identify contact points, which may be suitable candidates for substitution.

The antibodies of the present disclosure may also include chimeric antibodies wherein a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies. Chimeric antibodies can also include primitized antibodies comprising variable domain antigen-binding sequences derived from a non-human primate and human constant region sequences.

In further modifications, the antibodies and antigen binding proteins may have one or more methionine residues within the heavy and/or light chain CDRs replaced with amino acid residues that do not undergo oxidative degradation. In certain embodiments, it may be desirable to replace certain amino acids having exposed side-chains with alternative amino acids in order to provide greater chemical stability of the final antibody, and avoid deamidation or isomerization. The deamidation of asparagine may occur on NG, DG, NG, NS, NA, NT, QG or QS sequences, and result in the creation of an isoaspartic acid residue which can cause the polypeptide chain to kink and lose its stability (isoaspartic acid effect). In certain embodiments, an Asn residue may be changed to Gln or Ala to reduce the potential for formation of isoaspartate, particularly within a CDR. It may also be desirable to alter an amino acid adjacent to an asparagine or glutamine residue to reduce the likelihood of deamidation, which is more likely to occur when small amino acids occur adjacent to asparagine or glutamine. It may further be desirable to alter Asn-Pro combinations within a CDR to Gln-Pro, Ala-Pro or Asn-Ala in order to minimize potential scissile Asn-Pro peptide bonds. Antibodies with such substitutions may be subsequently screened to ensure that the substitutions do not decrease the affinity or specificity of the antibody.

Other desirable modifications to the antibodies described herein include modifications which selectively block antigen binding in tissues and environments where antigen binding might be detrimental, but allow antigen binding where it would be beneficial. In one embodiment, a blocking peptide mask is generated that specifically binds to the antigen binding surface of the antibody and interferes with antigen binding. The mask may be linked to each binding arm of the antibody by a peptidase cleavable linker. Masking ligands may comprise, or be derived from, the antigen to which the antibody is intended to bind, or may be independently generated.

There are five major classes, or isotypes, of heavy chain constant region (IgA, IgG, IgD, IgE and IgM), each with characteristic effector functions. These isotypes can be further subdivided into subclasses. IgG, for example, is separated into four subclasses known as IgG1, IgG2, IgG3 and IgG4. IgG molecules interact with three classes of Fcγ receptors (FcγR) specific for the IgG class of antibody, namely FcγRI, FcγRII and FcγRIII. The important sequences for the binding of IgG to the FcγR receptors are likely to be located in the CH2 and CH3 domains. The serum half-life of an antibody is influenced by the ability of that antibody to bind to the neonatal Fc receptor (Fc Rn). The antibodies and antigen binding proteins described herein may be engineered to include modifications within the Fc region to alter one or more properties of the antibody, such as complement fixation, serum half-life, Fc receptor binding or effector function. Furthermore, the antibodies and antigen binding proteins disclosed herein may also be chemically modified or be modified to alter their glycosylation. The antibodies of the present disclosure may comprise the variable domains or CDR sequences of the antibodies and antigen binding proteins described herein combined with constant domains comprising different Fc regions, selected based on the biological activities (if any) of the antibody for the intended use (Salfeld, Nat. Biotech. 2007. 25: 1369). In certain embodiments, sites that affect binding to Fc receptors may be removed. In other embodiments, an Fc region may be modified to remove an antigen-dependent cellular cytotoxicity (ADCC) site or to reduce complement dependent cytotoxicity (CDC).

To avoid effector function altogether, IgG4 antibodies may be used. Alternatively, antibodies or fragments lacking an Fc region or a substantial portion thereof may be generated. Another approach to avoid effector function may be to mutate the Fc region in order to eliminate glycosylation. For example, glycosylation is known to occur at motifs containing an asparagine-X-serine or asparagine-X-threonine sequence, where X is any amino acid (although not typically proline). The Fc region may also be altered by replacing at least one amino acid residue with a different amino acid residue and thereby reduce effector functions of the antibody. On the other hand, it may be desirable in certain circumstances to increase effector function. In that regard, the Fc region may be modified to increase ADCC and/or to increase the affinity for an Fcγ receptor by modifying one or more amino acids. The Fc region may also be modified to increase CDC activity.

The antibodies described herein may also be modified to increase their biological half-life. For example, the half-life of an antibody may be improved by increasing the binding affinity of the Fc region for FcRn. The antibody may also be altered within the CH1 or CL region to contain a salvage receptor binding epitope taken from two loops of a CH2 domain of an Fc region of an IgG (see, eg, U.S. Pat. Nos. 5,869,046 and 6,121,022). Stabilising modifications have been also described, for example, in Yeung et al. J. Immunol. 2010. 182: 7663-7671; WO 97/34631; WO 02/060919; WO 14/043344 Zalevsky et al. Nat. Biotechnol. 2010. 28: 157; Labrijn et al. Nat. Biotech. 2009. 27:767; Reddy et al. J. Immunol. 2000. 164:1925 and Petkova et al. Int. Immunol. 2006. 18:1759.

The half-life of the antibodies of the present disclosure may also be increased by pegylation. To that end, the antibody or fragment may be reacted with a polyethylene glycol (PEG) reagent, such as a reactive ester or aldehyde derivative of PEG, under conditions wherein one or more PEG groups attach to the antibody or fragment. Pegylation may be carried out via an acylation reaction or an alkylation reaction with a reactive PEG molecule or an analogous reactive water-soluble polymer.

Variant antibodies or antigen binding proteins of the present disclosure may contain conservative amino acid substitutions at various locations relative to a parent antibodies or antigen binding proteins. A "conservative amino acid substitution" is one in which the amino acid residue is replaced with an amino acid residue having a similar side chain. Those skilled in the art will understand that different amino acids can be grouped based on the properties of their side chains. Such groupings are set out below.

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (eg, histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (ie, glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

Certain amino acids may also be characterized as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. For the purposes of the present disclosure, however, proline is considered to be a "small" amino acid.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 1.

TABLE 1

Amino acid sub-groupings

| SUB-GROUP | AMINO ACIDS |
|---|---|
| Acidic | Aspartic acid (D), Glutamic acid (E) |
| Basic | Noncyclic: Arginine (R), Lysine (K); Cyclic: Histidine (H) |
| Charged | Aspartic acid (D), Glutamic acid (E), Arginine (R), Lysine (K), Histidine (H) |
| Small | Glycine (G), Serine (S), Alanine (A), Threonine (T), Proline (P) |
| Nonpolar/neutral | Alanine (A), Glycine (G), Isoleucine (I), Leucine (L), Methionine (M), Phenylalanine (F), Proline (P), Tryptophan (W), Valine (V) |
| Polar/neutral | Asparagine (N), Histidine (H), Glutamine (Q), Cysteine (C), Serine (S), Threonine (T), Tyrosine (Y) |
| Polar/negative | Aspartic acid (D), Glutamic acid (E) |
| Polar/positive | Lysine (K), Arginine (R) |
| Polar/large | Asparagine (N), Glutamine (Q) |
| Polar | Arginine (R), Asparagine (N), Aspartic acid (D), Cysteine (C), Glutamic acid (E), Glutamine (Q), Histidine (H), Lysine (K), Serine (S), Threonine (T), Tyrosine (Y) |
| Hydrophobic | Tyrosine (Y), Valine (V), Isoleucine (I), Leucine (L), Methionine (M), Phenylalanine (F), Tryptophan (W) |
| Aromatic | Tryptophan (W), Tyrosine (Y), Phenylalanine (F) |
| Residues that influence chain orientation | Glycine (G) and Proline (P) |

Conservative amino acid substitutions are also grouped based on amino acid side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change alters the activity or specificity of an antibody or antigen binding protein can readily be determined using known binding assays. Conservative substitutions are shown in Table 2 under the heading of exemplary and preferred substitutions.

TABLE 2

Exemplary amino acid substitutions

| ORIGINAL RESIDUE | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |

TABLE 2-continued

Exemplary amino acid substitutions

| ORIGINAL RESIDUE | EXEMPLARY SUBSTITUTIONS | PREFERRED SUBSTITUTIONS |
|---|---|---|
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G. *Biochemistry*, third edition, Wm. C. Brown Publishers (1993).

The antibodies and antigen binding proteins described herein may also comprise other modifications such as amino acids with modified side chains, incorporation of unnatural amino acid residues and/or their derivatives during peptide, polypeptide or protein synthesis and the use of cross-linkers and other methods which impose conformational constraints. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS). The carboxyl group may be modified by carbodiimide activation via O-acylisourea formation followed by subsequent derivatization, by way of example, to a corresponding amide. The guanidine group of arginine residues may be modified by formation of heterocyclic condensation products with reagents such as 2,3-butanedione, phenylglyoxal and glyoxal. Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH. Tryptophan residues may be modified, for example, by alkylation of the indole ring with 2-hydroxy-5-nitrobenzyl bromide or sulphonyl halides or by oxidation with N-bromosuccinimide. Tyrosine residues may be modified by nitration with tetranitromethane to form a 3-nitrotyrosine derivative. The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present disclosure is shown in Table 3.

TABLE 3

Non-conventional amino acids
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlyserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamyledyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

Binding Assays

The antibodies and antigen binding proteins described herein may be tested for their binding affinity to an autotransporter by various techniques that are known in the art. For example, an ELISA may be performed wherein microtiter plates are coated with purified autotransporter or the passenger domain of an autotransporter. Dilutions of the antibody (eg, dilutions of plasma from autotransporter-immunized mice) may then be added to each well and incubated. The plates may then be washed and then incubated with secondary reagent. After washing, the plates may be developed with a detectable substrate and analysed. Sera from immunized mice may then be further screened by flow cytometry for binding to a cell line expressing the autotransporter, but not to a control cell line that does not express the autotransporter.

An ELISA assay as described above can be used to screen for antibodies and hybridomas that produce anti-autotransporter antibodies. Hybridomas that produce antibodies that bind, preferably with high affinity, to the autotransporter can then be subcloned and further characterized. One clone from each hybridoma, which retains the reactivity of the parent cells (by ELISA), can then be chosen for making a cell bank, and for antibody purification.

ELISA (as well as various other techniques known in the art) may also be used to determine the affinity of an antibody to a target antigen. Affinity can also be determined by a surface plasmon resonance (SPR) assay (see, eg, Example 7). Using this methodology, the association rate constant ($k_a$ in $M^{-1}s^{-1}$) and the dissociation rate constant ($k_d$ in $s^{-1}$) can be measured. The equilibrium dissociation constant ($K_D$ in M) can then be calculated from the ratio of the kinetic rate constants ($k_d/k_a$). In some embodiments, affinity is determined by a kinetic method, such as a Kinetic Exclusion Assay (KinExA) (see, eg, Rathanaswami et al. Analyt. Biochem. 2008. 373:52-60). Using a KinExA assay, the equilibrium dissociation constant and the association rate constant can be measured, and the dissociation rate constant can be calculated from these values ($K_D \times k_a$). In other embodiments, affinity is determined by an equilibrium/solution method.

The dissociation constant may also be measured, for example, using a radioimmunoassay (RIA). For example, an RIA may be performed with the Fab fragment and its antigen.

In some embodiments, the antibody or antigen binding protein of the present disclosure binds to the autotransporter with a $K_D$ of about 100 nM or less. In some embodiments, the antibody or antigen binding protein binds to the autotransporter with a $K_D$ of about 50 nM or less. In some embodiments, the antibody or antigen binding protein binds to the autotransporter with a $K_D$ of about 20 nM or less such as about 15 nM or less, or about 14 nM or less, or about 13 nM or less, or about 12 nM or less, or about 11 nM or less, or about 10 nM or less, or about 9 nM or less, or about 8 nM or less, or about 7 nM or less. In some embodiments, the antibody or antigen binding protein binds to the autotransporter with a $K_D$ of about 1 nM or less. In some embodiments, the antibody or antigen binding protein binds to autotransporter with a $K_D$ of about 0.5 nM or less. In some embodiments, the antibody or antigen binding protein binds to the autotransporter with a $K_D$ of about 0.1 nM or less. In some embodiments, the antibody or antigen binding protein binds to the autotransporter with a $K_D$ of about 0.01 nM to 100 nM, about 0.01 nM to 10 nM, about 0.01 nM to 5 nM, about 0.01 nM to 1 nM, about 0.01 to 0.5 nM, about 0.01 nm to 0.1 nM, about 0.01 nm to 0.05 nM, about 0.05 nM to 100 nM, about 0.05 nM to 10 nM, about 0.05 nM to 5 nM, about 0.05 nM to 1 nM, about 0.05 to 0.5 nM, about 0.05 nm to 0.1 nM, about 0.1 nM to 100 nM, about 0.1 nM to 10 nM, about 0.1 nM to 5 nM, about 0.1 nM to 1 nM, about 0.1 to 0.5 nM, about 0.5 nM to 100 nM, about 0.5 nM to 10 nM, about 0.5 nM to 5 nM, about 0.5 nM to 1 nM, about 1 nM to 100 nM, about 1 nM to 10 nM, about 2 nM to 10 nM, about 3 nM to 10 nM, about 5 nM to 10 nM, or about 5 nM to 8 nM.

Competitive Binding

Antibodies that compete for binding with the antibodies and antigen binding proteins described herein, such as Fab7D10 and Fab10C12, may be raised using immunization protocols similar to those described herein (see, eg, Example 3). Antibodies that compete for binding with the antibodies and antigen binding proteins described herein may also be generated by immunizing mice with the relevant autotransporter or a fragment of the autotransporter such as its passenger domain, or a fragment comprising an epitope bound by the antibodies and antigen binding proteins described herein. The resulting antibodies can be screened for their ability to inhibit binding of the antibodies and antigen binding proteins described herein (eg, Fab7D10 or Fab10C12) to the autotransporter using methods well known in the art, for example by blocking binding to the autotransporter, or a domain thereof in an ELISA, or blocking the ability to bind to cells expressing the autotransporter on their surface, eg, by FACS. In certain embodiments, an antibody competes with, and inhibits binding of another antibody to a target by at least about 10%, about 20%, about 30%, about 40%, about 50%, about 60%, about 70%, about 80%, about 90%, about 99% or more.

Those skilled in the art will understand that it is possible to determine, without undue burden or experimentation, if an antibody has the same specificity as an antibody or antigen binding protein described herein by ascertaining whether the former prevents the latter from binding to the target. If the antibody being tested competes with the antibody of the disclosure, as shown by a decrease in binding by the antibody of the disclosure, then the two antibodies bind to the same, or a closely related, epitope. An alternative method for determining whether an antibody has the specificity of an antibody described herein is to pre-incubate the antibody described herein with the target autotransporter and then add the antibody being tested to determine if the antibody being tested is inhibited in its ability to bind the target autotransporter. If the antibody being tested is inhibited then it is likely to have the same, or functionally equivalent, epitopic specificity as the antibody of the disclosure.

Whether two antibodies compete with each other for binding to a target may be determined using known competition experiments, for example: solid phase direct or indirect RIA, solid phase direct or indirect enzyme immunoassay (EIA), sandwich competition assay (see, eg, Stahli et al. Meth. Enz. 1983. 92:242-253; Morel et al. Molec. Immunol. 1988. 25:7-15), solid phase direct biotin-avidin EIA (see, eg, Kirkland et al. J. Immunol. 1986. 137:3614-3619; Cheung, et al. 1990. Virology 176:546-552), solid phase direct labelled assay, solid phase direct labelled sandwich assay (see, eg, Harlow and Lane. 1988. Antibodies, A Laboratory Manual, Cold Spring Harbor Press), and direct labelled RIA (Moldenhauer et al. 1990. Scand. J. Immunol. 32:77-82). Typically, such an assay involves the use of purified antigen bound to a solid surface or cells bearing either of these, an unlabelled test antibody or antigen binding protein and a labelled reference antibody or antigen binding protein. For example, standard ELISA assays or competitive ELISA assays can be used wherein a target antigen (eg, an autotransporter or the passenger of an autotransporter) is immobilized on a plate. Various concentrations of unlabelled test antibody are then added, and the plate is washed. Labelled reference antibody is subsequently added, washed, and the amount of bound label is measured. If the increasing concentration of the unlabelled test antibody inhibits the binding of the labelled reference antibody, the test antibody is said to inhibit the binding of the reference antibody to the target on the plate, or is said to compete with the binding of the reference antibody. Additionally or alternatively, BIACORE® SPR analysis may be used to assess the ability of the antibodies to compete.

In a preferred assay, the binding affinity of a test antibody and a reference or control antibody or fragment thereof (eg, Fab7D10 or Fab10C12) is first determined using a Biacore T200 biosensor instrument (see, eg, Example 7). For example, the antibody is immobilized onto a CM5 chip at a level of 500-1000 RU using amine coupling. SPR experiments are then performed at 25° C. using HBS-EP (10 mM HEPES, pH 7.4, 150 mM NaCl, 3.4 mM EDTA, and 0.005% P20) as the running buffer. To generate binding data, an autotransporter or its passenger domain (eg, Ag43a$^\alpha$) at concentrations ranging from 15.6 nM to 1000 nM is injected over the immobilized antibody at a constant flow rate of 90 mL/min for 230 s; autotransporter dissociation is monitored by flowing running buffer at 90 mL/min for 600 s. The surface may be regenerated after each cycle by injecting 10 mM glycine/HCl at pH 2.0. Kinetic analysis may then be carried out using the Biacore T200 evaluation software. In performing the competition assay, the antibody or fragment with the weaker $K_D$ is captured on a CM5 chip at a level of 500 RU using amine coupling. Competition assays may then be performed using a co-inject strategy, wherein the autotransporter or its passenger domain (eg, Ag43a$^\alpha$) is injected at a constant concentration (approximately 60 nM), followed immediately by the second antibody or fragment as a 2-fold dilution series, cycle-to-cyle. A concentration of $10 \times K_D$ may be used for the antibody or fragment analyte. Kinetic assays may be carried out using a Biacore T200. If the two antibodies or fragments thereof bind the same or overlapping epitopes, increasing concentrations of the antibody or fragment analyte will block autotransporter binding.

Inhibition may be expressed as an inhibition constant (K) or as $IC_{50}$ which is the concentration of test antibody that yields a 50% reduction in binding of the reference antibody.

In some examples, the present disclosure provides an antibody or antigen binding fragment that competes with a reference antibody or antigen binding fragment for binding to Ag43a, wherein the reference antibody or antigen binding fragment comprises: a) a heavy chain comprising the sequence set forth in SEQ ID NO: 13 and a light chain comprising the sequence set forth in SEQ ID NO: 14; or b) a heavy chain comprising the sequence set forth in SEQ ID NO: 25 and a light chain comprising the sequence set forth in SEQ ID NO: 26.

Antibodies that Bind to the Same Epitope

Antibodies that bind to the same or similar epitopes as the antibodies and antigen binding proteins described herein may be raised using immunization protocols similar to those described herein (see, eg, Example 3). Epitope determinations may be performed using methods similar to those described herein (see, eg, Example 11) as well as other methods known by those skilled in the art.

Techniques for determining whether antibodies bind to the same epitope as the antibodies and antigen binding proteins described herein include, for example, epitope mapping methods, such as immunoblotting and immunoprecipitation assays, wherein overlapping or contiguous peptides of an antigen are tested for reactivity with a given antibody or antigen binding protein, 2-dimensional nuclear magnetic resonance and x-ray crystallography of antigen: antibody complexes, which provides atomic resolution of the epitope, and hydrogen/deuterium exchange mass spectrometry (HDX-MS). Other methods monitor the binding of the antibody to antigen fragments (eg, proteolytic fragments) or to mutated variations of the antigen in which loss of binding due to mutation of an amino acid residue within the antigen sequence is often considered an indication that the amino acid forms part of the epitope component, such as in alanine scanning mutagenesis or yeast display of mutant target sequence variants. Methods may also rely on the ability of an antibody or antigen binding fragment of interest to affinity isolate specific short peptides (either in native three dimensional form or in denatured form) from combinatorial phage display peptide libraries, or from a protease digest of the target protein. The peptides are then regarded as leads for the definition of the epitope corresponding to the antibody used to screen the peptide library. In addition, computational combinatorial methods for epitope mapping may also be used. These methods may rely on the ability of the antibody of interest to affinity isolate specific short peptides from combinatorial phage display peptide libraries. Antibodies having the same or closely related VH and VL or the same CDR sequences are expected to bind to the same epitope.

In some examples, the present disclosure provides an antibody or antigen binding fragment that binds to the same epitope of Ag43a as a reference antibody or antigen binding fragment wherein the reference antibody or antigen binding fragment comprises: a) a heavy chain comprising the sequence set forth in SEQ ID NO: 13 and a light chain comprising the sequence set forth in SEQ ID NO: 14; or b) a heavy chain comprising the sequence set forth in SEQ ID NO: 25 and a light chain comprising the sequence set forth in SEQ ID NO: 26.

Binding Molecules

As described herein, the present inventors have discovered a conserved mechanism by which autotransporters homodimerise and promote bacterial aggregation and biofilm formation. The inventors have applied this discovery and developed autotransporter-binding molecules which block the homodimerisation of autotransporters and thereby reduce bacterial aggregation and biofilm formation. The present inventors have developed several antibodies and antibody fragments that block autotransporter homodimerisation, but it will be appreciated by those skilled in the art that autotransporter homodimerisation may be blocked using other binding molecules. The binding molecule may, for example, be a macromolecule or a small molecule, either of which may be effective at preventing self-association between autotransporter molecules. A small molecule is generally a small organic compound having low molecular weight such as less than 5000 Daltons, less than 4000 Daltons, less than 3000 Daltons, less than 2000 Daltons or less than 1000 Daltons. Inhibitors may be identified by screening a combinatorial library containing a large number of potentially effective molecules. Such combinatorial chemical libraries can be screened in one or more assays to identify those library members (particular chemical species or subclasses) that display a desired characteristic activity such as inhibiting self-association between autotransporter molecules or bacterial aggregation. The molecules thus identified can serve as conventional "lead compounds" or can themselves be used to inhibit bacterial aggregation.

Preparation and screening of combinatorial chemical libraries is well known to those of skill in the art. Such combinatorial chemical libraries include, but are not limited to, peptide libraries (see, eg, U.S. Pat. No. 5,010,175; Furka, Int. J. Pept. Prot. Res. 1991. 37:487-493 and Houghton et al. Nature, 1991. 354:84-88) and carbohydrate libraries (see, eg, Liang et al. Science, 1996. 274:1520-1522 and U.S. Pat. No. 5,593,853). Other chemistries for generating diverse chemical libraries can also be used, for example, peptoids (see, eg, WO 91/19735), encoded peptides (see, eg, WO 93/20242), random bio-oligomers (see, eg, WO 92/00091), benzodiazepines (see, eg, U.S. Pat. No. 5,288,514), diversomers such as hydantoins, benzodiazepines and dipeptides (see, eg, Hobbs et al., Proc. Nat. Acad. Sci. 1993. USA 90: 6909-6913), vinylogous polypeptides (see, eg, Hagihara et al., J. Amer. Chem. Soc. 1992. 114:6568), nonpeptidal peptidomimetics with β-D-glucose scaffolding (see, eg, Hirschmann et al., J. Amer. Chem. Soc. 1992. 114:9217-9218), analogous organic syntheses of small compound libraries (see, eg, Chen et al., J. Amer. Chem. Soc. 1994. 116:2661), oligocarbamates (see, eg, Cho et al., Science 1993. 261:1303), and/or peptidyl phosphonates (see, eg, Campbell et al., J. Org. Chem. 1994. 59:658), nucleic acid libraries (see, eg, Ausubel et al., eds., Current Protocols in Molecular Biology (1994); Sambrook and Russell, Molecular Cloning, A Laboratory Manual, 3rd ed. 2001), peptide nucleic acid libraries (see, eg, U.S. Pat. No. 5,539,083), antibody libraries (see, eg, Vaughn et al., Nat. Biotech. 1996. 14(3):309-314 and PCT/US96/10287), small organic molecule libraries (see, eg, Baum C&EN, Jan. 18, (1993); U.S. Pat. Nos. 5,569,588; 5,549,974; 5,525,735; 5,519,134; 5,506,337; 5,288,514).

Other suitable binding molecules may include peptide analogs. Peptide analogs are commonly used in the pharmaceutical industry as non-peptide drugs with properties analogous to those of the reference or template peptide. These types of non-peptide compounds are sometimes referred to as "peptide mimetics" or "peptidomimetics", and they are often developed with the aid of computerized molecular modelling. Generally, peptidomimetics are structurally similar to a paradigm polypeptide (eg, a polypeptide that has a biochemical property such as a binding capability), such as a human antibody, but have one or more peptide linkages optionally replaced by a linkage such as: —$CH_2NH$—, —$CH_2S$—, —$CH_2$—$CH_2$—, —CH=CH- (cis and trans), —$COCH_2$—, —$CH(OH)CH_2$—, or —$CH_2SO$—, by methods known in the art. Systematic substitution of one or more amino acids of a consensus sequence with a D-amino acid of the same type (eg, D-lysine in place of L-lysine) may be used to generate more stable peptides. In addition, constrained peptides comprising a consensus sequence or a substantially identical consensus sequence variation may be generated by methods known in the art (see, eg, Rizo and Gierasch, Ann. Rev. Biochem., 1992. 61:387), for example, by adding internal cysteine residues capable of forming intramolecular disulfide bridges which cyclize the peptide.

Small RNAs, antisense RNAs and other regulatory RNA molecules may also be engineered to target, and reduce the expression of, bacterial genes or their transcripts including those coding for an autotransporter (se, eg, Song et al. Biotech. J. 2015. 10(1): 56-68; Kang et al. Appl. Micriobiol. Biotechnol. 2014. 98(8): 3413-24; Gottesman and Storz. Cold Spring Harb. Perspect. Biol. 2011. 3(12) a003798).

In preferred examples, the binding molecule of the present disclosure is an antibody or an antigen binding fragment thereof. The antibody may be, for example, a monoclonal antibody, a polyclonal antibody, a multispecific antibody, a humanised antibody, a fully human antibody, a chimeric antibody, a single domain antibody, an immunoglobulin new antigen receptor (NAR), a camelid antibody or a nanobody. In some examples, the antibody or antigen binding fragment is a diabody (see, eg, EP 404,097; WO 93/11161; and Hollinger et al, Proc. Natl. Acad. Sci. USA. 1993. Vol. 90: 6444-6448), an intrabody, a domain antibody (single VL or VH domain or two or more VH domains joined by a peptide linker; see, eg, Ward et al, Nature. 1989. Vol. 341:544-546), a maxibody (2 scFvs fused to Fc region, see, eg, Fredericks et al. Prot. Eng. Des. Sel. 2004. 17:95-106; and Powers et al. J. Immunol. Meth. 2001. 251: 123-135), a triabody, a tetrabody, a minibody (scFv fused to CH3 domain; see, eg, Olafsen et al. Prot. Eng. Des. Sel. 2004. 17:315-23), a peptibody (one or more peptides attached to an Fc region, see, eg, WO 00/24782), a linear antibody (a pair of tandem Fd segments (VH-$CH_1$-VH-$CH_1$) which, together with complementary light chain polypeptides, form a pair of antigen binding regions, see, eg, Zapata et al., Protein Eng., Vol. 8: 1057-1062, 1995), a small modular immunopharmaceutical (see, eg, U.S. Patent Publication No. 20030133939), an immunoglobulin fusion protein (e.g. IgG-scFv, IgG-Fab, 2scFv-IgG, 4scFv-IgG, VH-IgG, IgG-VH, and Fab-scFv-Fc; see, eg, Spiess et al, Mol. Immunol., Vol. 2015. 67(2 Pt A):95-106), a Fab, a Fab', a F(ab')$_2$, a Fd, a scFv, a scAb or a dAb. In some examples, the binding molecule is a Designed Ankyrin Repeat Protein (DARPin), an affimer, an alphabody or an i-body. Those skilled in the art will understand that other types of binding molecules, including other types of antibodies and antigen binding fragments, may be used in accordance with the present disclosure.

In some examples, the present disclosure provides an isolated antibody or antigen binding fragment thereof that specifically binds to an autotransporter adhesin. Preferably, the antibody or antigen binding fragment binds to a passenger domain of the autotransporter adhesin. The antibody or antigen binding fragment is preferably a monoclonal antibody or antigen binding fragment thereof. The antibody or antigen binding fragment may bind to the autotransporter adhesin with a $K_D$ of less than about 10 nM, such as less than about 8 nM.

In certain examples, the antibody or antigen binding fragment may comprise a CDRH3 comprising the sequence set forth in SEQ ID NO: 5, and/or a CDRL3 comprising the sequence set forth in SEQ ID NO: 8. The antibody or antigen binding fragment may comprise a CDRH3 comprising the sequence set forth in SEQ ID NO: 17, and/or a CDRL3 comprising the sequence set forth in SEQ ID NO: 20.

In some examples, the antibody or antigen binding fragment thereof comprises:
  a) a VH comprising the sequence set forth in SEQ ID NO: 9 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 9; and
    a VL comprising the sequence set forth in SEQ ID NO: 10 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 10; or
  b) a VH comprising the sequence set forth in SEQ ID NO: 21 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 21; and
    a VL comprising the sequence set forth in SEQ ID NO: 22 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 22.

In some examples, the antibody or antigen binding fragment thereof comprises:
  a) a VH comprising the sequence set forth in SEQ ID NO: 9 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 9, wherein the VH comprises a CDRH3 comprising the sequence set forth in SEQ ID NO: 5; and
  b) a VL comprising the sequence set forth in SEQ ID NO: 10 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 10, wherein the VL comprises a CDRL3 comprising the sequence set forth in SEQ ID NO: 8.

In some examples, the antibody or antigen binding fragment thereof comprises:
  a) a VH comprising the sequence set forth in SEQ ID NO: 9 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 9, wherein the VH comprises a CDRH1 comprising the sequence set forth in SEQ ID NO: 3, a CDRH2 comprising the sequence set forth in SEQ ID NO: 4 and a CDRH3 comprising the sequence set forth in SEQ ID NO: 5; and b) a VL comprising the sequence set forth in SEQ ID NO: 10 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 10, wherein the VL comprises a CDRL1 comprising the sequence set forth in SEQ ID NO: 6, a CDRL2 comprising the sequence set forth in SEQ ID NO: 7 and a CDRL3 comprising the sequence set forth in SEQ ID NO: 8.

In some examples, the antibody or antigen binding fragment thereof comprises:

a) a VH comprising the sequence set forth in SEQ ID NO: 21 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 21, wherein the VH comprises a CDRH3 comprising the sequence set forth in SEQ ID NO: 17; and b) a VL comprising the sequence set forth in SEQ ID NO: 22 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 22, wherein the VL comprises a CDRL3 comprising the sequence set forth in SEQ ID NO: 20.

In some examples, the antibody or antigen binding fragment thereof comprises: a) a VH comprising the sequence set forth in SEQ ID NO: 21 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 21, wherein the VH comprises a CDRH1 comprising the sequence set forth in SEQ ID NO: 15, a CDRH2 comprising the sequence set forth in SEQ ID NO: 16 and a CDRH3 comprising the sequence set forth in SEQ ID NO: 17; and b) a VL comprising the sequence set forth in SEQ ID NO: 22 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 22, wherein the VL comprises a CDRL1 comprising the sequence set forth in SEQ ID NO: 18, a CDRL2 comprising the sequence set forth in SEQ ID NO: 19 and CDRL3 comprising the sequence set forth in SEQ ID NO: 20.

In some examples, the antibody or antigen binding fragment thereof comprises:

a) a heavy chain comprising the sequence set forth in SEQ ID NO: 13 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 13; and a light chain comprising the sequence set forth in SEQ ID NO: 14 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 14; or b) a heavy chain comprising the sequence set forth in SEQ ID NO: 25 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 14; and a light chain comprising the sequence set forth in SEQ ID NO: 26 or a sequence having at least about 50% identity, or at least about 60% identity, or at least about 65% identity, or at least about 70% identity, or at least about 75% identity, or at least about 80% identity, or at least about 85% identity, or at least about 90% identity, or at least about 91% identity, or at least about 92% identity, or at least about 93% identity, or at least about 94% identity, or at least about 95% identity, or at least about 96% identity, or at least about 97% identity, or at least about 98% identity, or at least about 99% identity to SEQ ID NO: 26.

In some examples, the present disclosure provides an isolated antibody or antigen binding fragment thereof that binds to a Type Va autotransporter. In some examples, the present disclosure provides an isolated antibody or antigen binding fragment thereof that binds to Ag43$^{\alpha}$ (SEQ ID NO: 1) at an epitope comprising one or more residues selected from the group consisting of N83, R113, N114, D133, N150, T151, T152, G169, R254, E270, T291, T310, R330, G332, A333, S335, T361, N362, R364, T380, T381, S383, N386, S399, T401, D404 and G405. In certain examples, the present disclosure provides an isolated antibody or antigen binding fragment thereof that binds to one or more residues selected from the group consisting of R330, G332, A333, S335, T361, N362, R364, T380, T381, S383, N386, S399, T401, D404 and G405 of Ag43a (SEQ ID NO: 1). In certain examples, the present disclosure provides an isolated antibody or antigen binding fragment thereof that binds to one or more amino acid residues within amino acids 330 to 405 of Ag43a (SEQ ID NO: 1). In certain examples, the present disclosure provides an isolated antibody or antigen binding fragment thereof that binds to residues R330, G332, A333, S335, T361, N362, R364, T380, T381, S383, N386, S399, T401, D404 and G405 of Ag43a (SEQ ID NO: 1).

As described herein, the passenger domain of Ag43a was expressed and purified (Example 1), and then used to raise several monoclonal antibodies using hybridoma technology (Example 3). The monoclonal antibodies were shown to be effective at blocking autotransporter homodimerisation and inhibiting bacterial aggregation (Example 4, 6 and 9). Those skilled in the art will understand that monoclonal antibodies may be raised against the passenger domain of other autotransporters using a similar methodology. For example, the passenger domain of another autotransporter may be cloned with a tag such as a $His_6$-tag, expressed in E. coli and purified using the relevant tag. Antibodies may be raised against the purified passenger domain, for example, using hybridoma technology. Those skilled in the art will be aware of other techniques that may be used to raise antibodies, including techniques described herein. The ability of the raised antibodies to bind to the passenger domain may be assayed using a number of suitable techniques such as ELISA (see, eg, Example 3), SPR (see, eg, Example 7), bacterial aggregation assays (see, eg, Examples 4 and 6) or biofilm assays (see, eg, Example 9).

In that regard, the present disclosure provides an isolated monoclonal antibody or antigen-binding fragment thereof that binds to a passenger domain of an autotransporter. In some examples, the present disclosure provides an isolated monoclonal antibody or antigen-binding fragment thereof that binds to a passenger domain of a homodimerising autotransporter and thereby inhibits homodimerisation of the autotransporter. In some examples, the present disclosure provides an isolated monoclonal antibody or antigen-binding fragment thereof that binds to a passenger domain of a homodimerising autotransporter wherein the monoclonal antibody or fragment thereof binds to the passenger domain with a $K_D$ of less than about 10 nM and thereby inhibits homodimerisation of the autotransporter.

In certain examples, the present disclosure provides an isolated antibody or antigen binding fragment that specifically binds to a homodimerising autotransporter. The homodimerising autotransporter may be selected from the group consisting of Ag43, Ag43a, Ag43b, TibA, AIDA-I, AutA, PmpD, VacA, MisL, EhaA, EhaB, EhaC, EhaD, UpaC, UpaH, YcgV, Aata, IcsA, Fap2, RadD and YpjA. In certain examples, the present disclosure provides an isolated antibody or antigen binding fragment that specifically binds to an autotransporter selected from the group consisting of Ag43, Ag43a, Ag43b and TibA. In certain examples, the present disclosure provides an isolated antibody or antigen binding fragment that specifically binds to an autotransporter selected from the group consisting of Ag43 from E. coli strain UTI189 or EDL933, Ag43a from E. coli strain CFT073, Ag43b from E. coli strain CFT073 and TibA from E. coli strain H10407. In certain examples, the present disclosure provides an isolated antibody or antigen binding fragment that binds to one or more residues within amino acids 65 to 308 of Ag43. In certain examples, the present disclosure provides an isolated antibody or antigen binding fragment that binds to one or more residues within amino acids 81 to 308 of Ag43 from EDL933 (SEQ ID NO: 33). In certain examples, the present disclosure provides an isolated antibody or antigen binding fragment that binds to one or more residues selected from the group consisting of N81, N112, D131, S130, N148, T166, T185, G186, S214, D233, T252, N268, T289 and T308 of Ag43 from EDL933 (SEQ ID NO: 33). In certain examples, the present disclosure provides an isolated antibody or antigen binding fragment that binds to one or more residues within amino acids 65 to 189 of Ag43 from UTI189 (SEQ ID NO: 31). In certain examples, the present disclosure provides an isolated antibody or antigen binding fragment that binds to one or more residues selected from the group consisting of G65, G82, 184, N112, D131, T132, T150, N152 and N189 of Ag43 from UTI189 (SEQ ID NO: 31).

In certain examples, the present disclosure provides an isolated antibody or antigen binding fragment that binds to one or more residues within amino acids 133 to 359 of Ag43b from CFT073 (SEQ ID NO: 41). In certain examples, the present disclosure provides an isolated antibody or antigen binding fragment that binds to one or more residues selected from the group consisting of D133, N164, 8166, D183, S199, S217, D284, T340. N342 and T359 of Ag43b from CFT073 (SEQ ID NO: 41).

In certain examples, the present disclosure provides an isolated antibody or antigen binding fragment that binds to one or more residues within amino acids 118 to 597 of TibA from H10407 (SEQ ID NO: 35). In certain examples, the present disclosure provides an isolated antibody or antigen binding fragment that binds to one or more residues selected from the group consisting of T118, T137, S154, Y255, Y274, S275, T293, S294, N312, S313, D330, N331, S367, K388, D387, N406, G427, N565 and D597 of TibA from H10407 (SEQ ID NO: 35).

Antimicrobial Agents

The present disclosure provides antibodies and antigen binding proteins that bind to autotransporter adhesins and prevent or reduce bacterial aggregation. Disruption of bacterial aggregation may expose the bacteria, increasing their sensitivity to antibiotics. In that regard, the antibodies and antigen binding proteins of the present disclosure may be used in combination with an antibiotic agent. The antibiotic agent may be administered together with the antibody or antigen binding protein as a single composition or formulation, or each compound may be administered separately. The present disclosure also provides immunoconjugates comprising an antibody or antigen binding protein as described herein, conjugated to an agent, such as a detectable label or an antibiotic agent.

General classes of antibiotics include, for example, aminoglycosides, polyenes, nitroimidazole, rifamycins, bacitracin, beta-lactam antibiotics, cephalosporins, chloramphenicol, macrolides, lincosamides, penicillins, quinolones, rifampicin, glycopeptide, tetracyclines, trimethoprim and sulfonamides. Examples of suitable antimicrobial agents may include amoxicillin, augmentin, amoxicillin, ampicillin, azlocillin, flucloxacillin, mezlocillin, methicillin, penicillin G, penicillin V, cephalexin, cefazedone, cefuroxime, loracarbef, cemetazole, cefotetan, cefoxitin, ciprofloxacin, levaquin, and floxacin, tetracycline, doxycycline, or minocycline, gentamycin, amikacin, and tobramycin, clarithromycin, azithromycin, erythromycin, daptomycin, neomycin, kanamycin or streptomycin.

In certain embodiments, suitable antibiotic agents for use with the autotransporter-binding molecules described herein may include penicillin antibiotics, cephem antibiotics, macrolide antibiotics, tetracycline antibiotics, glycycycline antibiotics, fosfomycin antibiotics, aminoglycoside antibiotics, chelating agents and new quinolone antibiotics. Non-limiting examples of antimicrobial agents include nisin, epidermin, gallidennin, cinnamycin, duramycin, lacticin 481, amoxicillin, amoxicillin/clavulanic acid, ampicillin/sulbactam, penicillin, metronidazole, clindamycine, chlortetracycline, dcmeclocycline, oxytetracycline, amikacin, gentamicin, kanamycin, neomycin, netilmicin, streptomycin, tobramycin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, claforan, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, chloramphenicol, clofazimine, colistimethate, colistin, cycloserine, fosfomycin, furazolidone, methenamine, nitrofurantoin, pentamidine, rifabutin, rifampin, spectinomycin, tigecycline, trimethoprim, trimetrexate glucuronate, vancomycin, chlorhexidine and carbapenem antibiotics such as imipenem, cilastatin or ertapenem. According to some embodiments, the antibiotic agent is an antibiotic peptide.

Methods and Uses

The antibodies and antigen binding proteins of the present disclosure may be administered to a subject who has, or is at risk of developing, an infection, for example, as a consequence of a medical procedure. The medical procedure may be a surgical procedure such as an orthopedic surgical operation (eg, hip arthroplasty, knee arthroplasty, total joint replacement, trauma), a spine surgical operation, a surgical operation on a digestive system organ (eg, esophagus, stomach, small intestine, large intestine, rectum, colon, appendix, liver, pancreas, gallbladder, gastric ulcer) gastric cancer procedures, open gastric bypass, appendectomy, colectomy, cholecystectomy, vagotomy, an open biliary tract procedure, a small intestine procedure, a colorectal procedures, a cardiac procedure, hernia repair, a vascular procedure, a caesarian, prostatectomy, an obstetric and gynecologic surgical operation (eg, hysterectomy), head and neck cancer surgery, a transplantation surgery (eg, lung, liver, pancreas, kidney), neurosurgery (eg, deep brain stimulation implant) and a plastic surgery (eg, breast reconstruction, mastectomy). Treatments may be preoperative, intraoperative and/or postoperative.

The antibodies and antigen binding proteins of the present disclosure may be used to treat, or reduce the likelihood of, medical device related infections, orthopaedic implant infections, biliary stent related infections and catheter related infections. The antibodies and antigen binding proteins of the present disclosure may also be used to reduce bacterial aggregation or biofilm formation on personal care devices and medical devices such as contact lenses, prostheses, orthopaedic implants, stents, catheters or pacemakers. The antibodies and antigen binding proteins of the present disclosure may also be used to reduce bacterial aggregation or biofilm formation in an animal such as a cat, a dog, a bird or livestock such as a cow, a bull, a sheep, a lamb, a pig or poultry. The antibodies and antigen binding proteins of the present disclosure may also be used to reduce bacterial aggregation or biofilm formation in a veterinary clinic, a butcher or an abattoir. The antibodies and antigen binding proteins of the present disclosure may also be used to reduce bacterial aggregation or biofilm formation on food processing or manufacturing equipment. Those skilled in the art will be aware of other suitable applications for the presently described antibodies and antigen binding fragments.

In some examples, there is provided a method of treating a bacterial infection in a subject the method comprising administering to the subject an antibody or antigen binding fragment of the present disclosure. In some examples, there is provided a method of treating a bacterial infection in a subject the method comprising administering to the subject an antibody or antigen binding fragment of the present disclosure, wherein the antibody or antigen binding fragment is administered concurrently with an antibiotic agent such as an antibiotic agent described herein. The bacterial infection is preferably associated with bacterial aggregation, bacterial biofilm formation, or bacterial attachment to a surface such as the surface of a gastrointestinal tract, a urinary tract or a medical device. The infection may be, for example, a urinary tract infection, a respiratory tract infection, a gastrointestinal tract infection, a pulmonary infection, an anal infection, a urethral infection, a throat infection, a mouth infection, a medical device related infection, an orthopaedic implant infection, a biliary stent related infection or a catheter related infection. The infection may be associated with inflammatory bowel disease, Crohn's disease or pyelonephritis. In some examples, there is provided a method of treating an *E. coli* infection in a subject the method comprising administering to the subject an antibody or antigen binding fragment of the present disclosure, wherein the *E. coli* is selected from the group consisting of avian pathogenic *E. coli* (APEC), diffusely adhering *E. coli* (DAEC), enterohemorrhagic *E. coli* (EHEC), enteroaggregative *E. coli* (EAEC), enteroinvasive *E. coli* (EIEC), adherent-invasive *E. coli* (AIEC), enteroaggregative and haemorrhagic *E. coli* (EAHEC), neonatal meningitis *E. coli* (NMEC), enterotoxigenic *E. coli* (ETEC), shiga toxin-producing *E. coli* (STEC), enteropathogenic *E. coli* (EPEC) and uropathogenic *E. coli* (UPEC). The *E. coli* may be strain CFT073, UT1189, EDL933 or H10407. Other bacterial infections that may be treated using the antibodies and antigen binding proteins of the present disclosure include those caused by *Haemophilus, Salmonella, Neisseria, Shigella, Helicobacter, Bordetella, Chlamydia, Rickettsia, Actinobacillus* and *Fusobacterium*.

In certain embodiments, the antibodies and antigen binding proteins of the present disclosure may be used to treat a disease or disorder associated with biofilm formation or bacterial aggregation, for example, heart valve endocarditis, chronic nonhealing wounds such as venous ulcers and diabetic foot ulcers, ear and sinus infections, urinary tract infections, respiratory tract infections, gastrointestinal tract infections, necrotizing enterocolitis, short bowel syndrome, distal intestinal obstructive syndrome, pulmonary infections such as cystic fibrosis and chronic obstructive pulmonary disease, catheter associated infections, infections associated with prostheses, periodontal disease, gonorrhea, *chlamydia*, typhoid, dysentery, food poisoning, bacterial influenza, typhus, stomach ulcers, pertussis and pneumonia. Those skilled in the art will appreciate that other diseases and disorders associated with bacterial infections may be treated using the antibodies and antigen binding proteins of the present disclosure.

Autotransporter adhesins that have a natural tendency to homodimerise are referred to herein as homodimerising autotransporters. Homodimerising autotransporters may also be referred to as self-associating autotransporters (SAATs), and include, amonger others, Ag43, Ag43a, Ag43b, TibA, AIDA-I, AutA, PmpD, VacA, MisL, EhaA, EhaB, EhaC, EhaD, UpaC, UpaH, YcgV, Aata, IcsA, Fap2, RadD and YpjA. As described herein, homodimerisation between autotransporters enables bacteria to aggregate and form biofilms. Multiple autotransporters may homodimerise with each other leading to the formation of an aggregate of autotransporters. The present disclosure provides binding molecules such as antibodies and antigen binding fragments that bind to homodimerising autotransporter adhesins and thereby inhibit the formation of a homodimer. Those skilled in the art will be aware of various techniques that may be used to determine whether an autotransporter adhesin is a homodimerising autotransporter adhesin. Suitable techniques may include, for example, size exclusion chromatography coupled with multi-angle light scattering (SEC-MALS) or analytical ultracentrifugation. At a cellular level, homodimerisation (autoaggregation) of autotransporters may be inferred when bacteria which naturally aggregate fail to do so when the autotransporter is rendered non-functional, for example, by a genetic mutation.

In some examples, there is provided a method of inhibiting homodimerisation of two autotransporter molecules the method comprising contacting at least one of said two autotransporter molecules with an autotransporter-binding molecule wherein the autotransporter-binding molecule binds to the at least one autotransporter and thereby blocks homodimerisation of the two autotransporter molecules. In certain examples, there is provided a method of inhibiting autotransporter-mediated aggregation of two or more bacteria wherein the two or more bacteria express an autotransporter adhesin, the method comprising contacting one of the two or more bacteria with an autotransporter-binding molecule, wherein the autotransporter-binding molecule binds to the autotransporter adhesin and inhibits aggregation of the two or more bacteria.

As described herein, the present inventors have also demonstrated that autotransporters can mediate bacterial attachment to a surface. It will be understood that autotransporter-mediated attachment of a bacterium to a surface such as a cellular surface may be inhibited by contacting the bacterium with an autotransporter-binding molecule. The binding molecule may bind to the passenger domain of the autotransporter and block the interaction between the autotransporter and the surface. The binding molecule may, for example, be an antibody or antigen binding fragment thereof generated using the methods described herein (eg, Example 3). Preferably, the autotransporter-binding molecule binds to the passenger domain of the autotransporter. The autotransporter may be, for example, UpaB. In examples where the autotransporter is UpaB, the autotransporter-binding molecule may bind to one or more residues within a window of amino acids flanked by amino acid positions 116 and 375 of UpaB (SEQ ID NO. 43). In some examples, the autotransporter-binding molecule may bind to one or more amino acids selected from the group consisting of N116, D119, N146, E165, N175, N189, Q197, N200, Q203, D217, K245, D246, K256, D281, R310, N316, D336 and D375 of UpaB (SEQ ID NO. 43).

In some examples, the present disclosure provides a method of inhibiting autotransporter-mediated attachment of a bacterium to a surface the method comprising contacting the bacterium with an effective amount of an antibody or antigen binding fragment that binds to the autotransporter. The bacterium may be E. coli. The E. coli may be UPEC. The UPEC may be strain CFT073. The autotransporter may be UpaB. The surface may be a urinary tract. The antibody or antigen binding fragment may block an interaction between the autotransporter and a fibronectin or glycosaminoglycan on the surface.

In certain examples, the present disclosure provides a method of reducing autotransporter-mediated colonisation of a urinary tract by a bacterium in a subject the method comprising administering to the subject an autotransporter-binding molecule such as an antibody or antibody fragment. The bacterium may be E. coli. The E. coli may be UPEC. The UPEC may be strain CFT073. The autotransporter may be UpaB. The autotransporter-binding molecule may block an interaction between the autotransporter and a fibronectin or glycosaminoglycan in the urinary tract.

It will also be understood that autotransporter-mediated attachment of a bacterium to a surface such as a cellular surface may be inhibited by contacting the bacterium or the surface with an isolated, recombinant or synthesised autotransporter, or a fragment of an autotransporter. In such examples, the isolated, recombinant or synthesised autotransporter or fragment thereof competes for binding to the surface (eg, the cellular surface) with autotransporters that are produced by, and are attached to, the bacterium. Preferably, the isolated, recombinant or synthesised autotransporter, or fragment thereof, is the same as the bacterium's autotransporter. For example, the isolated, recombinant or synthesised autotransporter or fragment thereof may share at least about 60% amino acid sequence identity to the autotransporter produced by the bacterium, such as at least about 65% sequence identity, at least about 70% sequence identity, at least about 75% sequence identity, at least about 80% sequence identity, at least about 90% sequence identity, at least about 95% sequence identity, at least about 96% sequence identity, at least about 97% sequence identity, at least about 98% sequence identity, at least about 99% sequence identity or 100% sequence identity to the autotransporter produced by the bacterium. In preferred examples, the isolated, recombinant or synthesised autotransporter fragment is a passenger domain of the autotransporter.

Dosages

Dosages may vary with the type and severity of the condition to be treated, and may include single or multiple dosses. Specific dosage regimens may be adjusted over time according to the individual need and the professional judgment of the practitioner administering the composition. When administered to a human subject, the dosage regimen may vary depending on a variety of factors including the type and severity of infection or condition, the age, sex, weight or medical condition of the subject and the route of administration. In that regard, precise amounts of the antibody or antigen binding protein for administration will depend on the judgement of the practitioner.

The antibodies and antigen binding proteins described herein may be administered over a period of hours, days, weeks, or months, depending on several factors, including the severity of the infection or condition being treated, whether a recurrence is considered likely, etc. The administration may be constant, eg, constant infusion over a period of hours, days, weeks, months, etc. Alternatively, the administration may be intermittent, eg, once per day over a period of days, once per hour over a period of hours, or any other such schedule as deemed suitable.

Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, transcutaneous, intradermal, intramedullary delivery (eg, injection), as well as intrathecal, direct intraventricular, intravenous, intraperitoneal, intranasal, or intraocular delivery (eg, injection). For injection, the antibody or antigen binding protein may be formulated in an aqueous solution, suitably in physiologically compatible buffers such as Hanks' solution, Ringer's solution, or physiological saline buffer. For transmucosal administration, penetrants appropriate to the barrier to be permeated may be used in the formulation. Such penetrants are generally known in the art.

The compositions of the present disclosure may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are known by those skilled in the art and include, eg, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the antibody or antigen binding protein may be formulated readily using pharmaceutically acceptable carriers well known in the art into dosages suitable for oral administration such as tablets, pills, capsules, liquids, gels, syrups, slurries, suspensions and the like, for oral ingestion by a patient to be treated. Suitable carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions. Additionally, suspensions may be prepared as appropriate oily injection suspensions. Suitable lipophilic solvents or vehicles include fatty oils such as sesame oil or synthetic fatty acid esters such as ethyl oleate or triglycerides. Aqueous injection suspensions may contain substances that increase the viscosity of the suspension, such as sodium carboxymethyl cellulose, sorbitol, or dextran. Optionally, the suspension may also contain suitable stabilisers or agents that increase the solubility of the compounds to allow for the preparation of highly concentrated solutions.

Pharmaceutical preparations for oral use can be obtained by combining the active agent, such as an antibody or antigen binding protein, with solid excipients and processing the mixture of granules, after adding suitable auxiliaries, if desired, to obtain tablets or dragee cores. Suitable excipients may include fillers such as sugars, including lactose, sucrose, mannitol, or sorbitol; cellulose preparations such as maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The antibodies and antigen binding proteins described herein may be provided in particulate form. A variety of particles may be used such as liposomes, micelles, lipidic particles, ceramic/inorganic particles and polymeric particles, and may be selected from nanoparticles and microparticles. In some embodiments, the particles are biodegradable and biocompatible, and optionally are capable of biodegrading at a controlled rate. The particles can be made of a variety of materials. Both inorganic and organic materials may be used. Polymeric and non-polymeric materials such as fatty acids may be used. Other suitable materials include, but are not limited to, gelatin, polyethylene glycol, trehalulose, dextran and chitosan. Particles with degradation and release times ranging from seconds to months can be designed and fabricated, based on factors such as the particle material.

Compositions, Methods and Uses of the Disclosure

Composition 1. An isolated antibody or antigen binding fragment thereof comprising: a) a CDRH3 comprising the sequence set forth in SEQ ID NO: 5 or a CDRL3 comprising the sequence set forth in SEQ ID NO: 8; or b) a CDRH3 comprising the sequence set forth in SEQ ID NO: 17 or a CDRL3 comprising the sequence set forth in SEQ ID NO: 20.

Composition 2. The isolated antibody or antigen binding fragment of composition 1 comprising: a) a CDRH3 comprising the sequence set forth in SEQ ID NO: 5 and a CDRL3 comprising the sequence set forth in SEQ ID NO: 8; or b) a CDRH3 comprising the sequence set forth in SEQ ID NO: 17 and a CDRL3 comprising the sequence set forth in SEQ ID NO: 20.

Composition 3. The isolated antibody or antigen binding fragment of composition 1 or composition 2 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8, or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 4. The isolated antibody or antigen binding fragment of any one of compositions 1 to 3 comprising: a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8.

Composition 5. The isolated antibody or antigen binding fragment of any one of compositions 1 to 3 comprising: a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 6. An isolated antibody or antigen binding fragment thereof comprising: a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

Composition 7. The isolated antibody or antigen binding fragment of composition 6 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8, or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 8. The isolated antibody or antigen binding fragment of composition 6 or composition 7 comprising: a) a VH comprising the sequence set forth in SEQ ID NO: 9 and a VL comprising the sequence set forth in SEQ ID NO: 10; or b) a VH comprising the sequence set forth in SEQ ID NO: 21 and a VL comprising the sequence set forth in SEQ ID NO: 22.

Composition 9. The isolated antibody or antigen binding fragment of any one of compositions 6 to 8 comprising: a) a heavy chain comprising the sequence set forth in SEQ ID NO: 13 and a light chain comprising the sequence set forth in SEQ ID NO: 14; or b) a heavy chain comprising the sequence set forth in SEQ ID NO: 25 and a light chain comprising the sequence set forth in SEQ ID NO: 26.

Composition 10. An isolated antibody or antigen binding fragment thereof comprising:

a CDRH1 comprising the sequence set forth as formula (I)

$$YTFTX_1YWX_2X_3 \quad (I);$$

a CDRH2 comprising the sequence set forth as formula (II)

$$WIGNIX_4PX_5X_6GX_7X_8NY \quad (II);$$

a CDRH3 comprising the sequence set forth as formula (III)

$$RX_9GX_{10}X_{11}RAMDY \quad (III);$$

a CDRL1 comprising the sequence set forth as formula (IV)

$$QSVX_{12}X_{13}DVA \quad (IV);$$

a CDRL2 comprising the sequence set forth as formula (V)

$$LLIX_{14}X_{15}X_{16}SNRX_{17}T \quad (V); \text{ and}$$

a CDRL3 comprising the sequence set forth as formula (VI)

$$QQDYSSPX_{18} \quad (VI),$$

wherein: $X_1$ is any amino acid such as a polar or charged amino acid; $X_2$ is any amino acid such as a non-polar amino acid; $X_3$ is any amino acid such as a polar amino acid; $X_4$ is any amino acid such as a non-polar amino acid; $X_5$ is any amino acid such as a non-polar or polar amino acid; $X_6$ is any amino acid such as a polar amino acid; $X_7$ is any amino acid such as a non-polar or polar amino acid; $X_8$ is any amino acid such as a polar amino acid; $X_9$ is any amino acid such as a charged or non-polar amino acid; $X_{10}$ is any amino acid such as a polar amino acid; $X_{11}$ is either absent or is any amino acid such as a non-polar amino acid; $X_{12}$ is any amino acid such as a polar amino acid; $X_{13}$ is any amino acid such as a polar amino acid; $X_{14}$ is any amino acid such as a polar or non-polar amino acid; $X_{15}$ is any amino acid such as a polar or non-polar amino acid; $X_{16}$ is any amino acid such as a non-polar amino acid; $X_{17}$ is any amino acid such as a polar amino acid; and $X_{18}$ is any amino acid such as a polar or non-polar amino acid.

Composition 11. The isolated antibody or antigen binding fragment of composition 10 wherein: $X_1$ is a polar or charged amino acid; $X_2$ is a non-polar amino acid; $X_3$ is a polar amino acid; $X_4$ is a non-polar amino acid; $X_5$ is a non-polar or polar amino acid; $X_6$ is a polar amino acid; $X_7$ is a non-polar or polar amino acid; $X_8$ is a polar amino acid; $X_9$ is a charged or non-polar amino acid; $X_{10}$ is a polar amino acid; $X_{11}$ is either absent or is a non-polar amino acid; $X_{12}$ is a polar amino acid; $X_{13}$ is a polar amino acid; $X_{14}$ is a polar or non-polar amino acid; $X_{15}$ is a polar or non-polar amino acid; $X_{16}$ is a non-polar amino acid; $X_{17}$ is a polar amino acid; and $X_{18}$ is a polar or non-polar amino acid.

Composition 12. The isolated antibody or antigen binding fragment of composition 10 or composition 11 wherein: $X_1$ is D or N; $X_2$ is L or M; $X_3$ is Y or H; $X_4$ is I or G; $X_5$ is F or S; $X_6$ is N or S; $X_7$ is G or N; $X_8$ is S or T; $X_9$ is R or W; $X_{10}$ is T or S; $X_{11}$ is either absent or is I; $X_{12}$ is S or N; $X_{13}$ is Y or N; $X_{14}$ is F or Y; $X_{15}$ is Y or F; $X_{16}$ is V or A; $X_{17}$ is S or Y; and $X_{18}$ is F or Q.

Composition 13. The isolated antibody or antigen binding fragment of any one of compositions 10 to 12 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8, or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 14. An isolated antibody or antigen binding fragment thereof that binds to Ag43a (SEQ ID NO: 1) at an epitope comprising one or more residues selected from the group consisting of N83, R113, N114, D133, N150, T151, T152, G169, R254, E270, T291, T310, R330, G332, A333, S335, T361, N362, R364, T380, T381, S383, N386, S399, T401, D404 and G405.

Composition 15. The isolated antibody or antigen binding fragment of composition 14 wherein the antibody or antigen binding fragment binds to one or more residues selected from the group consisting of R330, G332, A333, S335, T361, N362, R364, T380, T381, S383, N386, S399, T401, D404 and G405 of Ag43a (SEQ ID NO: 1).

Composition 16. The isolated antibody or antigen binding fragment of composition 14 or composition 15 wherein the antibody or antigen binding fragment binds to one or more amino acid residues within amino acids 330 to 405 of Ag43a (SEQ ID NO: 1).

Composition 17. The isolated antibody or antigen binding fragment of any one of compositions 14 to 16 wherein the antibody or antigen binding fragment binds to residues R330, G332, A333, S335, T361, N362, R364, T380, T381, S383, N386, S399, T401, D404 and G405 of Ag43a (SEQ ID NO: 1).

Composition 18. The isolated antibody or antigen binding fragment of any one of compositions 14 to 17 wherein the antibody or antigen binding fragment binds to Ag43a (SEQ ID NO: 1) with a $K_D$ of less than about 10 nM.

Composition 19. The isolated antibody or antigen binding fragment of any one of compositions 14 to 18 wherein the antibody or antigen binding fragment binds to Ag43a (SEQ ID NO: 1) with a $K_D$ of less than about 8 nM.

Composition 20. The isolated antibody or antigen binding fragment of any one of compositions 14 to 19 comprising: a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

Composition 21. The isolated antibody or antigen binding fragment of any one of compositions 14 to 20 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8, or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 22. An isolated antibody or antigen binding fragment thereof that competes for binding to Ag43a with an antibody or antigen binding fragment of any one of compositions 1 to 21.

Composition 23. An isolated antibody or antigen binding fragment thereof that binds to the same epitope as the antibody or antigen binding fragment of any one of compositions 1 to 21.

Composition 24. An isolated antibody or antigen binding fragment thereof that specifically binds to an autotransporter.

Composition 25. The isolated antibody or antigen binding fragment of composition 24 wherein the antibody or antigen binding fragment specifically binds to a passenger domain of the autotransporter.

Composition 26. The isolated antibody or antigen binding fragment of composition 24 or composition 25 wherein the autotransporter is a homodimerising autotransporter.

Composition 27. The isolated antibody or antigen binding fragment of composition 26 wherein the antibody or antigen binding fragment inhibits homodimerisation of the autotransporter.

Composition 28. The isolated antibody or antigen binding fragment of any one of compositions 24 to 27 wherein the autotransporter is an AIDA-I type autotransporter.

Composition 29. The isolated antibody or antigen binding fragment of any one of compositions 24 to 28 wherein the autotransporter is Ag43a, Ag43b, Ag43 or TibA.

Composition 30. The isolated antibody or antigen binding fragment of any one of compositions 24 to 29 wherein the autotransporter is Ag43a.

Composition 31. The isolated antibody or antigen binding fragment of any one of compositions 24 to 30 wherein the antibody is a monoclonal antibody or an antigen binding fragment thereof.

Composition 32. The isolated antibody or antigen binding fragment of any one of compositions 24 to 31 wherein the isolated antibody or antigen binding fragment binds to the autotransporter with a $K_D$ of less than about 10 nM.

Composition 33. The isolated antibody or antigen binding fragment of any one of compositions 24 to 32 wherein the isolated antibody or antigen binding fragment binds to the autotransporter with a $K_D$ of less than about 8 nM.

Composition 34. The isolated antibody or antigen binding fragment of any one of compositions 24 to 33 comprising: a) a VH comprising the sequence set forth in SEQ ID NO: 9 or a sequence having at least 90% identity to SEQ ID NO: 9, and a VL comprising the sequence set forth in SEQ ID NO: 10 or a sequence having at least 90% identity to SEQ ID NO: 10; or b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

Composition 35. The isolated antibody or antigen binding fragment of any one of compositions 24 to 34 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8; or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 36. An isolated antibody or antigen binding fragment thereof that reduces binding of one autotransporter molecule to another autotransporter molecule.

Composition 37. The isolated antibody or antigen binding fragment of composition 36 wherein the autotransporter molecule is an AIDA-I type autotransporter.

Composition 38. The isolated antibody or antigen binding fragment of composition 36 or composition 37 wherein the autotransporter molecule is Ag43a, Ag43b, Ag43 or TibA.

Composition 39. The isolated antibody or antigen binding fragment of any one of compositions 36 to 38 wherein the autotransporter molecule is Ag43a.

Composition 40. The isolated antibody or antigen binding fragment of any one of compositions 36 to 39 comprising: a) a VH comprising the sequence set forth in SEQ ID NO:

9 or a sequence having at least 90% identity to SEQ ID NO: 9, and a VL comprising the sequence set forth in SEQ ID NO: 10 or a sequence having at least 90% identity to SEQ ID NO: 10; or b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

Composition 41. The isolated antibody or antigen binding fragment of any one of compositions 36 to 40 comprising: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8; or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 42. An isolated antibody or antigen binding fragment thereof that competes for binding to Ag43a with a control antibody, wherein the control antibody comprises: a) a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8; or b) a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 43. The isolated antibody or antigen binding protein of composition 42 wherein the control antibody reduces binding of the isolated antibody or antigen binding fragment to Ag43a by at least 20% when the control antibody and the isolated antibody or antigen binding fragment are used at approximately equal molar concentrations.

Composition 44. The isolated antibody or antigen binding protein of composition 42 or composition 43 wherein the control antibody reduces binding of the isolated antibody or antigen binding fragment to Ag43a by at least 50% when the control antibody and the isolated antibody or antigen binding fragment are used at approximately equal molar concentrations.

Composition 45. The isolated antibody or antigen binding protein of any one of compositions 42 to 44 wherein the control antibody comprises: a CDRH1 comprising the sequence set forth in SEQ ID NO: 3; a CDRH2 comprising the sequence set forth in SEQ ID NO: 4; a CDRH3 comprising the sequence set forth in SEQ ID NO: 5; a CDRL1 comprising the sequence set forth in SEQ ID NO: 6; a CDRL2 comprising the sequence set forth in SEQ ID NO: 7; and a CDRL3 comprising the sequence set forth in SEQ ID NO: 8.

Composition 46. The isolated antibody or antigen binding protein of any one of compositions 42 to 44 wherein the control antibody comprises: a CDRH1 comprising the sequence set forth in SEQ ID NO: 15; a CDRH2 comprising the sequence set forth in SEQ ID NO: 16; a CDRH3 comprising the sequence set forth in SEQ ID NO: 17; a CDRL1 comprising the sequence set forth in SEQ ID NO: 18; a CDRL2 comprising the sequence set forth in SEQ ID NO: 19; and a CDRL3 comprising the sequence set forth in SEQ ID NO: 20.

Composition 47. The isolated antibody or antigen binding fragment of any one of compositions 42 to 44 wherein the control antibody comprises: a) a VH comprising the sequence set forth in SEQ ID NO: 9 and a VL comprising the sequence set forth in SEQ ID NO: 10; or b) a VH comprising the sequence set forth in SEQ ID NO: 21 and a VL comprising the sequence set forth in SEQ ID NO: 22.

Composition 48. The isolated antibody or antigen binding fragment of any one of compositions 42 to 44 wherein the control antibody comprises: a) a heavy chain comprising the sequence set forth in SEQ ID NO: 13 and a light chain comprising the sequence set forth in SEQ ID NO: 14; or b) a heavy chain comprising the sequence set forth in SEQ ID NO: 25 and a light chain comprising the sequence set forth in SEQ ID NO: 26.

Composition 49. The isolated antibody or antigen binding fragment of any one of compositions 1 to 48 wherein the isolated antibody is a monoclonal antibody or an antigen binding fragment thereof.

Composition 50. The isolated antibody or antigen binding fragment of any one of compositions 1 to 49 wherein the isolated antibody is a murine antibody or an antigen binding fragment thereof.

Composition 51. The isolated antibody or antigen binding fragment of any one of compositions 1 to 50 wherein the isolated antibody is a chimeric antibody or an antigen binding fragment thereof.

Composition 52. The isolated antibody or antigen binding fragment of any one of compositions 1 to 51 wherein the isolated antibody is a humanised antibody or an antigen binding fragment thereof.

Composition 53. The isolated antibody or antigen binding fragment of any one of compositions 1 to 51 wherein the isolated antibody is a fully human antibody or antigen binding fragment thereof.

Composition 54. The isolated antibody or antigen binding fragment of any one of compositions 1 to 53 wherein the isolated antibody is a bispecific or bivalent antibody or an antigen binding fragment thereof.

Composition 55. The isolated antibody or antigen binding fragment of any one of compositions 1 to 54 wherein the isolated antibody is a multivalent antibody or an antigen binding fragment thereof.

Composition 56. The isolated antibody or antigen binding fragment of any one of compositions 1 to 55 wherein the isolated antibody or antigen binding fragment is an antigen binding protein selected from the group consisting of a Fab fragment, a F(ab')$_2$ fragment, a scFv, a scAb, a dAb, a diabody, a single domain heavy chain antibody and a single domain light chain antibody.

Composition 57. The isolated antibody or antigen binding fragment of any one of compositions 1 to 56 wherein the isolated antibody or antigen binding fragment is a Fab fragment.

Composition 58. The isolated antibody or antigen binding fragment of any one of compositions 1 to 55 wherein the isolated antibody or antigen binding fragment is a full length IgG antibody.

Composition 59. The isolated antibody or antigen binding fragment of any one of compositions 1 to 58 wherein the isolated antibody or antigen binding fragment is conjugated to a detectable moiety, a diagnostic agent or an antibiotic agent.

Composition 60. An isolated nucleic acid encoding the antibody or antigen binding fragment of any one of compositions 1 to 59.

Composition 61. An isolated nucleic acid encoding a heavy chain variable region or a light chain variable region of the antibody or antigen binding fragment of any one of compositions 1 to 59.

Composition 62. An isolated nucleic acid encoding: a VH comprising the sequence set forth in SEQ ID NO: 9 or SEQ ID NO: 21 or a sequence having at least 90% identity to SEQ ID NO: 9 or SEQ ID NO: 21; or a VL comprising the sequence set forth in SEQ ID NO: 10 or SEQ ID NO: 22 or a sequence having at least 90% identity to SEQ ID NO: 10 or SEQ ID NO: 22.

Composition 63. The isolated nucleic acid of composition 62 encoding: a VH comprising the sequence set forth in SEQ ID NO: 9 or SEQ ID NO: 21; or a VL comprising the sequence set forth in SEQ ID NO: 10 or SEQ ID NO: 22.

Composition 64. The isolated nucleic acid of composition 62 or composition 63 encoding: a heavy chain comprising the sequence set forth in SEQ ID NO: 13 or SEQ ID NO: 25 or a sequence having at least 90% identity to SEQ ID NO: 13 or SEQ ID NO: 25; or a light chain comprising the sequence set forth in SEQ ID NO: 14 or SEQ ID NO: 26 or a sequence having at least 90% identity to SEQ ID NO: 14 or SEQ ID NO: 26.

Composition 65. An isolated expression vector comprising the isolated nucleic acid of any one of compositions 60 to 64.

Composition 66. A host cell comprising the isolated nucleic acid of any one of compositions 60 to 64 or the expression vector of composition 65.

Method 1. A method of producing an antibody or antigen binding fragment the method comprising culturing the host cell of composition 66 under conditions that allow production of the antibody or antigen binding fragment and purifying the antibody or antigen binding fragment from the host cell.

Composition 67. A composition comprising the isolated antibody or antigen binding fragment of any one of compositions 1 to 59 and an antibiotic agent.

Composition 68. The composition of composition 67 wherein the antibiotic agent is selected from the group consisting of aminoglycoside, polyene, nitroimidazole, rifamycin, bacitracin, a beta-lactam, cephalosporin, chloramphenicol, a glycopeptide, a macrolide, a lincosamide, penicillin, a quinolone, rifampicin, tetracycline, trimethoprim a sulfonamide, amoxicillin, augmentin, amoxicillin, ampicillin, azlocillin, flucloxacillin, mezlocillin, methicillin, cephalexin, cefazedone, cefuroxime, loracarbef, cemetazole, cefotetan, cefoxitin, ciprofloxacin, levaquin, floxacin, doxycycline, minocycline, gentamycin, amikacin, tobramycin, clarithromycin, azithromycin, erythromycin, daptomycin, neomycin, kanamycin, streptomycin, nisin, epidermin, gallidennin, cinnamycin, duramycin, lacticin 481, amoxicillin, amoxicillin/clavulanic acid, metronidazole, clindamycine, chlortetracycline, dcmeclocycline, oxytetracycline, amikacin, netilmicin, cefadroxil, cefazolin, cephalexin, cephalothin, cephapirin, cephradine, cefaclor, cefamandole, cefametazole, cefonicid, cefotetan, cefoxitine, cefpodoxime, cefprozil, cefuroxime, cefdinir, cefixime, cefoperazone, cefotaxime, ceftazidime, ceftibuten, ceftizoxime, ceftriaxone, cefepime, azithromycin, claforan, clarithromycin, dirithromycin, erythromycin, lincomycin, troleandomycin, bacampicillin, carbenicillin, cloxacillin, dicloxacillin, meticillin, mezlocillin, nafcillin, oxacillin, piperacillin, ticarcillin, cinoxacin, ciprofloxacin, enoxacin, grepafloxacin, levofloxacin, lomefloxacin, nalidixic acid, norfloxacin, ofloxacin, sparfloxacin, sulfisoxazole, sulfacytine, sulfadiazine, sulfamethoxazole, sulfisoxazole, dapson, aztreonam, bacitracin, capreomycin, clofazimine, colistimethate, colistin, cycloserine, fosfomycin, furazolidone, methenamine, nitrofurantoin, pentamidine, rifabutin, spectinomycin, tigecycline, trimethoprim, trimetrexate glucuronate, vancomycin, chlorhexidine, carbapenem, imipenem, cilastatin and ertapenem.

Method 2. A method of reducing aggregation of two or more bacteria the method comprising contacting the two or more bacteria with an effective amount of the antibody or antigen binding fragment of any one of compositions 1 to 59 or the composition of composition 67 or composition 68.

Method 3. The method of method 2 wherein the two or more bacteria are E. coli.

Method 4. The method of method 2 or method 3 wherein the two or more bacteria are selected from the group consisting of avian pathogenic E. coli (APEC), diffusely adhering E. coli (DAEC), enterohemorrhagic E. coli (EHEC), enterotoxigenic E. coli (ETEC), shiga toxin-producing E. coli (STEC), enteropathogenic E. coli (EPEC) and uropathogenic E. coli (UPEC).

Method 5. The method of any one of methods 2 to 4 wherein the two or more bacteria are UPEC.

Method 6. The method of any one of methods 2 to 5 wherein the two or more bacteria are UPEC strain CFT037.

Method 7. A method of inhibiting interaction between two or more autotransporter molecules the method comprising contacting at least one of said two or more autotransporter molecules with the antibody or antigen binding fragment of any one of compositions 1 to 59.

Method 8. The method of method 7 wherein the two or more autotransporter molecules are AIDA-I type autotransporters.

Method 9. The method of method 7 or method 8 wherein the two or more autotransporter molecules are one of Ag43a, Ag43b, Ag43 or TibA.

Method 10. The method of any one of methods 7 to 9 wherein the two or more autotransporter molecules are Ag43a.

Method 11. A method of inhibiting homodimerisation between two autotransporter molecules the method comprising contacting at least one of said two autotransporter molecules with an autotransporter-binding molecule wherein the autotransporter-binding molecule binds to the at least one autotransporter molecule and thereby blocks homodimerisation between the two autotransporter molecules.

Method 12. The method of method 11 wherein the autotransporter-binding molecule is an antibody or an antigen binding fragment thereof.

Method 13. The method of method 12 wherein the antibody or antigen binding fragment is the antibody or antigen binding fragment of any one of compositions 1 to 59.

Method 14. The method of any one of methods 11 to 13 wherein the autotransporter-binding molecule binds to a passenger domain of the at least one autotransporter molecule.

Method 15. The method of any one of methods 11 to 14 wherein the two autotransporter molecules are AIDA-I type autotransporters.

Method 16. The method of any one of methods 11 to 15 wherein the two autotransporter molecules are one of Ag43a, Ag43b, Ag43 or TibA.

Method 17. The method of any one of methods 79 to 84 wherein the two autotransporter molecules are Ag43a.

Method 18. A method of treating a bacterial infection in a subject, the method comprising administering to the subject a therapeutically effective amount of the antibody or antigen binding fragment of any one of compositions 1 to 59 or the composition of composition 67 or composition 68.

Method 19. The method of method 18 wherein the bacterial infection is a urinary tract infection, a respiratory tract infection, a gastrointestinal tract infection, a pulmonary infection, a throat infection, a mouth infection, a medical device related infection, an orthopaedic implant infection, a biliary stent related infection or a catheter related infection.

Method 20. The method of method 18 or method 19 wherein the bacterial infection is an *E. coli* infection.

Method 21. The method of method 20 wherein the *E. coli* is a strain of avian pathogenic *E. coli* (APEC), diffusely adhering *E. coli* (DAEC), enterohemorrhagic *E. coli* (EHEC), enterotoxigenic *E. coli* (ETEC), shiga toxin-producing *E. coli* (STEC), enteropathogenic *E. coli* (EPEC) or uropathogenic *E. coli* (UPEC).

Method 22. The method of method 21 wherein the *E. coli* is UPEC.

Method 23. The method of method 22 wherein the UPEC is strain CFT037.

Method 24. The method of any one of methods 18 to 23 wherein the bacterial infection is a urinary tract infection.

Method 25. A method of treating a disease or disorder associated with a bacterial infection in a subject the method comprising administering to the subject a therapeutically effective amount of the antibody or antigen binding fragment of any one of compositions 1 to 59 or the composition of composition 67 or composition 68.

Method 26. The method of method 25 wherein the disease or disorder is aerosacculitis, pneumonia, polyserositis, septicemia, diarrhoea, edema, a urinary tract infection, a respiratory tract infection, a gastrointestinal tract infection or a pulmonary infection.

Method 27. The method of method 26 wherein the disease or disorder is a urinary tract infection.

Method 28. A method of removing a bacterium from a surface the method comprising contacting the bacterium with an effective amount of an autotransporter-binding molecule wherein the autotransporter-binding molecule binds to an autotransporter molecule expressed by the bacterium.

Method 29. The method of method 28 wherein the autotransporter-binding molecule is the antibody or antigen binding fragment of any one of compositions 1 to 59.

Method 30. A method of inhibiting autotransporter-mediated attachment of a bacterium to a surface, the method comprising contacting the bacterium with an effective amount of an autotransporter-binding molecule, wherein the autotransporter-binding molecule binds to an autotransporter molecule expressed by the bacterium and thereby inhibits an interaction between the autotransporter molecule and the surface.

Method 31. The method of method 30 wherein the autotransporter-binding molecule is an antibody or antigen binding fragment thereof.

Method 32. The method of any one of methods 28 to 31 wherein the autotransporter-binding molecule binds to a passenger domain of the autotransporter molecule.

Method 33. The method of any one of methods 28 to 32 wherein the autotransporter is an AIDA-I type autotransporter.

Method 34. The method of any one of methods 28 to 33 wherein the autotransporter molecule is UpaB.

Method 35. The method of any one of methods 28 to 34 wherein the surface is a medical device surface or personal care device surface.

Method 36. The method of any one of methods 28 to 35 wherein the surface is a surface of an orthopaedic implant, a stent, a catheter, a prosthesis, a pacemaker or a contact lens.

Method 37. The method of any one of methods 28 to 34 wherein the surface is a cellular surface of a eukaryotic organism.

Method 38. The method of method 37 wherein the eukaryotic organism is an animal.

Method 39. The method of method 38 wherein the cellular surface is a urinary tract surface or a gastrointestinal tract surface.

Method 40. A method of inhibiting autotransporter-mediated aggregation of two or more bacteria wherein the two or more bacteria express an autotransporter molecule, the method comprising contacting the two or more bacteria with an effective amount of an autotransporter-binding molecule, wherein the autotransporter-binding molecule binds to the autotransporter molecule and thereby inhibits aggregation of the two or more bacteria.

Method 41. The method of method 40 wherein the autotransporter-binding molecule binds to a passenger domain of the autotransporter molecule.

Method 42. The method of method 40 or method 41 wherein the autotransporter is an AIDA-I type autotransporter.

Method 43. The method of any one of methods 40 to 42 wherein the autotransporter molecule is Ag43a, Ag43b, Ag43 or TibA.

Method 44. The method of any one of methods 40 to 43 wherein the autotransporter molecule is Ag43a.

Method 45. The method of any one of methods 40 to 44 wherein the autotransporter-binding molecule is an antibody or antigen binding fragment thereof.

Method 46. The method of method 45 wherein the antibody or antigen binding fragment thereof is the antibody or antigen binding fragment of any one of compositions 1 to 59.

Use 1. Use of the antibody or antigen binding fragment of any one of compositions 1 to 59 or the composition of composition 67 or composition 68 in the manufacture of a medicament for reducing aggregation of two or more bacteria.

Use 2. Use of the antibody or antigen binding fragment of any one of compositions 1 to 59 or the composition of composition 67 or composition 68 in the manufacture of a medicament for inhibiting interaction between two or more autotransporter molecules.

Use 3. Use of an autotransporter-binding molecule in the manufacture of a medicament for inhibiting homodimerisation between two autotransporter molecules wherein the autotransporter-binding molecule binds to at least one of the autotransporter molecules and thereby blocks homodimerisation between the two autotransporter molecules.

Use 4. Use of the antibody or antigen binding fragment of any one of compositions 1 to 59 or the composition of composition 67 or composition 68 in the manufacture of a medicament for treating a bacterial infection in a subject.

Use 5. Use of the antibody or antigen binding fragment of any one of compositions 1 to 59 or the composition of composition 67 or composition 68 in the manufacture of a medicament for treating a disease or disorder associated with a bacterial infection in a subject.

Use 6. Use of an autotransporter-binding molecule in the manufacture of a medicament for removing a bacterium from a surface wherein the autotransporter-binding molecule binds to an autotransporter molecule expressed by the bacterium.

Use 7. Use of an autotransporter-binding molecule in the manufacture of a medicament for inhibiting autotransporter-mediated attachment of a bacterium to a surface wherein the autotransporter-binding molecule binds to an autotransporter molecule expressed by the bacterium and thereby inhibits an interaction between the autotransporter molecule and the surface.

Use 8. Use of an autotransporter-binding molecule in the manufacture of a medicament for inhibiting autotransporter-mediated aggregation of two or more bacteria wherein the two or more bacteria express an autotransporter molecule, and wherein the autotransporter-binding molecule binds to the autotransporter molecule and thereby inhibits aggregation of the two or more bacteria.

EXAMPLES

Bacteria and Plasmids

*E. coli* strains used in the present examples include those listed in Table 4.

TABLE 4

Bacterial strains used in the present examples.

| Strain | Description | References |
|---|---|---|
| MS427 | MG1655Δflu (agn43 null strain) | Kjaergaard et al. J Bacteriol. 2000. 182: 4789-4796 |
| MS1187 | MS427 pBAD/Myc-His A (agn43 null strain with empty vector) | Kjaergaard et al. J Bacteriol. 2000. 182: 4789-4796 |
| MS1232 | MS427 pCO4 (agn43 null strain expressing Ag43a) | Kjaergaard et al. J Bacteriol. 2000. 182: 4789-4796 |

Plasmids used in the present examples include those listed in Table 5.

TABLE 5

Plasmids used in the present examples.

| Plasmid | Description | References |
|---|---|---|
| LicE:ag43a | pMCSG7/TRX-His:ag43a$^\alpha$ | Heras et al. Proc. Natl. Acad. Sci. USA. 2014. 111: 457-462<br>Eschenfeldt et al. Meth. Mol. Biol. 2009. 498: 105-115 |
| pCO4 | pBAD/Myc-His A::ag43 | Kjaergaard et al. J Bacteriol. 2000. 182: 4789-4796<br>Martinez et al. Gene. 1988. 68: 159-192 |

Sequences

Sequences relevant to the present examples are listed in Tables 6, 7 and 8.

TABLE 6

Autotransporter sequences.

| SEQ ID NO: | Description | Sequence |
|---|---|---|
| 1 | Ag43a from UPEC strain CFT073 (full length) Passenger domain is underlined Interface residues are bold Fab10C12 interacting residues are italicized | MLMKRHLNTCYRLVWNHITGAFVVASELARARGKRGGVAVAL SLAAVTPLPVLS<u>ADIVVHPGETVNGGTLVNHDNQFVSGTANG VTVSTGLELGPDSDENTGGQWIKAGGTGRNTTVTANGRQIVQ AGGTASDTVIRDGGGQSLNGLAVNTTLDNRGEQWVHGGGKAA GTIINQDGYQTIKHGGLATGTIVNTGAEGGPESENVSSGQMV GGTAESTTINKNGRQVIWSSGMARDTLIYAGGDQTVHGEAHN TRLEGGNQYVHNGGTATETLINRDGWQVIKEGGTAAHTTINQ KGKLQVNAGGKASDVTQNTGGALVTSTAATVTGTNRLGAF*SV* VAGKADNVVLENGGRLDVLSGHTA*TNT*RVDDGGTLDIRNGGA A*TTV*SMGNGGVLLADSGAAV*SG*T*RSDG*KAFSIGGGQADALML EKGSSFTLNAGDTATDTTVNGGLFTARGGTLAGTTTLNNGAI LTLSGKTVNNDTLTIREGDALLQGGSLIGNGSVEKSGSGTLT VSNTTTLTQKAVNLNEGTLTLNDSTVTTDVIAQRGTALKLIGS TVLNGAIDPTNVTLASDATWNIPDNATVQSVVDDLSHAGQIH FTSSRTGTFVPATLKVKNLNGQNGTISLRVRPDMAQNNADRL VIDGGRATGKTILNLVNAGNSASGLATSGKGIQVVEAINGAT TEEGAFVOGNRLQAGAFNYSLNRDSDESWYLRSENAYRAEVP LYASMLTQAMDYDRILAGSRSHQTGVNGENNSVRLSIQGGHL GHDNNGGIARGATPESSGSYGFVRLEGDLLRTDVAGMSVTAG IYGAAGHSSVDVKDDDGSRAGTVRDDAGSLGGYMNLTHTSSG LWADIVAQGTRHSMKASSGNNDFRARGRGWLGSLETGLPFSI TDNLMLEPRLQYTWQGLSLDDGKDNAGYVKFGHGSAQHVRAG FRLGSHNDMTFGEGTSSRAPLRDSAKHSVRELPVNWWVQPSV IRTFSSRGDMRVGTSTAGSGMTFSPSQNGTSLDLQAGLEARV RENITLGVQAGYAHSVSGSSAEGYNGQATLNVTF</u> |
| 2 | Ag43a passenger domain (Ag43a$^\alpha$) Δ7 loop residues are bold ΔL1 and ΔL2 deletions in lower case and italics | ADIVVHPGETVNGGTLVNHDNQFVSGTANGVTVSTG*lelgpd sdent*GGQWIKAGGTGRNTTVTANGRQIVQAGGTASDTVIRD GGGQSLNGLAVNTTLDNRGEQWVHGGGKAAGTIINQDGYQTI KHGGLATGTIVNTG*aeggpesenvs*SGQMVGGTAESTTINKN GRQVIWSSGMARDTLIYAGGDQTVHGEAHNTRLEGGNQYVHN GGTATETLINRDGWQVIKEGGTAAHTTINQKGKLQVNAGGKA SDVTQNTGGALVTSTAATVTGTN<u>RLGAF*SV*</u>VAGKADNVVLEN GGRLDVLSGHTA*TNT*RVDDGGTLDIRNGGAA*TTV*SMGNGGVL LADSGAAV*SGTRSDGKAFSI*GGGQADALMLEKGSSFTLNAGD |

TABLE 6-continued

Autotransporter sequences.

| SEQ ID NO: | Description | Sequence |
|---|---|---|
| | ΔH1 and H2 deletions underlined Fab10C12 interacting residues are italicized | TATDTTVNGGLFTARGGTLAGTTTLNNGAILTLSGKTVNNDT LTIREGDALLQGGSLTGNGSVEKSGSGTLTVSNTTLTQKAVN LNEGTLTLNDSTVTTDVIAQRGTALKLIGSTVLNGAID |
| 27 | ΔL1: deleted region of Ag43a | LELGPDSDENT |
| 28 | ΔL2: deleted region of Ag43a | AEGGPESENVS |
| 29 | ΔH1: deleted region of Ag43a | AATVTGTNRLGAFSVVA |
| 30 | ΔH2: deleted region of Ag43a | GAAVSGTRSDGKAFSIG |
| 31 | Ag43 from UPEC strain UTI189 (full length) Signal sequence is in italics Passenger domain is underlined Interface binding residues are bold | *MKRHLNTSYRLVWNHITGTLVVASELARSRGKGAGVAVALSL AAVTSVPALA*ADTVVQAGETVNGGTLTNHDNQIVLGTANGMT ISTGLEYGPDNEANTGGQWIQNGGIANNTTVTGGGLQRVNAG GSVSDTVISAGGGQSLQGQAVNTTLNGGEQWVHEGGIATGTV INEKGWQAVKSGAMATDTVVNTGAEGGPDAENGDTGQTVYGD AVRTTINKNGRQIVAAEGTANTTVVYAGGDQTVHGHALDTTL NGGYQYVHNGGTASDTVVNSDGWQIIKEGGLADFTTVNQKGK LQVNAGGTATNVTLTQGGALVTSTAATVTGSNRLGNFTVENG NADGVVLESGGRLDVLEGHSAWKTLVDDGGTLAVSAGGKATD VTMTSGGALIADSGATVEGTNASGKFSIDGISGQASGLLLEN GGSFTVNAGGLASNTTVGHRGTLTLAAGGSLSGRTQLSKGAS MVLNGDVVSTGDIVNAGEIRFDNQTTPDAALSRAVAKGDSPV TFHKLTTSNLTGQGGTINMRVRLDGSNASDQLVINGGQATGK TWLAFTNVGNSNLGVATSGQGIRVVDAQNGATTEEGAFALSR PLQAGAFNYTLNRDSDEDWYLRSENAYRAEVPLYASMLTQAM DYDRILAGSRSHQSGVSGENNSVRLSIQGGHLGHDNNGGIAR GATPESNGSYGFVRLEGDLLRTEVAGMSLTTGVYGAAGHSSV DVKDDDGSRAGTVRDDAGSLGGYLHLVHTSSGLWADIVAQGT RHSMKASSDNNDFRARGWGWLGSLETGLPFSITDNLMLEPQL QYTWQGLSLDDGQDNAGYVKFGHGSAQHVRAGFRLGSHNDMN FGKGTSSRDTLHDSAKHSVRELPVNWWVQPSVIRTFSSRGDM SMGTAAAGSNMTFSPSRNGTSLDLQAGLEARVRENITLGVQA GYAHSVSGSSAEGYNGQATLNVTF |
| 32 | Ag43 passenger domain (Ag43α) from UPEC strain UTI189 | ADTVVQAGETVNGGTLINHDNQIVLGTANGMTISTGLEYGPD NEANTGGQWIQNGGIANNTTVTGGGLQRVNAGGSVSDTVISA GGGQSLQGQAVNTTLNGGEQWVHEGGIATGTVINEKGWQAVK SGAMATDTVVNTGAEGGPDAENGDTGQTVYGDAVRTTINKNG RQIVAAEGTANTTVVYAGGDQTVHGHALDTTLNGGYQYVHNG GTASDTVVNSDGWQIIKEGGLADFTTVNQKGKLQVNAGGTAT NVTLTQGGALVTSTAATVTGSNRLGNFTVENGNADGVVLESG GRLDVLEGHSAWKTLVDDGGTLAVSAGGKATDVTMTSGGALI ADSGATVEGTNASGKFSIDGISGQASGLLLENGGSFTVNAGG LASNTTVGHRGTLTLAAGGSLSGRTQLSKGASMVLNGDVVST GDIVNAGEIRFDNQTTPDAALSRAVAKGDSPVTFHKLTTSNL TGQGGTINMRVRLDGSNASDQLVINGGQATGKTWLAFTNVGN SNLGVATSGQGIRVVDAQNGATTEEGAFALSRPLQAGAFNYT LNRDSDE |
| 33 | Ag43 from E. coli strain EDL933 (full length) Signal sequence is in italics Passenger domain is underlined Interface binding residues are bold | *MKRHLNTSYRLVWNHITGTLVVASELARSRGKRAGVAVALSL AAVTSVPALA*ADKVVQAGETVNDGTLTNHDNQIVFGTANGMT ISTGLELGPDSEENTGGQWIQNGGIAGNTTVTTNGRQVVLEG GTASDTVIRDGGGQSLNGLAVNTTLNNRGEQWVHEGGVATGT IINRDGYQSVKSGGLATGTIINTGAEGGPDSDNSYTGQKVQG TAESTTINKNGRQIILFSGLARDTLIYAGGDQSVHGRALNTT TLNGGYQYVHRDGLALNTVINEGGWQVVKAGGAAGNTTINQNG ELRVHAGGEATAVTQNTGGALVTSTAATVIGTNRLGNFTVEN GKADGVVLESGGRLDVLESHSAQNTLVDDGGTLAVSAGGKAT SVTITSGGALIADSGATVEGTNASGKFSIDGTSGQASGLLLE NGGSFTVNAGGQAGNTTVGHRGTLTLAAGGSLSGRTQLSKGA SMVLNGDVVSTGDIVNAGEIRFDNQTTPNAALSRAVAKSNSP VTFHKLTTTNLIGQGGTINMRVRLDGSNASDQLVINGGQATG KTWLAFTNVGNSNLGVATTGQGIRVVDAQNGATTEEGAFALS RPLQAGAFNYTLNRDSDEDWYLRSENAYRAEVPLYTSMLTQA MDYDRILAGSRSHQTGVNGENNSVRLSIQGGHLGHDNNGGIA |

TABLE 6-continued

Autotransporter sequences.

| SEQ ID NO: | Description | Sequence |
|---|---|---|
| | | RGATPESSGSYGFVRLEGDLLRTEVAGMSLTTGVYGAAGHSS VDVKDDDGSRAGTVRDDAGSLGGYLNLVHTSSGLWADIVAQG TRHSMKASSDNNDFRARGWGWLGSLETGLPFSITDNLMLEPQ LQYTWQGLSLDDGQDNAGYVKFGHGSAQHVRAGFRLGSHNDM TFGEGTSSRDTLRDSAKHSVSELPVNWWVQPSVIRTFSSRGD MSMGTAAAGSNMTFSPSRNGTSLDLQAGLEARIRENITLGVQ AGYAHSVSGSSAEGYNGQATLNMTF |
| 34 | Ag43 passenger domain (Ag43α) from E. coli strain EDL933 | ADKVVQAGETVNDGTLTNHDNQIVFGTANGMTISTGLELGPD SEEENTGGQWIQNGGIAGNTTVTTNGRQVVLEGGTASDTVIRD GGGQSLNGLAVNTTLNNRGEQWVHEGGVATGTIINRDGYQSV KSGGLATGTIINTGAEGGPDSDNSYTGQKVQGTAESTTINKN GRQIILFSGLARDTLIYAGGDQSVHGRALNTTLNGGYQYVHR DGLALNTVINEGGWQVVKAGGAAGNTTINQNGELRVHAGGEA TAVTQNTGGALVTSTAATVIGTNRLGNFTVENGKADGVVLES GGRLDVLESHSAQNTLVDDGGTLAVSAGGKATSVTITSGGAL IADSGATVEGTNASGKFSIDGTSGQASGLLLENGGSFTVNAG GQAGNTTVGHRGTLTLAAGGSLSGRTQLSKGASMVLNGDVVS TGDIVNAGEIRFDNQTTPNAALSRAVAKSNSPVTFHKLTTTN LTGQGGTINMRVRLDGSNASDQLVINGGQATGKTWLAFTNVG NSNLGVATTGQGIRVVDAQNGATTEEGAFALSRPLQAGAFNY TLNRDSDE |
| 35 | TibA from the enterotoxigenic E. coli strain H10407 (full length) Signal sequence is in italics Passenger domain is underlined Interface binding residues are bold | *MNKVYNTVWNESTGTWVVTSELTRKGGLRPRQIKRTVLAGLI AGLLMPSMPALAAA*YDNQTIGRGETSKSMHLSAGDTAKNTTI NSGGKQYVSSGGSATSTTINIGGVQHVSSGGSATSSTINSGG HQHVSSGGSATNTTVNNGGRQTVFSGGSAMGTIINSGGDQYV ISGGSATSASVTSGARQFVSSGGIVKATSVNSGGRQYVRDGG SATDTVLNNTGRQFVSSGGSAAKTTINSGGGMYLYGGSATGT SIYNGGRQYVSSGGSATNTTVYSGGRQHVYIDGNVTETTITS GGMLQVEAGGSASKVIQNSGGAVITNTSAAVSGTNDNGSFSI AGGSAVNMLLENGGYLTVFDGHQASDTMVGSDGTLDVRSGGV LYGTTTLTDKGALVGDVVTNEGNLYYLNNSTATFTGTLTGTG TLTQEGGNTRFSGLLSQDGGIFLQSGGAMTMDALQAKANVTT QSGTTLTLDNGTILTGNVAGDSTGAGDMAVKGASVWHLDGDS TVGALTLDNGTVDFRPSTTTRMTPAFQAVSLALGSLSGSGTF QMNTDIASHTGDMLNVAGNASGNFVLDIKNTGLEPVSAGAPL QVVQTGGGDAAFTLKGGKVDAGTWEYGLSKENTNWYLKADTP PPVTPPTNPDADNPDAGNPDAGNPDAGNPDAGNPDAGKPGTG KPDAGTSSSPVRRTTKSVDAVLGMATAPAYVENSELDNLRFR HGDVMQNTRAPGGVWGRYTGSDNRISGGASSGYTLTONGFET GADMVFDLSDSSLAVGTFFSYSDNSIKHARGGKSNVDSSGGG LYATWFDNDGYYVDGVLKYNRFNNELRTWMSDGTAVKGDYSQ NGFGGSLEAGRTFSLNENAWAQPYVRTTAFRADKKEIRLNNG MKASIGATKSLQAEAGLKLGMTLDVAGKEVKPYLSAAVSHEF SDNNKVRINDTYDFRNDISGTTGKYGLGVNAQLTPNAGVWAE ARYENGKQTESPITGGVGFRINF |
| 36 | TibA passenger domain (TibAα) from the enterotoxigenic E. coli strain H10407 | YDNQTIGRGETSKSMHLSAGDTAKNTTINSGGKQYVSSGGSA TSTTINIGGVQHVSSGGSATSSTINSGGHQHVSSGGSATNTT VNNGGRQTVFSGGSAMGTIINSGGDQYVISGGSATSASVTSG ARQFVSSGGIVKATSVNSGGRQYVRDGGSATDTVLNNTGRQF VSSGGSAAKTTINSGGGMYLYGGSATGTSIYNGGRQYVSSGG SATNTTVYSGGRQHVYIDGNVTETTITSGGMLQVEAGGSASK VIQNSGGAVITNTSAAVSGTNDNGSFSIAGGSAVNMLLENGG YLTVFDGHQASDTMVGSDGTLDVRSGGVLYGTTTLTDKGALV GDVVTNEGNLYYLNNSTATFTGTLTGTLTQEGGNTRFSGL LSQDGGIFLQSGGAMTMDALQAKANVTTQSGTTLTLDNGTIL TGNVAGDSTGAGDMAVKGASVWHLDGDSTVGALTLDNGTVDF RPSTTTRMTPAFQAVSLALGSLSGSGTFQMNTDIASHTGDML NVAGNASGNFVLDIKNTGLEPVSAGAPLQVVQTGGGDAAFTL KGGKVDAGTWEYGLSKENTNWYLKADT |
| 41 | Ag43b from uropathogenic E. coli strain CFT073 Signal sequence is in italics Passenger domain is underlined Interface binding residues are bold | *MQTHRHEIQGTTEPHVRNFHQPDLRHCNPSPAGIHICGYRLF IHPHSDKEMLMKRHLNTSYRLVWNHITGAFVVASELARARGK RAGVAVALSLAAATSLPALA*ADSVVPAGETVNGGTLINHDRQ FVSGTADGMTVSTGLELGPD<u>SDNNTGGQQIARGGTAR</u>NT<u>RVT</u> <u>ANGLQDVMAGGSTS</u>D<u>TVISTGGGQNLRGKA</u>S<u>GTVLNGGDQWI</u> <u>HAGGRA</u>S<u>GTVINQDGYQTIKHGGLVTGTIVNTGAEGGPDSEN</u> <u>VSTGQMVGGIAESTTINKNGRQVIWSSGIARD</u>T<u>LIYTGGDQT</u> <u>VHGEAHNTRLEGGNQYVHKYGLALNTVINEGGWQVVKAGGTA</u> <u>GNTT</u>IN<u>QNGELRVHAGGEASDV</u>T<u>QNTGGALVTSTAATVTGTN</u> <u>RLGAFSVVEGKADNVVLENGGRLDVLSGHTATRTLVDDGGTL</u> <u>DVRNGGTATAVSMGNGGVLLADSGAAVSGTRSDGTAFRIGGG</u> <u>QADALMLEKGSSFTLNAGDTATDTTVNGGLFTARGGSLAGTT</u> |

TABLE 6-continued

Autotransporter sequences.

| SEQ ID NO: | Description | Sequence |
|---|---|---|
| | | TLNNGATFTLAGKTVNNDTLTIREGDALLQGGALTGNGRVEK<br>SGSGTLTVSNTTLTQKAVNLNEGTLTLNDSTVTTDIIAHRGT<br>ALKLTGSTVLNGAIDPTNVTLTSGATWNIPDNATVQSVVDDL<br>SHAGQIHFTSARTGKFVPTTLQVKNLNGQNGTISLRVRPDMA<br>QNNADRLVIDGGRATGKTILNLVNAGNSGTGLATTGKGIQVV<br>EAINGATTEEGAFVQGNMLQAGAFNYTLNRDSDESWYLRSEE<br>RYRAEVPLYASMLTQAMDYDRILAGSRSHQTGVNGENNSVRL<br>SIQGGHLGHDNNGGIARGATPESSGSYGFVRLEGDLLRTEVA<br>GMSLTTGVYGAAGHSSVDVKDDDGSRAGTVRDDAGSLGGYMN<br>LTHTSSGLWADIVAQGTRHSMKASSDNNDFRARGRGWLGSLE<br>TGLPFSITDNLMLEPRLQYTWQGLSLDDGKDNAGYVKFGHGS<br>AQHVRAGFRLGSHNDMTFGEGTSSRAPLRDSAKHSVRELPVN<br>WWVQPSVIRTFSSRGDMRVGTSTAGSGMTFSPSQNGTSLDLQ<br>AGLEARVRENITLGVQAGYAHSINGSSAEGYNSQATLNVTF |
| 42 | Ag43b passenger domain (Ag43b$^\alpha$) from uropathogenic E. coli strain CFT073 | ADSVVPAGETVNGGTLINHDRQFVSGTADGMTVSTGLELGAD<br>SDNNTGGQQIARGGTARNTRVTANGLQDVMAGGSTSDTVIST<br>GGGQNLRGKASGTVLNGGDQWIHAGGRASGTVINQDGYQTIK<br>HGGLVTGTIVNTGAEGGPDSENVSTGQMVGGIAESTTINKNG<br>RQVIWSSGIARDTLIYTGGDQTVHGEAHNTRLEGGNQYVHKY<br>GLALNTVINEGGWQVVKAGGTAGNTTINQNGELRVHAGGEAS<br>DVTQNTGGALVTSTAATVTGTNRLGAFSVVEGKADNVVLENG<br>GRLDVLSGHTATRTLVDDGGTLDVRNGGTATAVSMGNGGVLL<br>ADSGAAVSGTRSDGTAFRIGGGQADALMLEKGSSFTLNAGDT<br>ATDTTVNGGLFTARGGSLAGTTTLNNGATFTLAGKTVNNDTL<br>TIREGDALLQGGALIGNGRVEKSGSGTLTVSNTTLTQKAVNL<br>NEGTLTLNDSTVTTDIIAHRGTALKLTGSTVLNGAIDPTNVT<br>LTSGATWNIPDNATVQSVVDDLSHAGQIHFTSARTGKFVPTT<br>LQVKNLNGQNGTISLRVRPDMAQNNADRLVIDGGRATGKTIL<br>NLVNAGNSGTGLATTGKGIQVVEAINGATTEEGAFVQGNMLQ<br>AGAFNYTLNRDSDESWYLRSEE |
| 43 | UpaB from uropathogenic E. coli strain CFT073 Fibronectin binding residues underlined Glycosaminoglycan binding residues in bold | MKLVTRMENFFMKNSKVFYRSALATAIVMALSAPAFATDSTV<br>STDPVTLNTEKTTLDQDVVINGDNKITAVTIETSDSDKDLNV<br>TFGGHDITAASTVNQDFVEGVKVSGNKNVVINATDSTITAQG<br>EGTYVRTAMVIDSTGDVVVNGGNFVAKNEKGS<u>AT</u>GISL<u>E</u>ATT<br>GNNLTL<u>N</u>GTTINAQGNKSYSNGSTAIFAQKGNLLQGFDGDAT<br>DNITLA<u>DS</u>NIINGGIETIVTAGNKTGIHTVNLNIKDGSVIGA<br>ANNKQTIYASASAQGAGSATQNLNLSVADSTIY<u>S</u>DVLALSES<br>ENSASTTTNVNMNVARSYWEGNAYTFNSGDKAGSDLDINLSD<br>SSVWKGKVSGAGDASVSLONGSVWNVTGSSTVDALAVKD<u>STV</u><br>NITKATVNTGTFASQNGTLIVDASSENTLDISGKASGDLRVY<br>SAGSLDLINEQTAFISTGKDSTLKATGTTEGGLYQYDLTQGA<br>DGNFYFVKNTHKASNASSVIQAMAAAPANVANLQADTLSARQ<br>DAVRLSENDKGGVWIQYFGGKQKHTTAGNASYDLDVNGVMLG<br>GDTRFMTEDGSWLAGVAMSSAKGDMTTMQSKGDTEGYSFHAY<br>LSRQYNNGIFIDTAAQFGHYSNTADVRLMNGGGTIKADFNTN<br>GFGAMVKGGYTWKDGNGLFIQPYAKLSALTLEGVDYQLNGVD<br>VHSDSYNSVLGEAGTRVGYDFAVGNATVKPYLNLAALNEFSD<br>GNKVRLGDESVNASIDGAAFRVGAVQADITKNMGAYASLDY<br>TKGDDIENPLQGVVGINVTW |

TABLE 7

Autotransporter binding proteins.

| SEQ ID NO: | Description | Sequence |
|---|---|---|
| | | Fab7D10 |
| 3 | CDRH1 | YTFTDYWLY |
| 4 | CDRH2 | WIGNIIPFNGGSNY |
| 5 | CDRH3 | RRGTRAMDY |
| 6 | CDRL1 | QSVSYDVA |
| 7 | CDRL2 | LLIFYVSNRST |
| 8 | CDRL3 | QQDYSSPF |

TABLE 7-continued

Autotransporter binding proteins.

| SEQ ID NO: | Description | Sequence |
|---|---|---|
| 9 | VH | QVQLQQPGTEVVKPGASVKLSCKASGYTFTDYWLYWVKQRPGQGLDWIGNIIPFNGGSNYNEKFKNKATLTVDESSSTAYMQLSSLTSEDSAVYYCARRGTRAMDYWGQGTSVTVSS |
| 10 | VL | SIVMTQTPKSLLVSAGDRVSITCKASQSVSYDVAWYQQKPGQSPKLLIFYVSNRSTGVPERFTGSGYGTDFTFTISTVQPEDLAVYFCQQDYSSPFTFGGGTKLELK |
| 11 | CH1 | AKTTPPSVYPLAPGSAAQTNSMVTLGCLVKGYFPEPVTVTWNSGSLSSGVHTFPAVLQSDLYTLSSSVTVPSSTWPSQTVTCNVAHPASSTKVDKKIVPRDC |
| 12 | CL | RADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| 13 | Heavy chain CDRs underlined | QVQLQQPGTEVVKPGASVKLSCKASGYTFTDYWLYWVKQRPGQGLDWIGNIIPFNGGSNYNEKFKNKATLTVDESSSTAYMQLSSLTSEDSAVYYCARRGTRAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSQTVTCNVAHPASSTKVDKKIVPRDCHHHHHH |
| 14 | Light chain CDRs underlined | SIVMTQTPKSLLVSAGDRVSITCKASQSVSYDVAWYQQKPGQSPKLLIFYVSNRSTGVPERFTGSGYGTDFTFTISTVQPEDLAVYFCQQDYSSPFTFGGGTKLELKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |

Fab10C12

| SEQ ID NO: | Description | Sequence |
|---|---|---|
| 15 | CDRH1 | YTFTNYWMH |
| 16 | CDRH2 | WIGNIGPSSGNTNY |
| 17 | CDRH3 | RWGSIRAMDY |
| 18 | CDRL1 | QSVNNDVA |
| 19 | CDRL2 | LLIYFASNRYT |
| 20 | CDRL3 | QQDYSSPQ |
| 21 | VH | QVQLQQPGTELVKPGASVKLSCKASGYTFTNYWMHWVKQRPGQGLEWIGNIGPSSGNTNYNENFKTKATLTVDKSSSTAYMQLSSLTSEDSAVYFCARWGSIRAMDYWGQGTSVTVSS |
| 22 | VL | SIVMTQTPKFLFVSVGDRVTITCKASQSVNNDVAWYQQKPGQSPKLLIYFASNRYTGVPDRFTGSGYGTDFTFTINTVQAEDLAVYFCQQDYSSPQTFGGGTKLEVT |
| 23 | CH1 | AKTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKL |
| 24 | CL | RADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| 25 | Heavy chain CDRs underlined | QVQLQQPGTELVKPGASVKLSCKASGYTFTNYWMHWVKQRPGQGLEWIGNIGPSSGNTNYNENFKTKATLTVDKSSSTAYMQLSSLTSEDSAVYFCARWGSIRAMDYWGQGTSVTVSSAKTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKLHHHHHH |
| 26 | Light chain CDRs underlined | SIVMTQTPKFLFVSVGDRVTITCKASQSVNNDVAWYQQKPGQSPKLLIYFASNRYTGVPDRFTGSGYGTDFTFTINTVQAEDLAVYFCQQDYSSPQTFGGGTKLEVTRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |

TABLE 8

Other relevant sequences.

| SEQ ID NO: | Description | Sequence |
|---|---|---|
| 37 | mVh1_For primer | ACCGCCACCGGTGTCCACTCCCAGGTCCAACTGCAGCAGCC |
| 38 | mG2b_Ch1_Rev primer | GGGCCCTCTAGATTAGTGATGGTGATGGTGATGAAGTTTTTTGTCCACCGTGGTGC |
| 39 | mVk6_For primer | ACCGCCACCGGTGTCCACTCCAGTATTGTGATGACCCAGACTCCC |
| 40 | mKappa_Rev primer | GGGCCCTCTAGATTAACACTCATTCCTGTTGAAGCTCTTG |

Example 1: Expression and Purification of Ag43a Passenger Domain (Ag43a$^\alpha$)

The amino acid sequence of Ag43a (Locus Tag c3655) from UPEC CFT073 is set forth as SEQ ID NO: 1. The passenger domain of Ag43a, the amino acid sequence of which is set forth as SEQ ID NO: 2, was PCR-amplified from genomic DNA and inserted into a vector encoding an N-terminal His$_6$-tag followed by thioredoxin (TRX) and a TEV protease cleavage site (LicE:ag43a$^\alpha$) (Heras et al. Proc. Natl. Acad. Sci. USA. 2014. 111: 457-462).

The passenger domain was expressed in *E. coli* BL21 (DE3) pLys cells (Invitrogen) using autoinduction (24 h at 29° C.). Cells were harvested and resuspended in 25 mM Tris pH 7, 150 mM NaCl, 0.5% Triton X-100, Protease Inhibitor Cocktail 3 (Astral Scientific) and DNAse (Sigma-Aldrich), and lysed by sonication. Lysate was cleared by centrifugation and loaded onto a HisTrap column (GE Healthcare). Protein was eluted in Buffer B (25 mM Tris-HCl pH 7, 150 mM NaCl, 0 to 500 mM imidazole). The purified TRX-histidine-tagged $\alpha^{43a}$ was cleaved using His-tagged TEV protease and dialyzed against Buffer C (25 mM HEPES-NaOH pH 7, 150 mM NaCl). After removing the His-tagged TEV protease and TRX-His$_6$-tag by further nickel affinity chromatography, Ag43a$^\alpha$ was purified to homogeneity by gel filtration chromatography (ÄKTA, GE Healthcare) using a Superdex S-75 (GE Healthcare) column pre-equilibrated in Buffer C. Protein purity was assessed by SDS-PAGE analysis.

Example 2: Structural and Functional Characterisation of Ag43a$^\alpha$

The structure of Ag43a$^\alpha$ was determined by single anomalous diffraction (SAD) and refined to an Rfree of 16.76% (R factor 21.56%) at 2.5 Å resolution. Briefly, purified Ag43a$^\alpha$ was equilibrated in Buffer B and concentrated to 18 mg mL$^{-1}$. Small stacked plate-like crystals were obtained from solutions comprising 2.8-2.9 M sodium malonate (pH 4). Following optimisation by additional screens (Hampton Research), larger stacked plate-like crystals (0.5×0.25×0.05 mm) were obtained in 2.8 M sodium malonate (pH 4) supplemented with 10 mM ATP. Diffraction data for SeMet Ag43a$^\alpha$ was collected at the 3BM1 protein crystallography beamline at the Australian Synchrotron. Images were collected at 1 degree oscillation for a total of 180° in the case of native crystals and 360° for SeMet Ag43a$^\alpha$. Native diffraction was indexed with XDS (Kabsch, Acta. Crystallogr. D Biol. Crystallogr. 2010. 66(Pt 2): 125-132) and scaled using SCALA (Evans, Acta. Crystallogr. D Biol. Crystallogr. 2006. 62(Pt 1): 72-82). SeMet data was integrated and scaled using HKL2000 (Otwinowski and Mino, Methods Enzymol. 1997. 276: 307-326).

The structure of Ag43a$^\alpha$ was solved by SAD phasing of the Ag43a$^\alpha$-SeMet derivative. Phase calculation, density modification and preliminary modelling were performed using PHENIX AutoSol and AutoBuild (Adams et al. Acta. Crystallogr. D Biol. Crystallogr. 2002. 58(Pt 11): 1948-1954). PHENIX AutoSol identified four Se atoms in the asymmetric unit, and the resulting phases were used in AutoBuild for automated building using Coot (Emsley and Cowtan, Acta. Crystallogr. D Biol. Crystallogr. 2004. 60(Pt 12 Pt 1): 2126-2132) and refined against the native 2.5 Å resolution dataset using phenix.refine (Adams et al. Acta. Crystallogr. D Biol. Crystallogr. 2002. 58(Pt 11): 1948-1954) and translation/libration/screw (TLS) refinement (Painter and Merritt, Acta. Crystallogr. D Biol. Crystallogr. 2006. 62(Pt 4): 439-459). The quality of the Ag43a$^\alpha$ model was assessed using MolProbity.

Structural analysis revealed that Ag43a$^\alpha$ folds into a three-stranded β-helix structure (FIG. 1A). Small-angle X-ray scattering data confirmed that the bent β-helix structure is representative of the structure observed in solution.

Ag43a$^\alpha$ oligomers were obtained by preparing crystallographically related subunits. Structural analysis revealed a tightly packed Ag43a$^\alpha$ dimer wherein the two twisted β-helical molecules coil around each other in a head-to-tail (trans) configuration (FIG. 1B). Protein Interfaces, Surfaces and Assemblies (PISA) analysis (Xu et al. J. Mol. Biol. 2008. 381(2): 487-507) demonstrated that each interface between the Ag43a$^\alpha$ molecules contained the following nine hydrogen bonds: N29-T256 (two hydrogen bonds), N60-T256, N60-T237, D79-1237, N96-R200, T97-R200, T98-R200 and G115-R200, as well as a salt bridge between the R59 and E216 side chains (FIG. 1C). In the full-length Ag43a sequence, these amino acid residues correspond to N83, R113, N114, D133, N150, T151, T152, G169, R254, E270, T291 and T310. Each Ag43a$^\alpha$ molecule comprises ladders of polar and charged residues at the N-terminal region of the edge joining faces 2 (F2) and 3 (F3) and the middle section of the F3 face, forming 18 hydrogen bonds and 2 salt bridges.

More complex oligomers were also identified, including assemblies of two pairs of dimers interacting via the N-terminal section of the F1-F2 edge. This secondary interaction (interface 2) is stabilised by van der Waals forces (FIG. 1D). Additionally, each Ag43a$^\alpha$ molecule interacts with a third Ag43a$^\alpha$ subunit via hydrogen bonding and hydrophobic interactions between the N-terminal region of the F3-F1 edge and the F2 face adjacent the structure-bending β-hairpin (interface 3). Interface 3 contains three hydrogen bonds (E38 (O)-K286 (NZ), N66 (ND2)-D288 (OD1), N66 (OD1)-K286 (NZ)) as well as van der Waals forces (FIG. 1D).

A mutant version of Ag43a was constructed in which seven amino acid residues located at the binding interface were substituted as follows: N29G, R59G, N60G, S78G, D79G, N96G, T98G. Referring to the full-length sequence of Ag43a, these substitutions correspond to N83G, R113G, N114G, S132G, D133G, N150G and T152G. Plasmid constructs carrying either the wild-type or mutant agn43 gene were transformed into an *E. coli* agn43 null strain (Kjaergaard et al. J Bacteriol. 2000. 182: 4789-4796), which is unable to form cell aggregations (Reisner et al. Mol. Mircrobiol. 2003. 48(4): 933-946). The transformed bacteria were examined by cell aggregation assays to determine whether the substituted residues are important for Ag43a-Ag43a association and bacterial aggregation. The assays demonstrated that the amino acid substitutions abolished Ag43a-mediated cell aggregation and that bacteria carrying the mutant version of Ag43a were indistinguishable from the strain lacking Ag43a (FIG. 1E). Western blot analysis of heat released proteins confirmed that the mutant version of Ag43a was highly expressed (FIG. 1E).

Example 3: Generation of Monoclonal Antibodies

Hybridoma Production

Mice were immunized with purified Ag43a passenger domain from UPEC strain CFT073 in the presence of Freund's adjuvant and confirmed serum response to target antigen by enzyme-linked immunosorbent assay (ELISA). Mouse spleen was removed and fused with SP2/0 myeloma cells according the the Kohler and Milstein method (Kohler and Milstein. Nature. 1975. 256: 495-497). Fused hybridoma supernatants were screened by ELISA against purified Ag43a passenger domain. Hybridoma cells of interest were subcloned to maintain their stability and monoclonal character by two rounds of limiting dilution subcloning. The resultant monoclonal hybridoma was grown and frozen for storage.

Identification of Autotransporter-Interacting Monoclonal Antibodies

MS1187 and MS1232 (Kjaergaard et al. J Bacteriol. 2000. 182: 4789-4796) were induced with 0.2% w/v L-arabinose grown in LB broth overnight shaking at 37° C. Both cell cultures were washed with 0.9% w/v NaCl, normalized to the same $OD_{600nm}$, followed by a mild heat treatment (60° C. for 30 min). Samples were centrifuged and supernatants were collected.

Hybridoma culture supernatants were screened for interaction with heat-released Ag43a passenger domain using ELISA. Briefly, Nunc MaxiSorp™ flat-bottom 96 well plates (eBioscience) were coated with heat-released Ag43a passenger domain, blocked with 1% w/v bovine serum albumin (BSA) and probed with hybridoma supernatants. Plates were washed and Ag43a$^\alpha$-interacting hybridoma culture supernatants were detected using alkaline phosphate-conjugated rabbit anti-mouse IgG (Sigma). The reaction was developed in the presence of alkaline phosphatase substrate (Sigma) and absorbance was read at 405 nm. Heat-released sample from *E. coli* harbouring empty pBAD/Myc-HisA was used as negative control.

Example 4: Inhibition of Bacterial Aggregation by Monoclonal Antibodies

Figure 2:
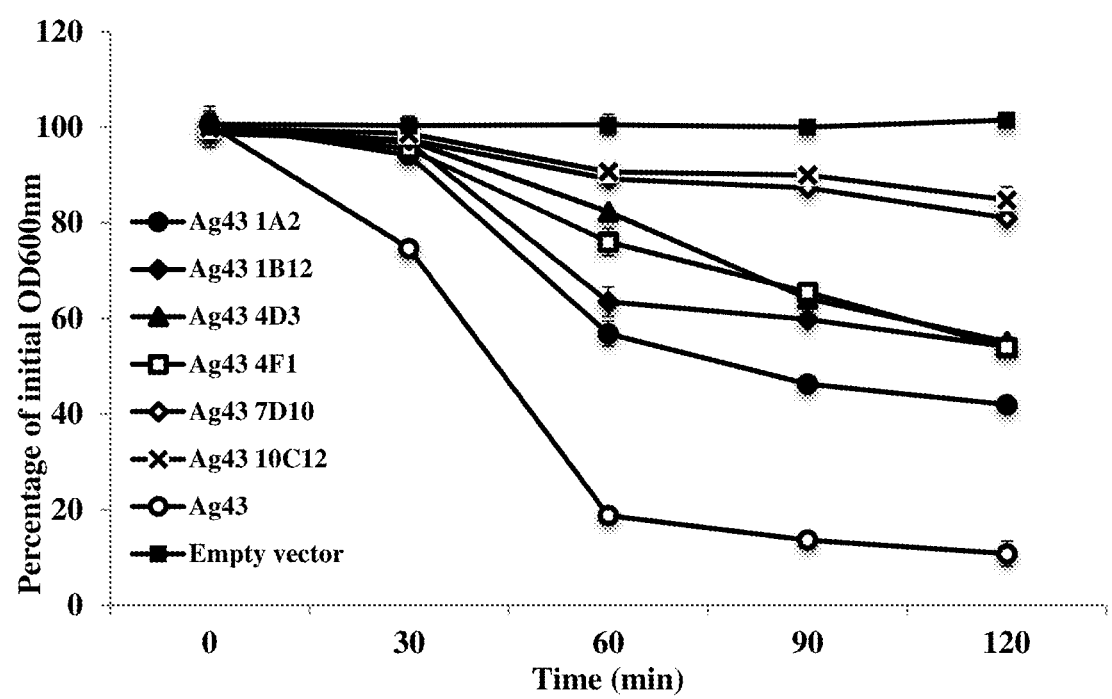
FIG. 2. Cell aggregation assay using supernatants from six different monoclonal antibody-expressing hybridomas.

Monoclonal antibody-containing hybridoma culture supernatant was added to bacterial cell suspensions with optical density at 600 nm ($OD_{600}$ nm) adjusted to 3. Cell aggregation was measured by sampling 100 μL aliquots from the upper part of each culture at 30 minute intervals and measuring the $OD_{600nm}$. Referring to FIG. 2, six monoclonal antibody-containing hybridoma culture supernatants were assayed and shown to be effective at inhibiting bacterial aggregation.

Example 5: Cloning, Expression and Purification of Fab Fragments

The sequence of the heavy and kappa chain variable regions was determined using cDNA generated from 10C12 hybridoma cells. Approximately $5 \times 10^6$ cells were pelleted and washed with phosphate-buffered saline (PBS). The cell pellet was resuspended in RNAlater® Stabilization Solution (AM7020, ThermoFisher Scientific) and RNA extraction was carried out using Trizol. cDNA was prepared using Oligo-dT primer.

PCR was performed using cDNA as template. A set of 4 degenerate forward primers for the heavy chain and 6 degenerate forward primers for the light chain were used, in conjunction with a reverse primer for the CH1 region of mouse IgG2b heavy chain, or to the constant region of mouse kappa chains. The forward primer sequences were based on those reported by Morrison (Morrison. Curr. Protocol. Immunol. 2002. Chapter 2: Unit 2. 12).

Once the variable region sequences were determined, the heavy chain variable region and Ch1 region was amplified from cDNA using mVh1_For primer (accgccaccggtgtcactccCAGGTCCAACTGCAGCAGCC) (SEQ ID NO: 37) and mG2b_Ch1_Rev primer (gggccctctagattagtgatggtgatggtgatgaagttttttgtccaccgtggtgc) (SEQ ID NO: 38), incorporating part of a mammalian secretion signal in the forward primer, and a 6×His tag and stop codon in the reverse primer, and restriction sites for cloning. The PCR product was cloned into pcDNA3.1 vector into which a mammalian secretion signal had previously been cloned. Similarly, the complete kappa chain was amplified from cDNA using mVk6_For primer (accgccaccggtgtccactccAGTATTGTGATGACCCAGACTCCC) (SEQ ID NO: 39) and mKappa_Rev primer (gggccctctagattaACACTCATTCCTGTTGAAGCTCTTG) (SEQ ID NO: 40). Only the heavy chain contained a 6×His tag addition.

Figure 3:
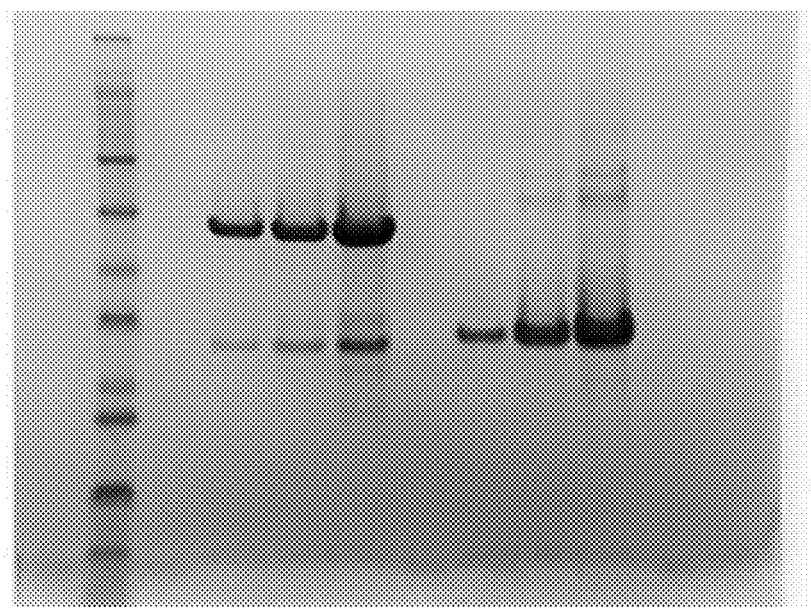
FIG. 3. SDS-PAGE of purified Fab10C12. Lane 2: SeeBlue Plus2 marker. Lanes 4-6: non-reduced Fab10C12 (2.5 μg, 5 μg, 10 μg). Lanes 8-10: reduced Fab10C12 (2.5 μg, 5 μg, 10 μg).

The heavy and light chain expression vectors were co-transfected at 1:1 ratio into CHO-XL99 cells (Acyte Biotech) using polyethyleneimine (PEI) mediated transfection, in either Expi-CHO (Gibco) or CD-CHO (Gibco) media. The culture supernatant was harvested 10-14 days post-transfection, when cell viability dropped below 80%. The 10C12 Fab was purified by immobilised metal affinity chromatography using HisTrap Excel 5 mL column (GE Healthcare). After loading, the column was washed with 20 mM sodium phosphate, 500 mM sodium chloride containing 20 mM imidazole, followed by a wash with the same buffer containing 40 mM imidazole. The protein was eluted using the same buffer containing 500 mM imidazole. The eluted protein was buffer-exchanged into 25 mM Tris, 150 mM NaCl, pH 7, and then further purified using cation exchange on a Mono-S column (GE Healthcare) (FIG. 3). Similar methods were used to express and purify the 7D10 Fab.

Example 6: Inhibition of Bacterial Aggregation by Isolated Fab Molecules

Figure 4:
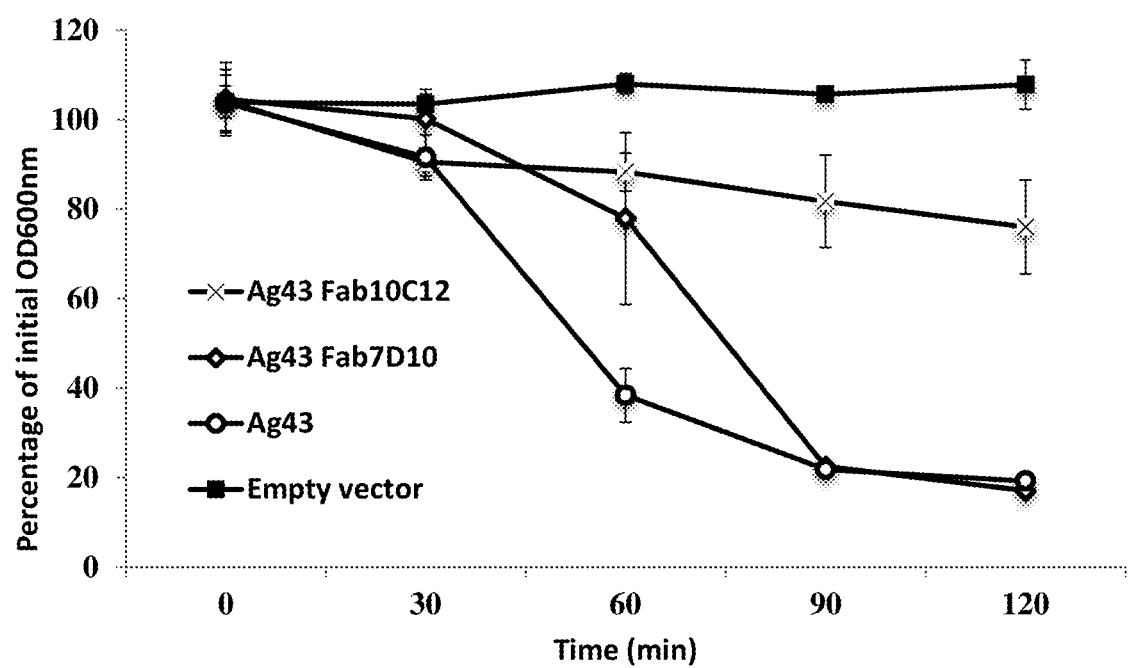
FIG. 4. Bacterial cell aggregation assay using the agn43 null strain MS427 transformed with an empty vector or a vector expressing wild-type Ag43a. Addition of purified Fab7D10 and Fab10C12 to cells expressing wild-type Ag43a suppressed bacterial aggregation.

Cell aggregation assays were performed as described above to determine whether isolated 10C12 and 7D10 could inhibit bacterial aggregation. The optical density of agn43 null mutants harbouring an empty vector remained unchanged, whereas the optical density of E. coli cells expressing Ag43 decreased over time due to Ag43-mediated aggregation and bacterial sedimentation (FIG. 4). 10C12 and 7D10 were both able to reduce aggregation of cells expressing Ag43 (FIG. 4).

Figure 5:
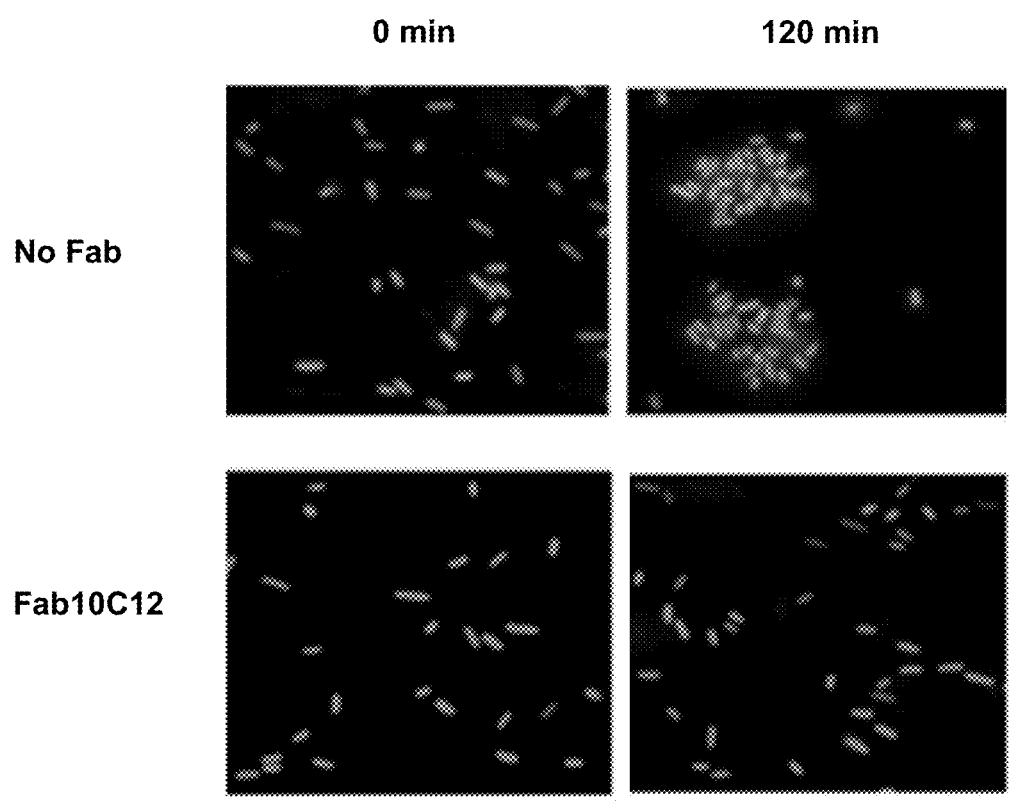
FIG. 5. Light microscope images of fluorescently tagged *E. coli* expressing Ag43a taken at 0 and 120 minutes. Over time, *E. coli* expressing Ag43a clump and aggregate (upper panels). Addition of 10 μg/mL of purified Fab10C12 inhibits bacterial aggregation (lower panels).

M5427 (agn43 null) strain chromosomally tagged with yfp encoding yellow fluorescence protein (YFP) carrying pCO4 (Heras et al. Proc. Natl. Acad. Sci. USA. 2014. 111: 457-462) were grown overnight in LB broth supplemented with the appropriate antibiotics and 0.2% (w/v) L-arabinose. The following day, the cultures were adjusted to an $OD_{600}$ of 3, and 1 mL of the bacterial suspension was added to a separate 2 mL tube. Ten µg/mL of purified Fab10C12 or sterile PBS was added to the tubes, and the cells were left to stand at room temperature. To monitor for aggregation, 5 µL of cells were removed from the upper half of the culture at 30-minute intervals and spotted onto glass slides for microscopy. Detection of the YFP-tagged cells was performed on an epifluorescent light microscope (ZEISS Axioplan 2) equipped with detectors and filters for monitoring YFP. Images were further processed for display using ImageJ software (Schneider et al. Nat. Methods. 2012. 9: 671-675). The fluorescent microscopy assays further demonstrated that Fab10C12 inhibits bacterial aggregation (FIG. 5).

Example 7: Ag43a$^\alpha$-Fab Binding Assays

Figure 6:
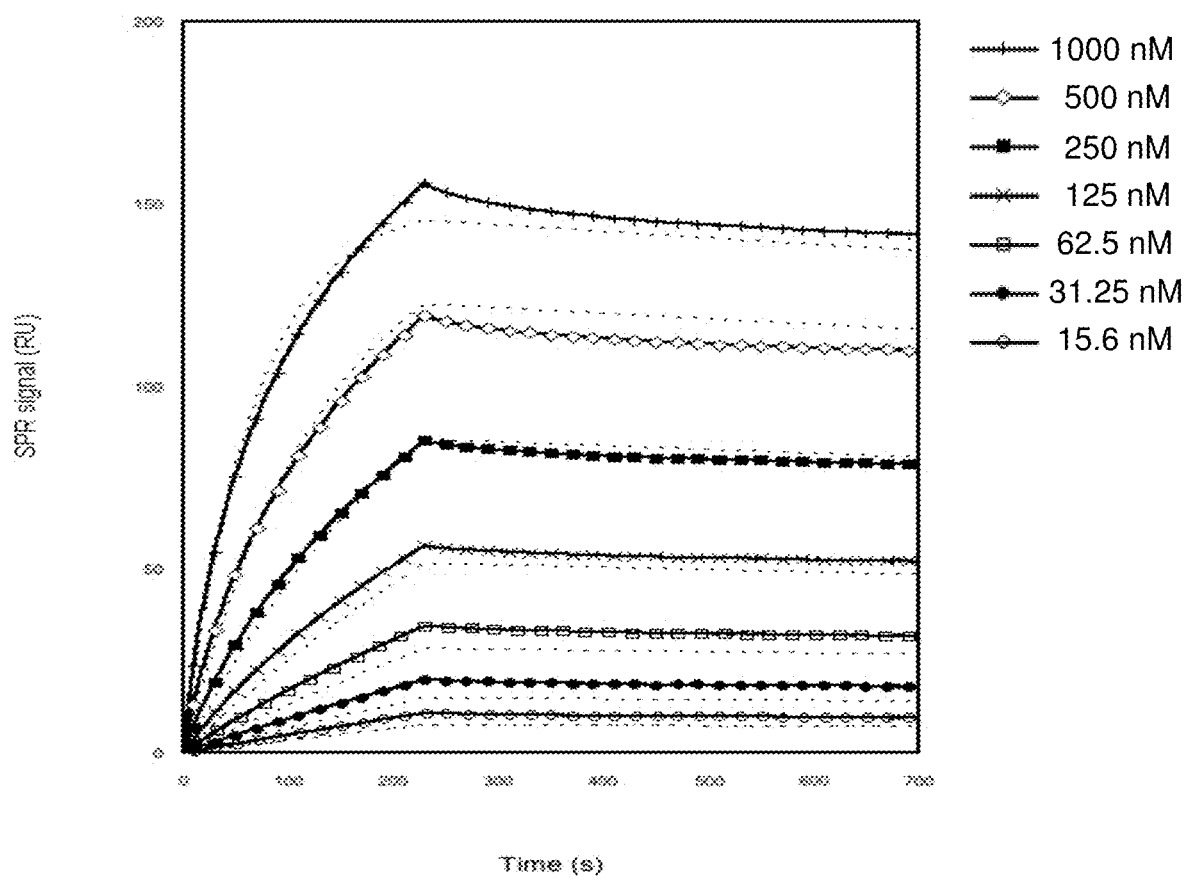
FIG. 6. Surface plasmon resonance (SPR) assays of immobilised Fab10C12 with increasing concentrations of Ag43a$^\alpha$ ranging from 15.6 nM to 1000 nM ($K_D$=7.28 nM).

A Biacore T200 biosensor instrument was used to measure the affinity of the interaction of Ag43a$^\alpha$ with Fab10C12. Fab10C12 was immobilized onto a CM5 chip at a level of 500-1000 RU using amine coupling. Surface plasmon resonance (SPR) experiments were performed at 25° C. using HBS-EP (10 mM HEPES, pH 7.4, 150 mM NaCl, 3.4 mM EDTA, and 0.005% P20) as the running buffer. To generate binding data, Ag43a$^\alpha$ at concentrations ranging from 15.6 nM to 1000 nM was injected over immobilized Fab at a constant flow rate of 90 mL/min for 230 s; Ag43a$^\alpha$ dissociation was monitored by flowing running buffer at 90 mL/min for 600 s. The surface was regenerated after each cycle by injecting 10 mM glycine/HCl at pH 2.0. Kinetic analysis was carried out using the Biacore T200 evaluation software. The $K_D$ was calculated at 7.28 nM±0.98 nM expressed as mean±standard error of the means (SEM). Experiments were conducted on three independent occasions with fresh immobilization (FIG. 6).

Example 8: Analytical Ultracentrifugation of Ag43a$^\alpha$-Fab Complex

Figure 7:
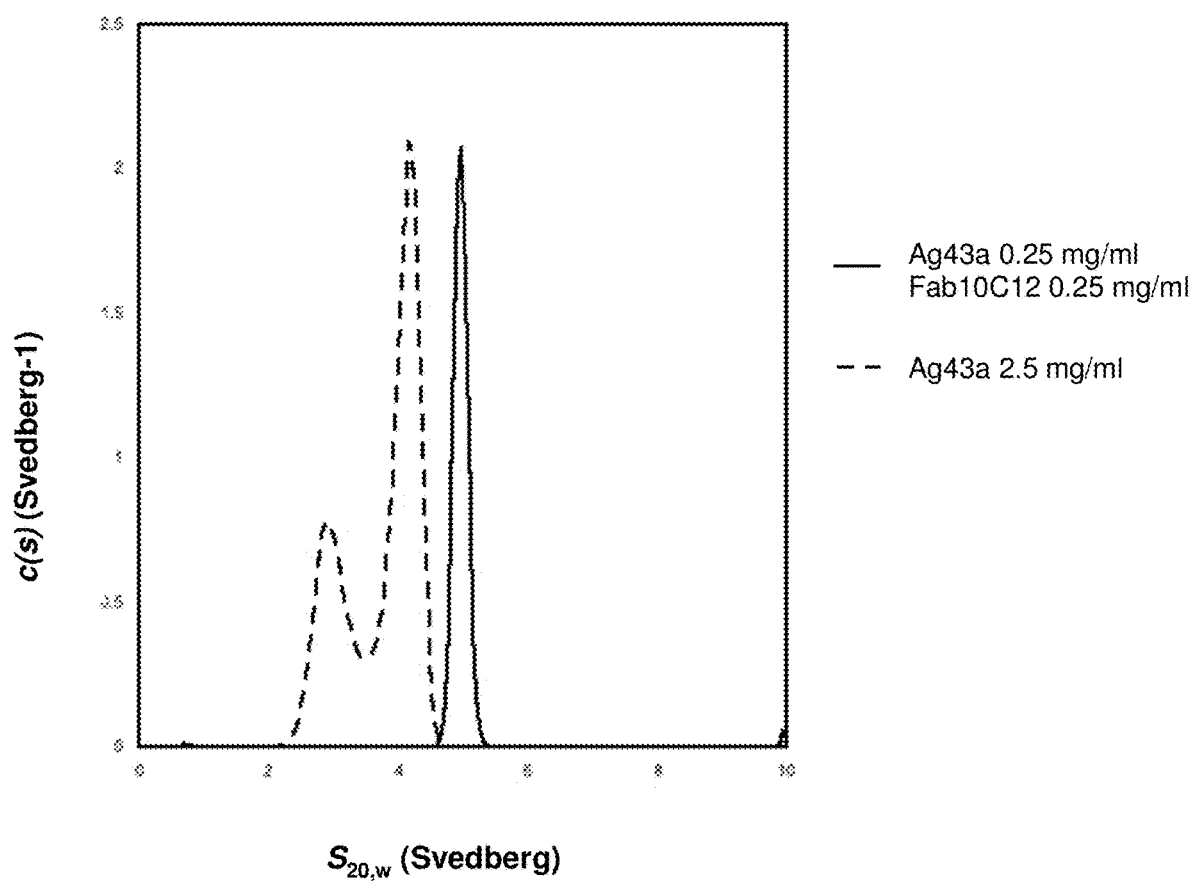
FIG. 7. Analytical ultracentrifugation of Ag43$^\alpha$, and Ag43a$^\alpha$ plus Fab10C12.

Sedimentation velocity experiments were performed in a Beckman Coulter model XL-I analytical ultracentrifuge with a An50-Ti rotor. Double-sector quartz cells were loaded with 400 µl of buffer (25 mM Hepes 150 mM NaCl pH 7.0) and 380 µl of 0.25 and 2.5 mg/ml Ag43a$^\alpha$ along with 0.25 mg/ml each of Ag43a$^\alpha$ and Fab10C12. Initial scans were performed at 3,000 rpm to determine the optimal wavelength and radial positions. Absorbance readings were collected at 280 nm and 40,000 rpm at 20° C. Solvent density, solvent viscosity and estimates of the partial specific volume of Ag43a$^\alpha$ (0.7194 ml/g) at 20° C. were calculated with SEDNTERP. Data were analysed using c(s) and c(M) with SEDFIT. Ag43a$^\alpha$ at 0.25 and 2.5 mg/ml generated standardised sedimentation coefficients of 3 and 4 S consistent with its monomeric and dimeric forms. However, the 0.25 mg/ml of Ag43a$^\alpha$ and Fab10C12 sample produced a single and distinct sedimentation coefficient of 5 S with a significant drop in frictional ratio from 1.45 to 1.13, demonstrating the formation of Ag43a$^\alpha$-Fab10C12 complex (FIG. 7).

Example 9: Inhibition of Biofilm Formation

Static biofilm formation was assayed as described by O'Toole and Kolter (O'Toole and Kolter. Mol. Microbiol. 1998. 28: 449-461). Briefly, an overnight culture of MS427 pCO4:ag43 was diluted 1/1000 with fresh LB medium supplemented with 0.2% (w/v) L-arabinose and incubated in a 96-well microtiter plate (Grenier Bio-One, 655101) overnight at 28° C. Wells were then washed twice with PBS and stained with 0.1% (w/v) crystal violet. Following three PBS washes, biofilm-adsorbed crystal violet was extracted in 150 µL ethanol and quantified by absorbance at 595 nm. MS427 pCO4:ag43 without Fab10C12 was used as a positive control. MS427 pBAD/Myc-His A was used as a negative control.

Figure 8:
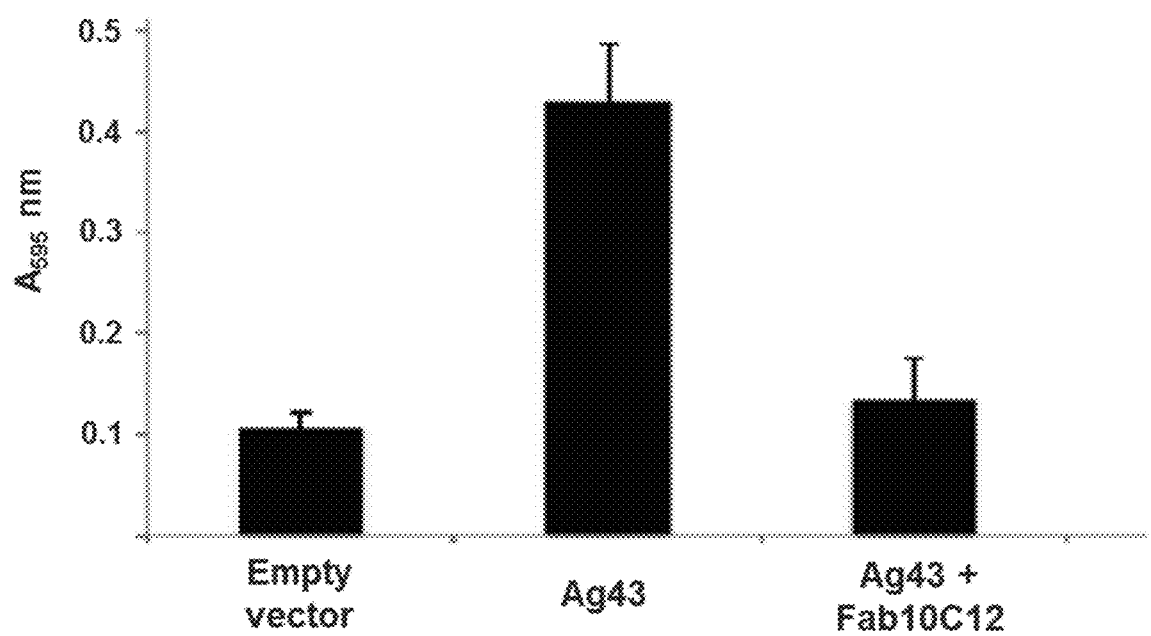
FIG. 8. Biofilm formation assay using the agn43 null strain MS427 expressing Ag43a. Substantial biofilm formation was observed in bacteria expressing Ag43a alone (Ag43). Addition of Fab10C12 inhibited biofilm formation (Ag43+Fab10C12).

Biofilm formation is detected by uptake of crystal violet and absorbance at $A_{595}$ nm. E. coli expressing Ag43a aggregate over time leading to biofilm formation and high absorbance at $A_{595}$ nm. Addition of Fab10C12 greatly reduced biofilm formation (FIG. 8).

Example 10: Structural Characterisation of Ag43a$^\alpha$-Fab Complex

Figure 9:
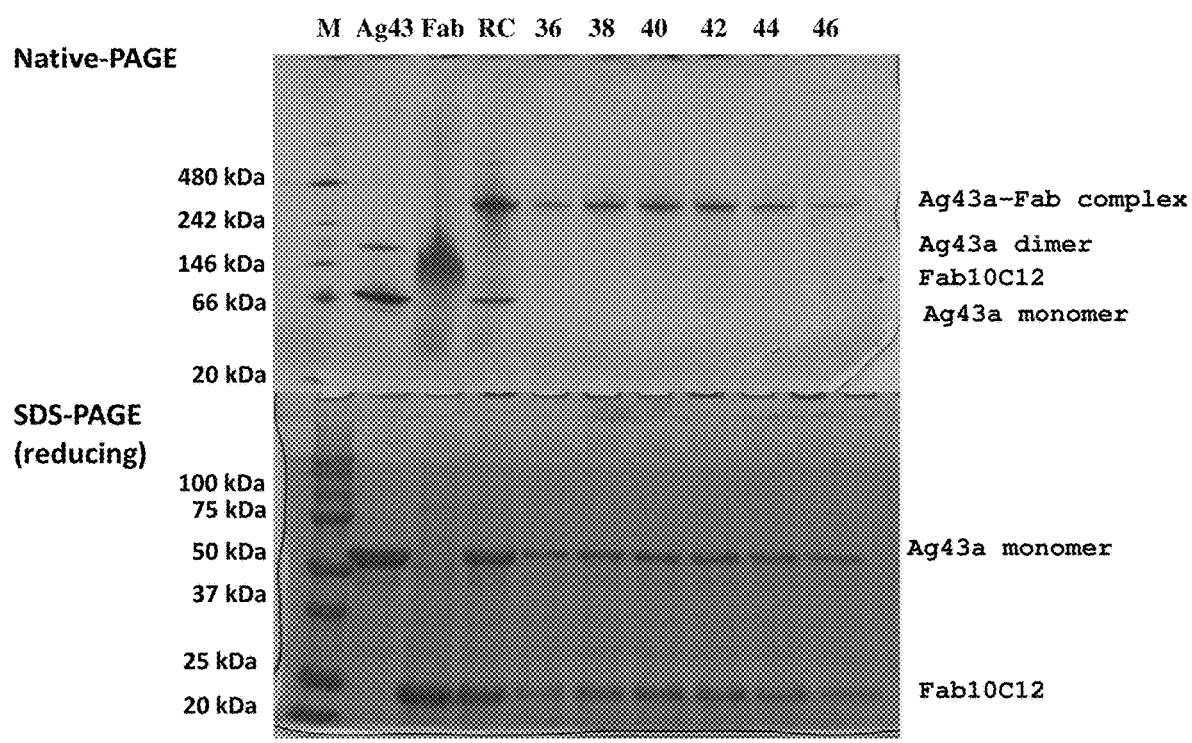
FIG. 9. Ag43a$^\alpha$-Fab10C12 complex formation monitored by Native-PAGE and SDS-PAGE. Ag43a$^\alpha$ (Ag43) and Fab10C12 (Fab) were mixed (RC) and run through a Superx S-75 column (fractions 36, 38, 40, 42, 44 and 46).

Purified Fab10C12 and Ag43a$^\alpha$ were mixed in a 1.0:1.0 molar ratio for 2 hours at room temperature on ice in 25 mM HEPES-NaOH pH 7, 50 mM NaCl. The mixture was then applied to a Superdex S-75 GE Healthcare column to remove any residual monomeric protein. Complex formation and chromatography fractions were analysed by 12% SDS-PAGE under reducing conditions along with Native-PAGE (FIG. 9). Fractions containing Ag43a$^\alpha$-Fab10C12 complex were pooled and concentrated to 18 mg/ml for protein crystallization experiments.

Figure 10:
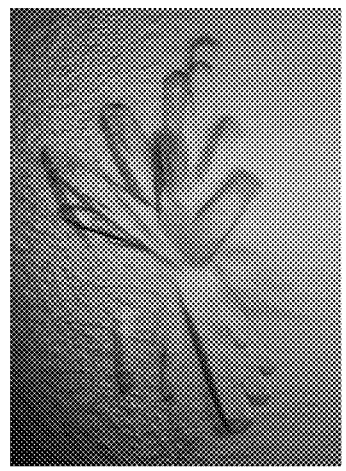
FIG. 10. Structural analysis of Ag43a$^\alpha$-Fab10C12 complex. A. Ag43a$^\alpha$-Fab10C12 crystals. B. Ribbon structure of Ag43a$^\alpha$-Fab10C12 complex. C. Model illustrating the head-to-tail interaction between Ag43a which promotes bacterial aggregation (upper panel) and the disruption of that interaction caused by Ag43a-binding molecules such as Fab10C12.
Figure 10:
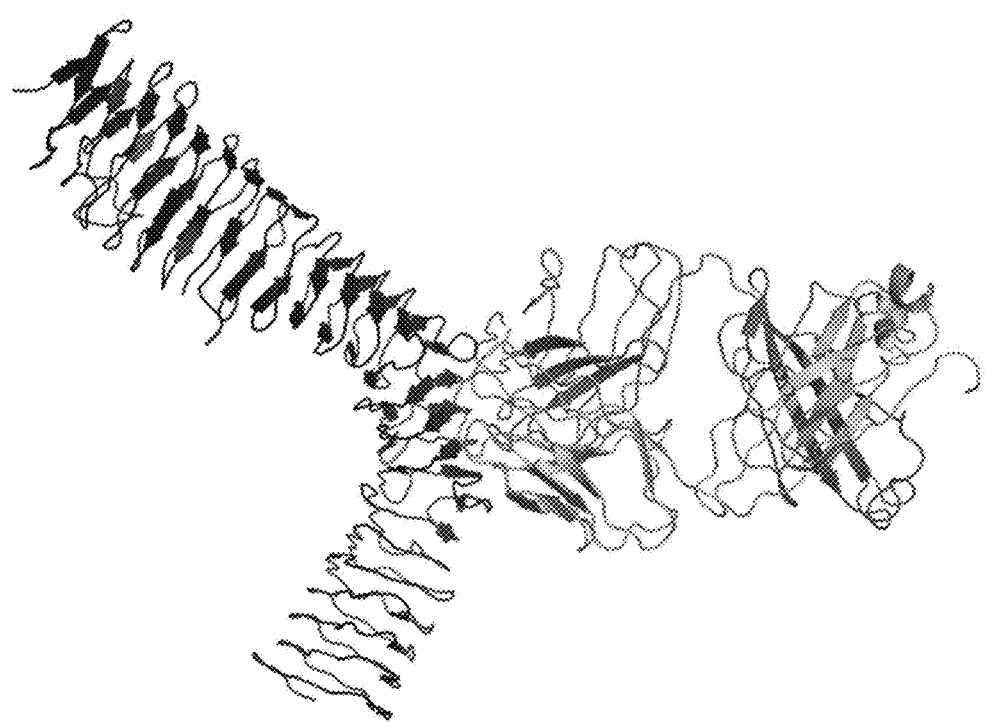
Figure 10:
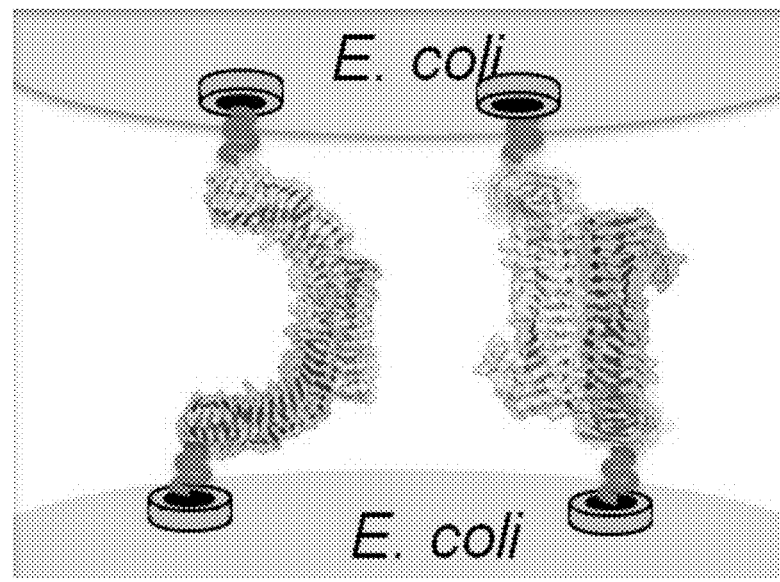
Figure 10:
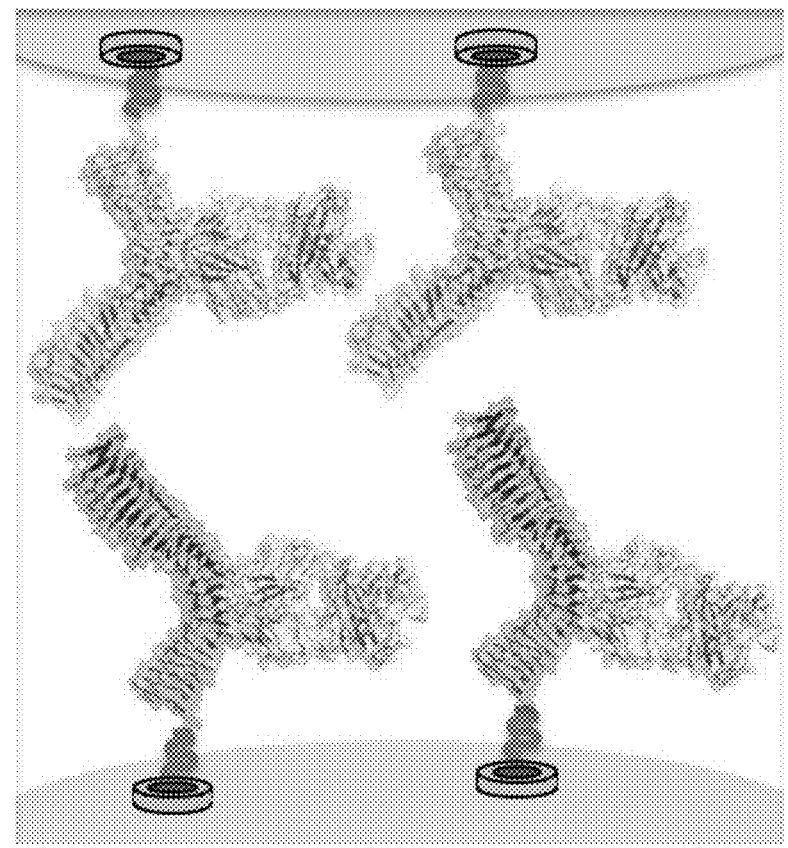

Diffraction quality crystals grew from reservoir solutions containing 0.1 M sodium citrate pH 6.1, 0.5 M ammonium sulfate and 0.8 M lithium sulfate (FIG. 10A). Crystals were cryoprotected in reservoir solution with lithium sulfate concentration increased to 2.4 M. Data was collected at a wavelength of 0.9537 Å on an ADSC Q315r CCD detector on the MX2 micro-crystallography beamline at the Australian Synchrotron. As a result of high solvent content, diffraction was weak (>3.5 angstrom) and attenuation was reduced to 30%. In order to maximise signal and data quality along with reduced radiation damage, a total of three datasets (900° total) were used in structure determination. Imosflm (Battye et al. Act. Cryst. 2011. D67: 271-281) was used to individually index and integrate the datasets separately. Datasets were assessed for isomorphism using the program BLEND (Foadi et al. Acta. Cryst. 2013. D69: 1617-1632), and then scaled, truncated and merged using AIMLESS (Evans and Murshudov. Acta. Cryst. 2013. D69: 1204-1214). Data was processed to 3.5 Å resolution with a spacegroup of $P4_12_12$ with unit cell dimensions 274.50, 274.50, 168.81 Å and 90.0, 90.0, 90.0 degrees.

The Ag43a$^\alpha$-Fab10C12 complex structure was solved by molecular replacement with Phaser (McCoy et al. J. Appl. Crystallogr. 2007. 40: 658-674) using the structure of Ag43a (PBD: 4KH3) and the 7F11 Monoclonal Fab Fragment (PDB: 3G19, chains L and H) (Shaffer et al. Science. 2009. 325(5943): 1010-1014). The model underwent refinement using Refmac5 (Murshudov et al. Acta. Crystallogr. D Biol. Crystallogr. 2011. 67: 355-367) further phasing with Phaser along with model building using COOT (Emsley and Cowtan. Acta. Crystallogr. D Biol. Crystallogr. 2004. 60: 2121-2132) and Phenix Autobuild (Adams et al. Acta. Cryst. 2010. D66: 213-221). The quality of the model was monitored during refinement by the Rfree value, which represented 5% of the data. The final model comprises 2 Ag43a$^\alpha$-Fab10C12 complexes per asymmetric unit. The structure revealed the molecular interactions between Ag43a$^\alpha$ and Fab10C12 (FIG. 10B).

Whereas the head-to-tail interaction between Ag43a normally promotes bacterial aggregation and biofilm formation (FIG. 10C; upper panel), Fab10C12 binds to Ag43a and thereby blocks this interaction (FIG. 10C; lower panel), inhibiting bacterial aggregation and biofilm formation.

Example 11: Epitope Mapping

The structure of the Ag43a$^\alpha$-Fab10C12 complex was analysed using COOT. Amino acids that directly contribute to Ag43$^\alpha$-Fab10C12 binding were identified where compatible side chains at the interface were within hydrogen bonding distance of each other. This analysis revealed the following epitope residues in Ag43a: R330, G332, A333, S335, T361, N362, R364, T380, T381, S383, N386, S399, T401, D404 and G405.

Figure 11:
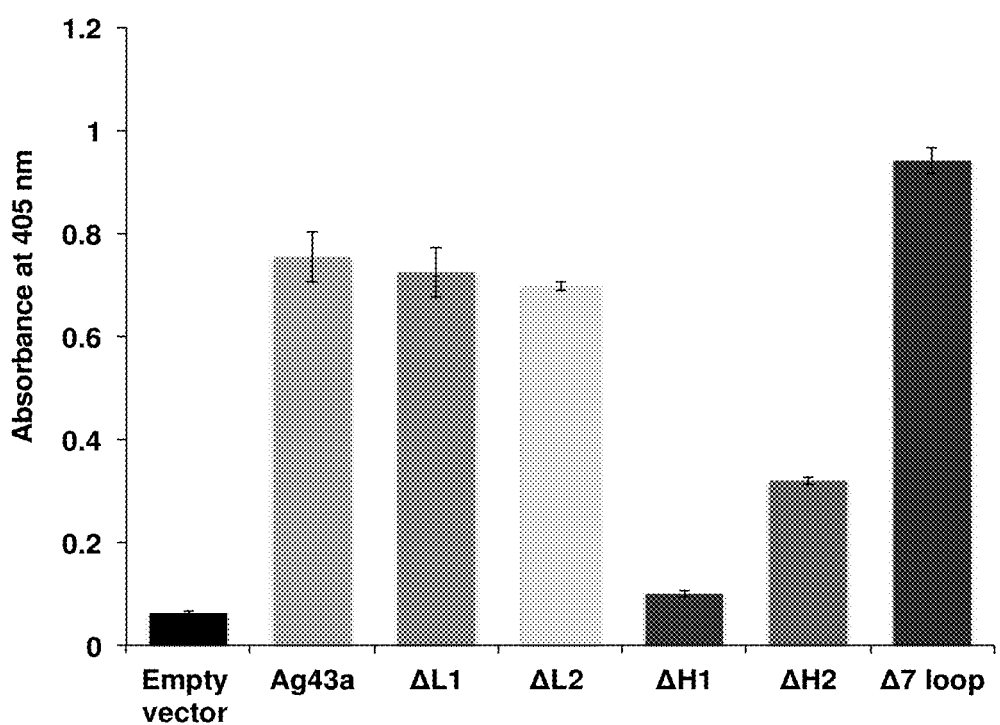
FIG. 11. Whole cell ELISA of mAb10C12 against various Ag43a$^\alpha$ mutants.

A whole cell ELISA was then performed in order to assay the ability of the 10012 monoclonal antibody to bind to various Ag43a mutants. Among the Ag43a mutants assayed was a A7 loop mutant which comprised amino acid substitutions in the Ag43a$^\alpha$ interface 1 loops (referring to the full-length protein: N83G, R113G, N114G, S132G, D133G, N150G, T152G; referring to the passenger domain: N29G, R59G, N60G, S78G, D79G, N96G, T98G), none of which affected the identified epitopic residues. ELISA confirmed that the A7 loop mutations did not diminish binding between Ag43a$^\alpha$ and mAb10C12 (FIG. 11).

Two further mutants were constructed in which residues in loop 1 (ΔL1: LELGPDSDENT [SEQ ID NO: 27]) and loop 2 (ΔL2: AEGGPESENVS [SEQ ID NO: 28]) were deleted. Neither deletion disrupted the identified epitopic residues, and neither mutant diminished the binding between Ag43a$^\alpha$ and mAb10C12 (FIG. 11).

Two further mutants were constructed in which residues in the L-shaped bend were deleted (ΔH1: AATVTGTNRL-GAFSVVA [SEQ ID NO: 29] and ΔH2: GAAVSGTRSDGKAFSIG [SEQ ID NO: 30]). Both deletions removed epitopic residues. Specifically, ΔH1 deleted epitopic residues R330, G332, A333 and S335, and ΔH2 deleted epitopic residues S399, T401, D404 and G405. Both the ΔH1 and ΔH2 deletions significantly impaired the binding between Ag43a$^\alpha$ and mAb10C12 confirming that the identified residues are epitopic (FIG. 11).

Example 12: Conserved Self-Association Mechanism Among Autotransporter Adhesins

The amino acid sequence of Ag43 from UPEC strain UTI189 is set forth as SEQ ID NO: 31, and its passenger domain is set forth as SEQ ID NO: 32. The amino acid sequence of Ag43 from *E. coli* strain EDL933 is set forth as SEQ ID NO: 33, and its passenger domain is set forth as SEQ ID NO: 34. The amino acid sequence of TibA from the enterotoxigenic *E. coli* strain H10407 is set forth as SEQ ID NO: 35, and its passenger domain is set forth as SEQ ID NO: 36. The amino acid sequence of Ag43b from UPEC strain CFT073 is set forth as SEQ ID NO: 41, and its passenger domain is set forth as SEQ ID NO: 42. All four autotransporters mediate bacterial aggregation and biofilm formation. The passenger domain of each autotransporter was expressed and crystallised using methods similar to those outlined in Examples 1 and 2. Briefly, the coding sequence for the α domain of each autotransporter was cloned into a LicE expression vector. The proteins were expressed in *E. coli* BL21 (DE3) pLysS or *E. coli* C41 (DE3) cells by autoinduction for 24 hours at 30° C. All four proteins were purified by nickel affinity chromatography and after removal of the N-terminal tag by cleavage with tobacco etch virus (TEV) protease, proteins were purified to homogeneity by reverse nickel affinity followed by gel filtration chromatography.

Figure 12:
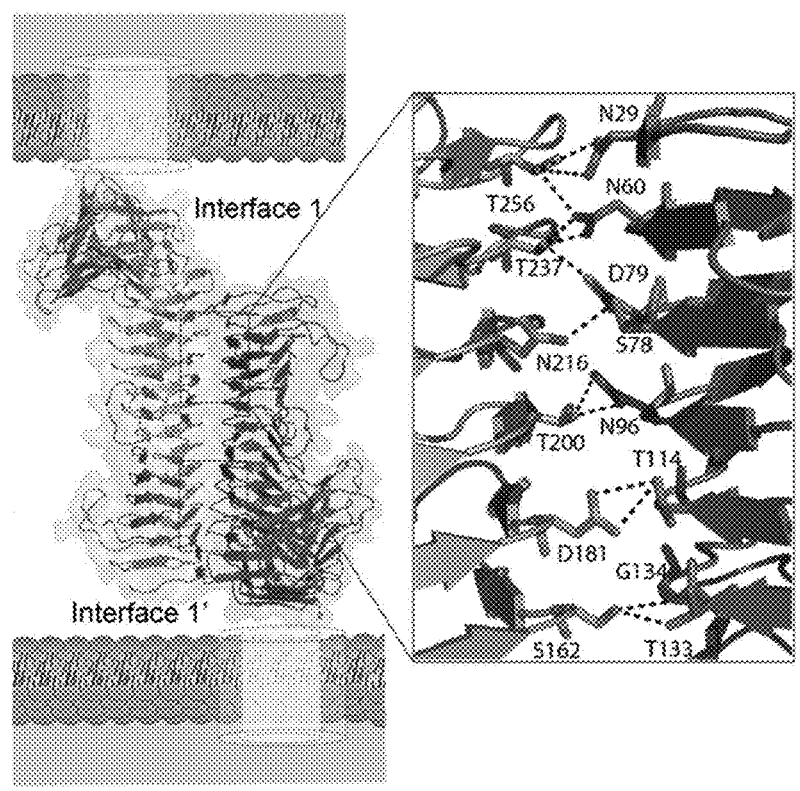
FIG. 12. Structural and functional analysis of autotransporter homodimers. A. Ribbon structure of Ag43$^\alpha$ homodimer from enterohemorrhagic *E. coli* EDL933. B. Ribbon structure of Ag43$^\alpha$ homodimer from uropathogenic *E. coli* UTI189. C. Ribbon structure of Ag43b$^\alpha$ homodimer from uropathogenic *E. coli* CFT073. D. Ribbon structure of TibA$^\alpha$ homodimer from enterotoxigenic *E. coli* H10407 E. Cell aggregation assay using CFT073 expressing either wild type Ag43b or an interface mutant version of Ag43b comprising the following substitutions: D133(29)G, N164(60)G, R166(62)G, D183(79)G, S199(95)G, S217(113)G. Expression of wild type and mutant Ag43b was confirmed by Western analysis (inset). F. Cell aggregation assay using EDL933 expressing either wild type Ag43 or a double interface mutant version of Ag43 comprising the following substitutions: D233(181)G T252(200)G T289(237)G T308 (256)G. Expression of wild type and mutant Ag43 was confirmed by Western analysis (inset). G. Cell aggregation assay using UTI189 expressing either wild type Ag43 or an interface mutant version of Ag43 comprising the following substitutions: T84(32)G, N112(60)G, D131(79)G, T132(80) G, T150(98)G, N152(100)G, N189(137)G. Expression of wild type and mutant Ag43 was confirmed by Western analysis (inset).
Figure 12:
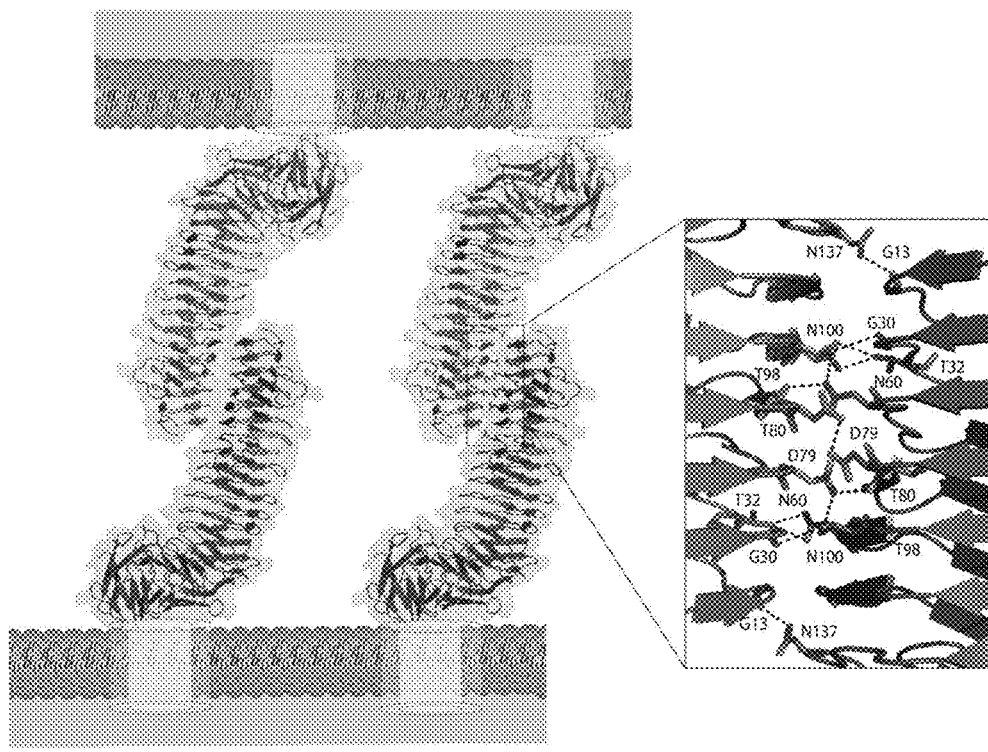
Figure 12:
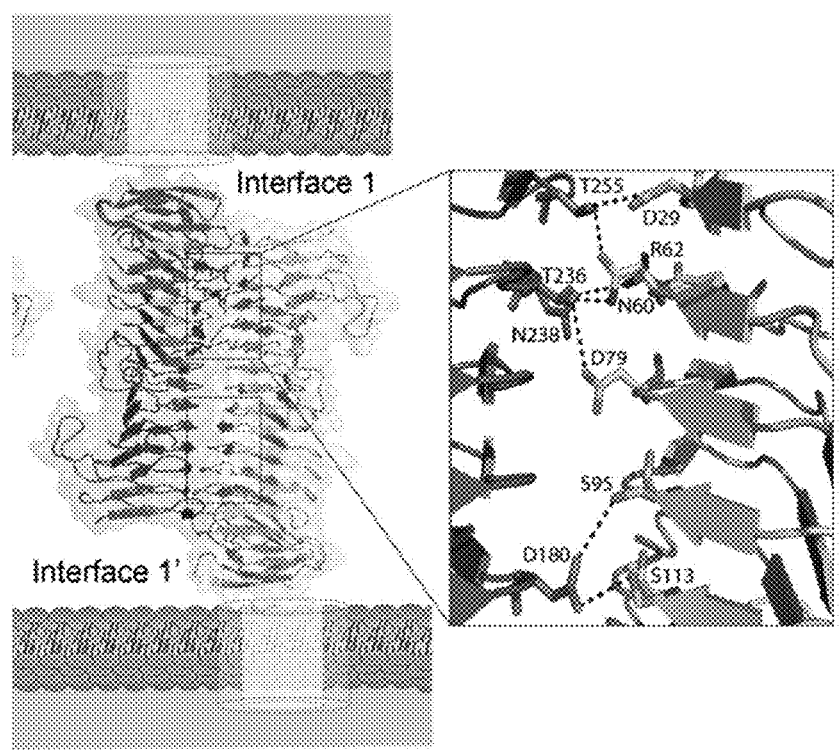
Figure 12:
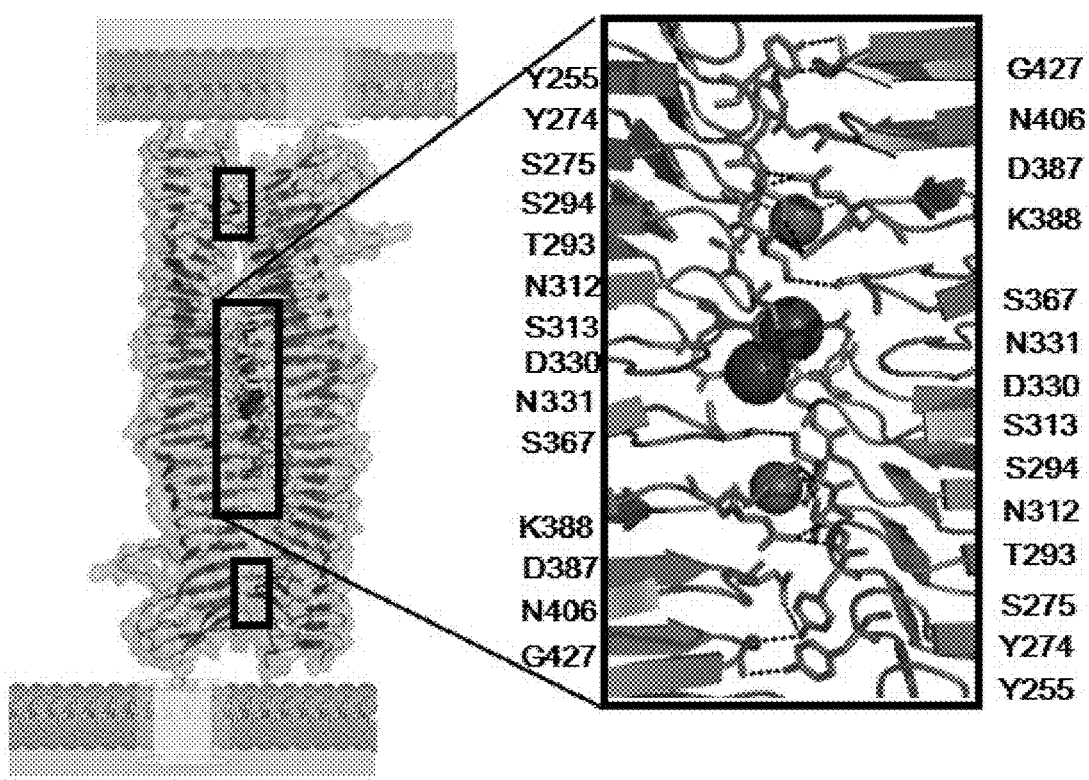
Figure 12:
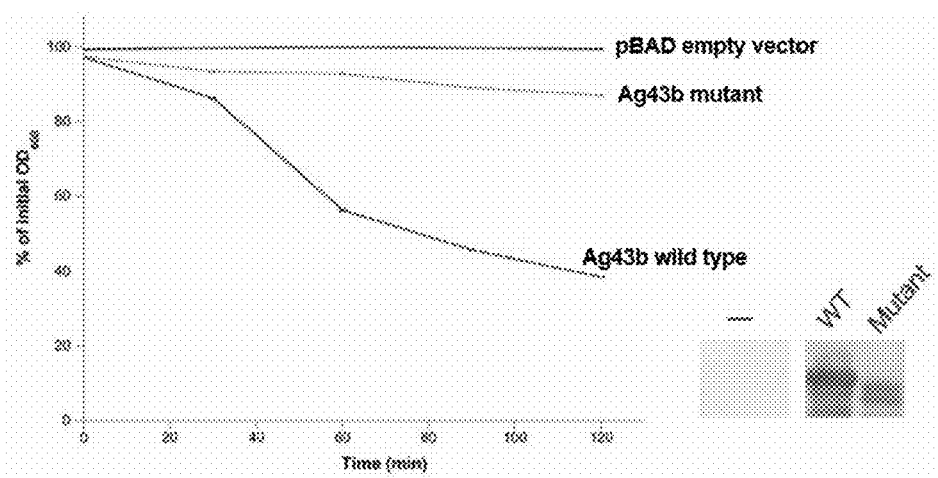
Figure 12:
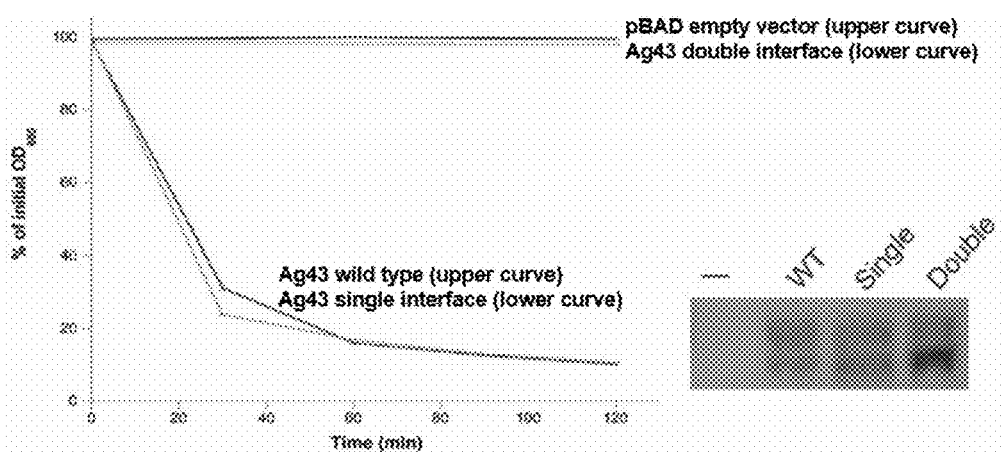
Figure 12:
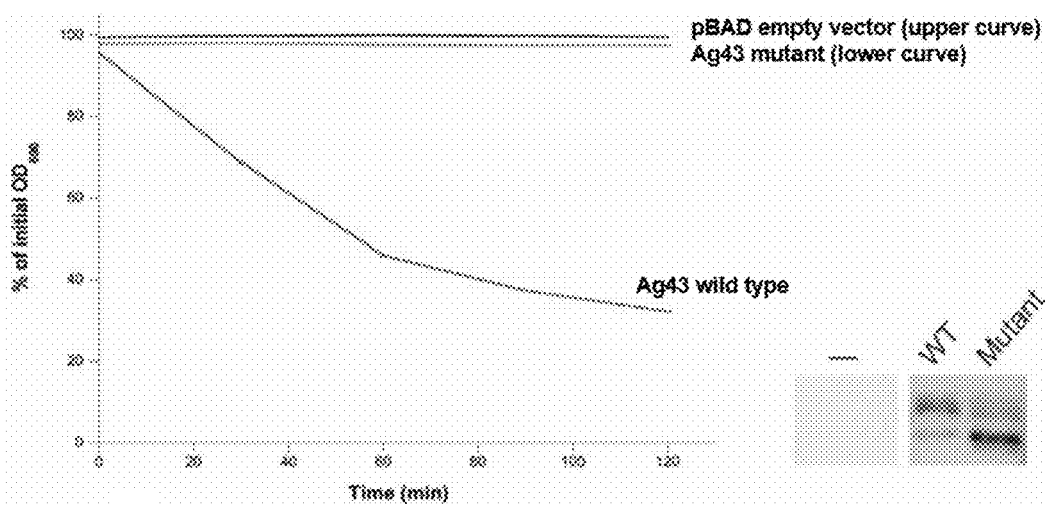

Ag43$_{UTI89}$$^\alpha$ and Ag43$_{EDL933}$$^\alpha$ were crystallised in 20% 2-propanol, 100 mM trisodium citrate/citric acid pH 5.2, 20% PEG 4000 and 100 mM MMT (DL-malic acid, MES monohydrate, Tris base) pH 7.8-8.4, 18-28% PEG 1500, respectively. Ag43b$_{CFT073}$$^\alpha$ was crystallised in 100 mM Na cacodylate pH 6.4, 14% PEG 4000, 20% MPD. TibA was crystallised in 100 mM sodium acetate pH 4.4, 24% PEG 6000, 200 mM calcium chloride. All four passenger domains formed tightly packed homodimers wherein the two twisted β-helical molecules associate with each other in a head-to-tail (trans) configuration (FIG. 12). Molecular packing in the crystals of Ag43$_{UTI89}$$^\alpha$ and TibA revealed packed dimers wherein the two twisted β-helical molecules associate with each other in a head-to-tail (trans) configuration. These crystallographic interfaces were confirmed to be the biological interfaces by site-directed mutagenesis of the residues at the interfaces and functional characterisation in cell aggregation assays (FIG. 12). Mutagenesis and functional studies informed by the Ag43$_{EDL933}$$^\alpha$ dimers confirmed that this autotransporter adhesin also oligomerises in a head-to-tail (trans) configuration which is stabilise by two interfaces, similar to that observed in the Ag43a$^\alpha$ dimers.

Referring to the sequence of full-length Ag43 from EDL933 (SEQ ID NO: 33), the following interface residues were identified at the binding surface: N81, N112, D131, S130, N148, T166, T185, G186, S214, D233, T252, N268, T289 and T308 corresponding to residues N29, N60, D79, S78, N96, I114, I133, G134, S162, D181 and I200 of the passenger domain (SEQ ID NO: 34). Referring to the sequence of full-length Ag43 from UTIi 89 (SEQ ID NO: 31), the following interface residues were identified at the binding surface: G65, G82, I84, N112, D131, T132, T150, N152 and N189, corresponding to residues G13, G30, T32, N60, D79, I80, T98, N100 and N137 of the passenger domain (SEQ ID NO: 32). Referring to the sequence of full-length TibA from H10407 (SEQ ID NO: 35), the following residues were identified at the binding surface: T118, T137, S154, Y255, Y274, S275, T293, S294, N312, S313, D330, N331, S367, K388, D387, N406, G427, N565 and D597. Referring to the sequence of full-length Ag43b from CFT073 (SEQ ID NO: 41), the following interface residues were identified at the binding interface: D133, N164, R166, D183, S199, S217, D284, I340, N342 and T359 corresponding to residues D29, N60, R62, D79, S95, S113, D180, T236, N238 and T255 of the passenger domain (SEQ ID NO: 42).

All four autotransporter passenger domains homodimerised in a conserved head-to-tail configuration (FIG. 12). This conserved mechanism of interaction may therefore be disrupted using antibodies or antigen binding fragments thereof generated using the methods described above (eg, Example 3).

Example 13: Broad Spectrum Activity of Fab Fragment

Figure 13:
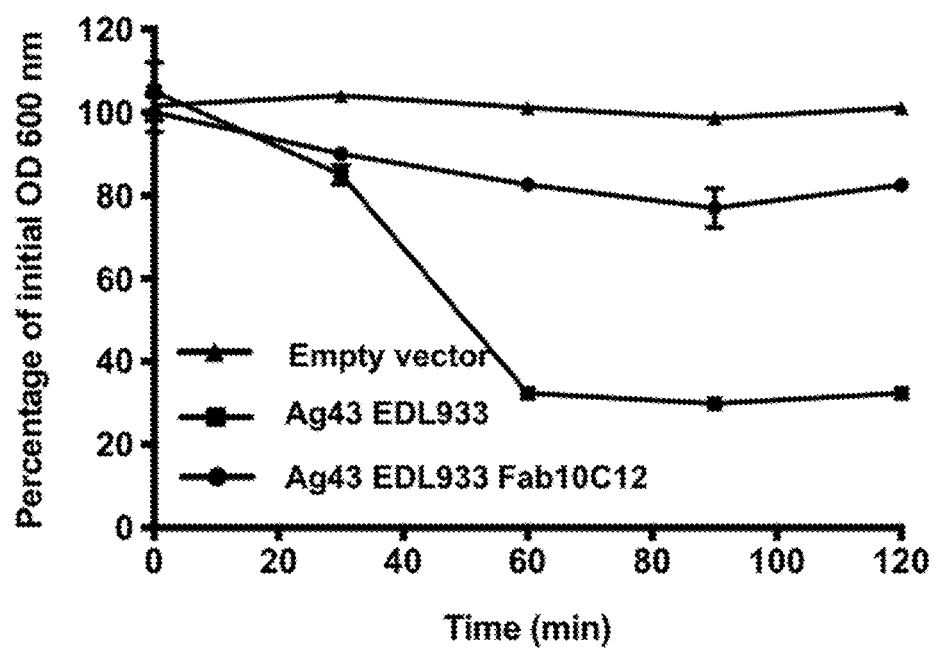
FIG. 13. Bacterial aggregation assay using enterohemorrhagic *E. coli* EDL933. Addition of Fab10C12 inhibited bacterial aggregation.

The 10C12 Fab fragment was tested for its ability to bind to Ag43 from EHEC strain EDL933 and to inhibit bacterial aggregation. Cell aggregation was assayed using methods similar to those described in Example 4. Referring to FIG. 13, Fab10C12 was effective at inhibiting aggregation of EDL933 cells.

Example 14: Autotransporter-Mediated Surface Attachment

Materials and Methods

Table 9 lists certain plasmids that were used in the present example.

TABLE 9

Plasmids used in the present example

| Plasmid | Description |
|---|---|
| pα$^{UpaB}$ | upaB α-domain in pLicE |
| pα$^{UpaB\_\Delta t6\text{-}10}$ | upaB α-domain deletion t6-10 (192-343 amino acid residues of αUpaB) in pLicE |
| pα$^{UpaB\_\Delta t1\text{-}2}$ | upaB α-domain deletion t1-2 (37-97 amino acid residues of αUpaB) in pLicE |
| pα$^{UpaB\_\Delta t3\text{-}4}$ | upaB α-domain deletion t3-4 (98-156 amino acid residues of αUpaB) in pLicE |
| pα$^{UpaB\_\Delta t5\text{-}6}$ | upaB α-domain deletion t5-6 (157-222 amino acid residues of αUpaB) in pLicE |
| pα$^{UpaB\_\Delta t7\text{-}8}$ | upaB α-domain deletion t7-8 (223-285 amino acid residues of αUpaB) in pLicE |
| pα$^{UpaB\_G1}$ | upaB α-domain (E165A, N189A, Q197A, N200A, Q203A, K256A and N316A) in pLicE |
| pα$^{Upa\_G2}$ | upaB α-domain (F101A, Y130A, Y187A, F195A, L201G, L202G) in pLicE |
| pα$^{Upa\_G3}$ | upaB α-domain (E103A, D138A, E165A, E226A) in pLicE |
| pα$^{UpaB\_S1}$ | upaB α-domain (N116A, D119A, N146A, N175A, D217A, K245A, D246A, D281A, R310A and D336A) in pLicE |
| pα$^{UpaB\_S2}$ | upaB α-domain (N110A, K111A, N112A, D142A, N171A, D206A, D208A, N212A, N241A, N274A, N276A, N303A, N305A, K325A, D329A, D331A and D349A) in pLicE |
| pα$^{UpaB\_S3}$ | upaB α-domain (V151A, I221A, V249A, A252G, A253G, Y285A, Y312A and V339A) in pLicE |
| pα$^{UpaB\_G1,S1}$ | upaB α-domain (E165A, N189A, Q197A, N200A, Q203A, K256A, N316A) and (N116A, D119A, N146A, N175A, D217A, K245A, D246A, D281A, R310A and D336A) in pLicE |
| pUpaB | full length upaB in pSU2718 |
| pUpaB-$^{\Delta t1\text{-}2}$ | upaB α-domain deletion t1-2 (37-97 amino acid residues of αUpaB) in pSU2718 |
| pUpaB-$^{\Delta t3\text{-}4}$ | upaB α-domain deletion t3-4 (98-156 amino acid residues of αUpaB) in pSU2718 |
| pUpaB-$^{\Delta t5\text{-}6}$ | upaB α-domain deletion t5-6 (157-222 amino acid residues of αUpaB) in pSU2718 |
| pUpaB-$^{\Delta t7\text{-}8}$ | upaB α-domain deletion t7-8 (223-285 amino acid residues of αUpaB) in pSU2718 |
| pUpaB$^{G1}$ | upaB α-domain (E165A, N189A, Q197A, N200A, Q203A, K256A and N316A) in pSU2718 |
| pUpaB$^{G2}$ | upaB α-domain (F101A,Y130A,Y187A, F195A, L201G, L202G) in pSU2718 |
| pUpaB$^{G3}$ | upaB α-domain (E103A, D138A, E165A, E226A) in pSU2718 |
| pUpaB$^{S1}$ | upaB α-domain (N116A, D119A, N146A, N175A, D217A, K245A, D246A, D281A, R310A and D336A) in pSU2718 |
| pUpaB$^{S2}$ | upaB α-domain (N110A, K111A, N112A, D142A, N171A, D206A, D208A, N212A, N241A, N274A, N276A, N303A, N305A, K325A, D329A, D331A and D349A) in pSU2718 |
| pUpaB$^{S3}$ | upaB α-domain (V151A, I221A, V249A, A252G, A253G, Y285A, Y312A and V339A) in pSU2718 |
| pUpaB$^{G1,S1}$ | upaB α-domain (E165A, N189A, Q197A, N200A, Q203A, K256A, N316A) and (N116A, D119A, N146A, N175A, D217A, K245A, D246A, D281A, R310A and D336A) in pSU2718 |

The amino acid sequence of UpaB is set forth as SEQ ID NO: 43. UpaB from the UPEC strain CFT073 comprises an N-terminal signal sequence (residues 1-37), an α-domain (residues 8-500) and a β-domain (residues 501-776). The coding sequence for the upaB α-domain (α$^{UpaB}$; locus tag c0426) was amplified from genomic DNA and inserted into a modified version of a pMCSG7 vector (Heras et al. Proc. Natl Acad. Sci. USA. 2014. 111: 457-462), which encodes a N-terminal His$_6$-tag followed by a thioredoxin (TRX) domain and a TEV protease cleavage site. The resulting plasmid, pUpaBα, introduces three residues at the N-terminus upon removal of the His$_6$-TRX-tag with TEV. The α$^{UpaB}$ protein was expressed in E. coli BL21 (DE3) LysS cells (Invitrogen) using autoinduction (24 h at 30° C.) in the presence of appropriate antibiotics (ampicillin 100 μg/mL, chloramphenicol 34 μg/mL). Cells were harvested, resuspended in 25 mM Tris pH 7.5 and 150 mM NaCl and lysed by sonication. The lysate was cleared by centrifugation and loaded onto a HisTrap column (GE Healthcare). Proteins were eluted in a gradient of 0-500 mM imidazole. Fractions containing α$^{UpaB}$ were cleaved with TEV protease and the uncleaved protein was removed by further nickel affinity chromatography. Size exclusion chromatography (Superdex S-75 GE Healthcare) in 25 mM Hepes and 150 mM NaCl pH 7.0, was used to further purify α$^{UpaB}$.

Crystals of α$^{UpaB}$ were grown at 20° C. using the hanging-drop vapour-diffusion technique. Crystals grew at 20 mg/mL in 0.1 M sodium acetate pH 4.8, 0.2 M ammonium sulfate and 28% (w/v) PEG 4000. Crystals pre-equilibrated in reservoir solution containing 20% glycerol were flash-cooled in liquid nitrogen. Xenon derivatisation was performed using a Xenon chamber (Hampton Research) at 20 bar for 1 min before flash freezing.

Native data were collected (λ=0.954, −163° C.) from a single crystal with an ADSC Q315r CCD detector on the MX2 micro-crystallography beamline at the Australian Synchrotron. The data were integrated and scaled with HKL2000 (Otwinowski et al. Methods Enzymol. 1997. 276: 307-326). Anomalous data were collected (λ=1.3776, −163° C.) from 2 crystals at the MX2 beamline. This data was integrated, scaled and merged using XDS/XSCALE (Kabsch. Acta Crystallogr. D Biol. Crystallogr. 2010. 55: 125-132). All crystals belonged to spacegroup P3$_1$21 with similar cell dimensions of a≈69 Å, b≈69 Å, c≈166 Å and α=90.0°, β=90.0° and γ=120.0°. This was consistent with one α$^{UpaB}$ molecule per asymmetric unit. The structure of α$^{UpaB}$ was determined by single isomorphous replacement using anomalous signal from Xenon. SHELX C,D,E (Sheldrick. Acta Crystallogr. D Biol. Crystallogr. 2010. 66: 479-485) was used to find the Xenon atoms, phasing and density modification. Eight Xenon atoms were found per asymmetric unit. ARP/wARP (Langer et al. Nat. Protoc. 2008. 3: 1171-1179) was used for initial model building against the experimental phases. This model underwent rounds of manual model building using COOT and refinement using Refmac5 and phenix.refine to 1.97 Å using native data. The quality of the model was monitored during refinement by the Rfree value, which represented 5% of the data. The structure was validated by the MolProbity (Davis et al. Nucleic Acids Res. 2007. 35: W375-W383) server and the figures were created with PyMOL (DeLano. The PyMOL Molecular Graphics System, http://www.pymol.org). Ramachandran statistics showed 97.87% of residues in the most favoured region and 2.13% in the allowed regions.

Results

Figure 14:
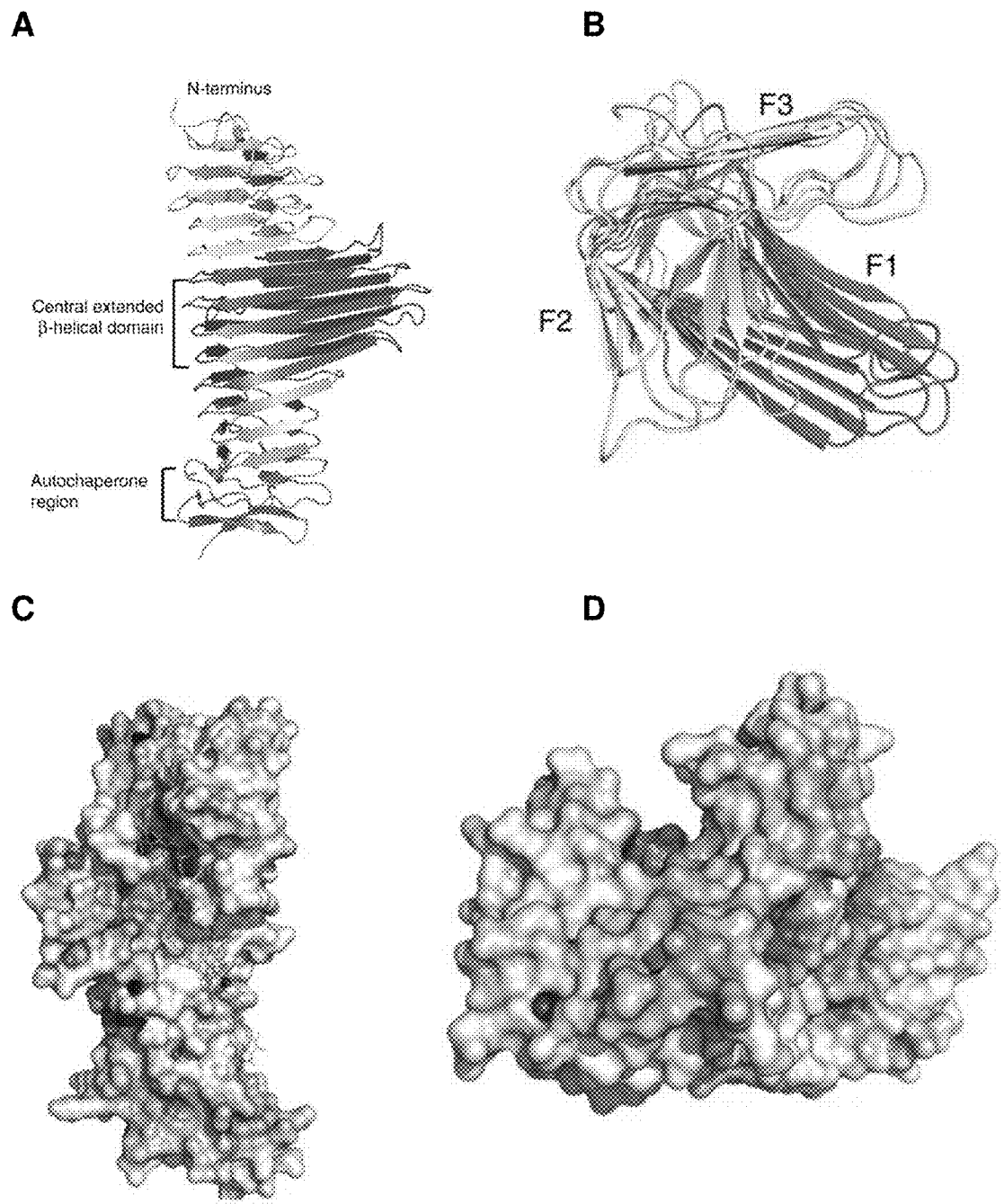
FIG. 14. A. Ribbon representation of the $\alpha^{UPaB}$ structure. B. Top view of $\alpha^{UPaB}$ showing F1, F2 and F3 faces. C. Surface representation of $\alpha^{UPaB}$ with GAG modelled into the $\alpha^{UPaB}$ groove. D. Top view surface representation of $\alpha^{UPaB}$.

The structure of $\alpha^{UpaB}$ exhibited a right-handed three-stranded β-helix with 13 turns (FIG. 14A), and each triangular turn containing three faces; F1, F2 and F3 (FIG. 14B). The β-helix is predominantly stabilised by an inter-strand network of hydrogen bonds. The interior of the β-helix is packed mostly by long stacks of aliphatic residues, whereas the exterior is largely acidic in nature. At the C-terminus of the β-helix, $\alpha^{UpaB}$ forms a two-stranded β-sandwich that is capped by a three-stranded β-meander motif. The β-strand extensions contributed by turns 6-10 and the long loops protruding between turns 2-6 form a long hydrophilic groove 11 Å wide and 12.5 Å deep on the F1 face of $\alpha^{UpaB}$ (FIGS. 14C and 14D). Sidechains from E165, S188, N189, Q197, T230 and E293 protrude into the groove and largely determine its slightly acidic nature.

The results of a DALI search using $\alpha^{UPaB}$ revealed that UpaB shared low structural similarity to polysaccharide degrading enzymes (1 BHE, 5GKD, 4C2L). The $\alpha^{UPaB}$ groove most closely resembled the glycosaminoglycan (GAG) lyase chondroitinase B (PDB 1OFL) from *Pedobacter heparinus* (Michel et al. J. Biol. Chem. 2004. 279: 32882-32896). Chondroitinase B is the closest homolog known to interact with human polysaccharides. $\alpha^{UPaB}$ shares a putative active site with chondroitinase B and other GAG lyases, located just outside of the groove. This site comprises UpaB Lys 256 and Lys 343 situated in similar positions to chondroitinase B Lys250/Arg271 Brønsted base/acid pair required to break the glycosidic bonds of GAGs (Garron and Cygler. Glycobiology. 2010. 20: 1547-1573). In chondroitinase B and other GAG lyases, the Lys250/Arg271 would be situated proximal to a bound calcium ion required for neutralisation of the GAG carboxylic group during bond cleavage. Indeed, electron density associated with the $\alpha^{UPaB}$ lysine pair likely to be a bound calcium was identified. Similar to other lyases, this calcium ion would be held in place by the neighbouring $\alpha^{UPaB}$ Glu 314 and Asn 316 residues. The likelihood of a GAG binding within the UpaB groove was tested using docking simulations (FIG. 14C). A model of a GAG was constructed and docked into the $\alpha^{UPaB}$ groove using Autodock Vina. All of the docking conformations showed an interaction with the $\alpha^{UpaB}$ groove, with one of the top conformations displaying an interaction with the putative lyase active site resembling a pre-cleavage state. This binding conformation exhibited a significant predicted binding affinity of −9.4 kcal/mol (free energy of binding), based on an extensive hydrogen bonding network between the GAG hydroxyl groups and a number of polar residues within and around the $\alpha^{UPaB}$ groove.

$\alpha^{UpaB}$ was then screened against 2788 compounds (including 88 carbohydrate molecules) in a fluorescence thermal shift-based assay. Significant binding was shown to two 'GAG-like' molecules; Tn Antigen GaIN-α1-O-Ser and lacto-N-neohexaose. GaIN-α1-O-Ser closely resembles the O-glycosidic-linked saccharide to serine complex that anchors most GAGs to their core proteins, and the lacto-N-neohexaose is representative of a main chain GAG (Hurst. World J. Urol. 1994. 12: 3-10). The role of the UpaB groove in this binding was shown by repeating this assay with a UpaB mutant ($\alpha^{UpaB})^{\cdot G1}$, designed by alanine substitutions to the prominent residues that stabilise the GAG interaction identified in the molecular docking studies (E165A, N189A, Q197A, N200A, Q203A, K256A and N316A). Although these alterations did not affect the secondary structure of $a^{UpaB\_G1}$, and $\alpha^{UpaB-G1}$ behaved in solution similar to the native protein, this mutant was unable to bind the GAG-like molecules as shown by overlapping melting curve plots of $\alpha^{UpaB-G1}$ in the presence and absence of the GAGs. Further analyses revealed that $\alpha^{UPaB}$ did not display a broad affinity for some common GAGs found in the urinary tract including chondroitin sulfate A, B, C and heparin sulfate.

Figure 15:
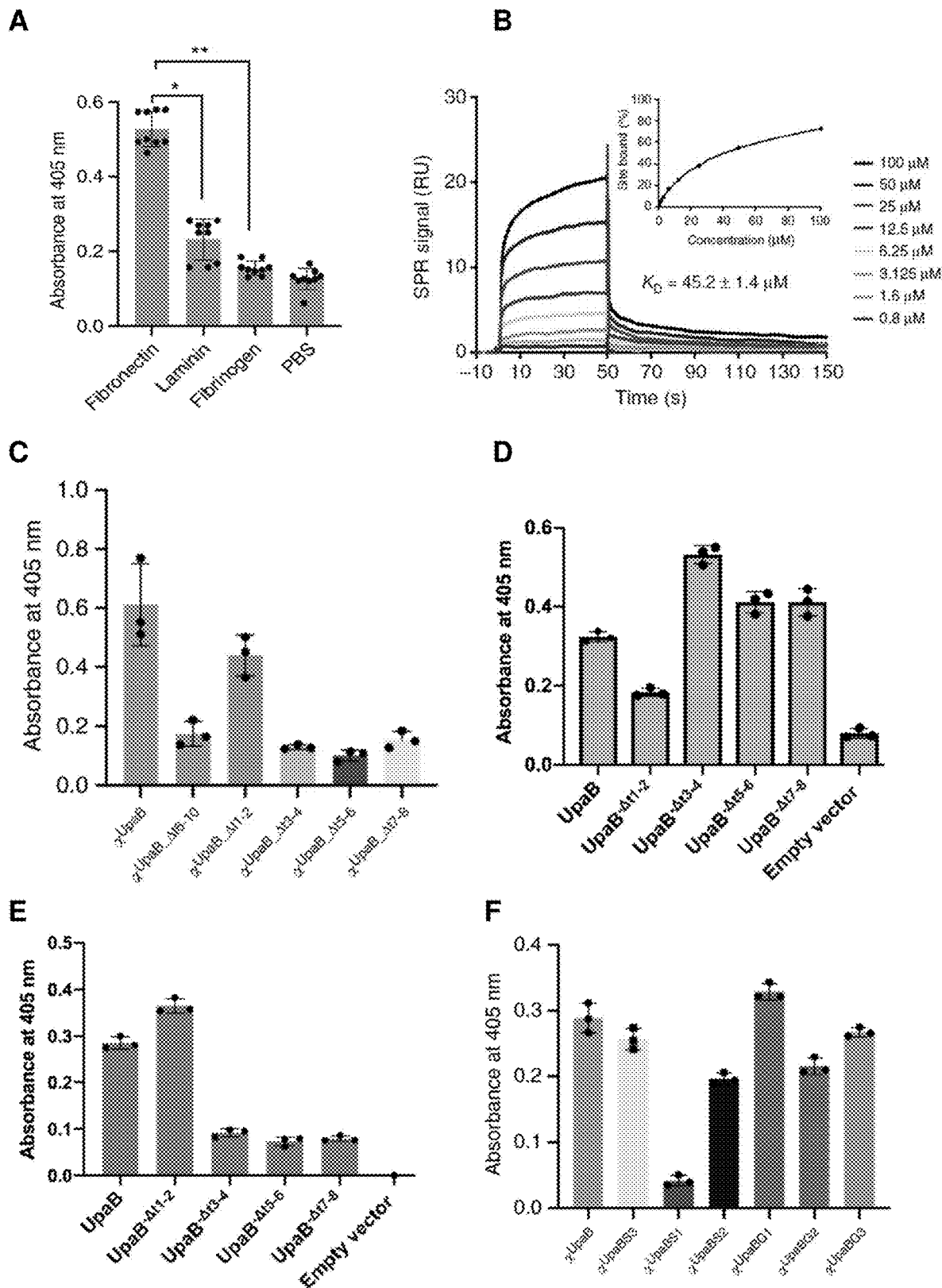
FIG. 15. A. Assessment of UpaB binding to human fibronectin, laminin and fibrinogen by ELISA. Statistical significance was determined by unpaired two-sample t test, *P<0.001, n=9; **P<0.001, n=9. B. SPR analysis of $\alpha^{UPaB}$ binding to immobilised fibronectin. A series of concentrations (0.8-100 µM) of $a^{UPaB}$ were injected over fibronectin. The apparent $K_D$ was determined using a steady-state affinity model. The data are expressed as mean±SEM of three replicates. C. Assessment of binding to fibronectin by UpaB deletion mutants using ELISA and a fibronectin-specific polyclonal antibody. $\alpha^{UPaB}$ (native) was included as a control. Data are shown as the means±standard deviation of three replicates. D. Whole cell ELISA demonstrating expression of full-length UpaB deletion mutants on the *E. coli* cell surface. E. Whole cell ELISA demonstrating binding of fibronectin to immobilised *E. coli* cells expressing UpaB or mutant derivatives. (Bound fibronectin was detected using anti-fibronectin antibody in an ELISA). An isogenic control strain containing empty vector pSU2718 was used a negative control. All data are shown as the means±standard deviation of 3 replicates. F. Assessment of binding to fibronectin by UpaB mutants containing targeted amino acid substitutions using ELISA and a fibronectin-specific polyclonal antibody. Targeted changes were made to various surface features of UpaB including an acidic patch $\alpha^{UPaB\_S1}$ (N116A, D119A, N146A, N175A, D217A, K245A, D246A, D281A, R310A and D336A) and polar patch $\alpha^{UPaB\_S2}$ (N110A, K111A, N112A, D142A, N171A, D206A, D208A, N212A, N241A, N274A, N276A, N303A, N305A, K325A, D329A, D331A and D349A) on the F2 face, a hydrophobic patch $\alpha^{UPaB\_S3}$ (V151A, I221A, V249A, A252G, A253G, Y285A, Y312A and V339A) between the F2 and F3 faces, along with a hydrophobic $\alpha^{UPaB\_G2}$ (F101A, Y130A, Y187A, F195A, L201G, L202G, Y260A) and acidic patch $\alpha^{UPaB\_G3}$ (E103A, D138A, E165A, E226A) within the GAG binding groove. Binding to fibronectin by $\alpha^{UPaB\_G1}$ (E165A, N189A, Q197A, N200A, Q203A, K256A and N316A) was also tested.

The ability of $\alpha^{UPaB}$ to bind to fibronectin (FN), laminin and fibrinogen was tested. The strongest association was observed between $\alpha^{UPaB}$ and FN (FIG. 15A). Using SPR, a $K_D$ of 45.2±1.4 μM between UpaB and FN was determined (FIG. 15B), with the latter immobilised to a CM5 sensor chip. To determine the region of $\alpha^{UPaB}$ that binds FN, a series of $\alpha^{UPaB}$ mutants with specific deletions in β-strands were constructed, expressed and purified. Deletion of the region encompassing the extended β-strands in turns 6-10 ($\alpha^{UpaB-\Delta t6-10}$) resulted in a significant reduction in binding to FN (FIG. 15C). Further analysis involving the progressive deletion of pairs of β-strand turns from the $\alpha^{UPaB}$ N-terminus through the extended β-strand region, generating $\alpha^{UpaB-\Delta t1-2}$, $\alpha^{UpaB-\Delta t3-4}$, $\alpha^{UpaB-\Delta t5-6}$ and $\alpha^{UpaB-\Delta t7-8}$, demonstrated that the highest loss in FN binding was caused by deletion of turns 3-8. As such, most of the region encompassing the β-strand extensions comprises the primary site for binding FN. Subsequent whole-cell ELISA experiments showed that *E. coli* expressing these UpaB mutant proteins bound to FN in a manner consistent with the results obtained using purified recombinant proteins (FIGS. 15D and 15E).

Utilising the $\alpha^{UpaB\_G1}$ GAG-binding mutant, along with other mutants containing amino acid substitutions of hydrophobic ($\alpha^{UpaB\_G2}$) and acidic ($\alpha^{UpaB\_G3}$) residues within the groove, these regions were found to have little effect on FN binding as determined by ELISA (FIG. 15F). The other $\alpha^{UPaB}$ faces were examined for possible sites that could bind FN. Amino acid substitutions were made to a predominantly acidic patch ($\alpha^{UpaB\_S3}$) and polar region ($\alpha^{UpaB\_S2}$) on the F2 face and a hydrophobic patch ($\alpha^{UpaB\_S3}$) between the F2 and F3 faces (FIG. 15F). Substitution of residues N116, D119, N146, N175, D217, K245, D246, D281, R310 and D336 on the F2 face to alanine ($\alpha^{UpaB\_S1}$) caused almost complete loss of FN binding as determined by ELISA, while maintaining the correct secondary structure of $\alpha^{UpaB\_S1}$ based on circular dichroism spectroscopic analysis and displaying a behaviour in solution similar that of the native protein. This result mapped the FN-binding site to a ladder of charged/polar residues that are contributed from β-strands or loops in consecutive rungs of the $\alpha^{UPaB}$ β-helix.

Figure 16:
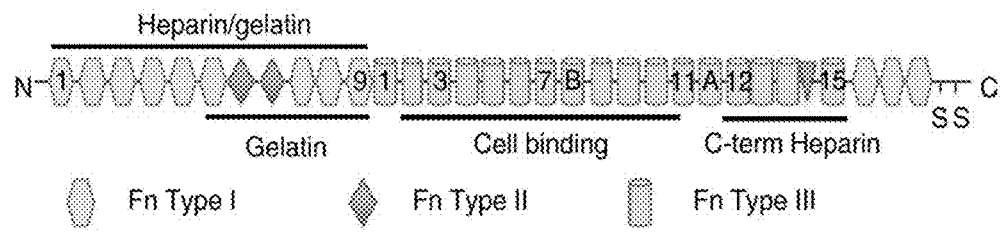
FIG. 16. A. Fibronectin domain organisation composed of 12 type I modules (FnI), 2 type II modules (FnII) and 15-17 type III modules (FnIII). B. Binding of fibronectin fragments, as well as full-length (FL) fibronectin, to UpaB measured by ELISA. Data are shown as the mean±standard deviation of three replicates. C. Model of the UpaB-FnIII interaction derived from NAMD simulations using the structures of UpaB and the FnIII$_{1-2}$ fragment (PDB: 2HA1), showing predominately hydrogen bonding between charged residues of UpaB (in particular, D246, D310, D336 and D375) and FnIII$_1$ (residues K32, R36, K40 and E70).
Figure 16:
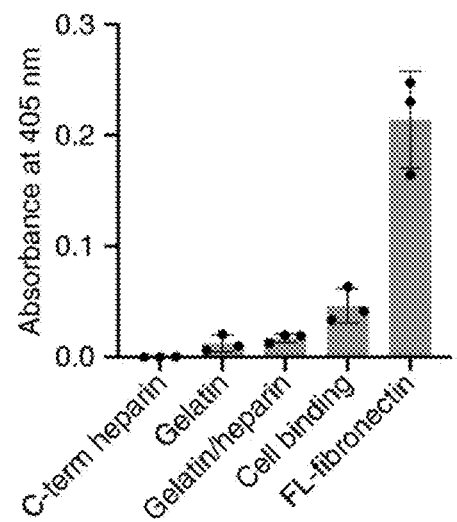
Figure 16:
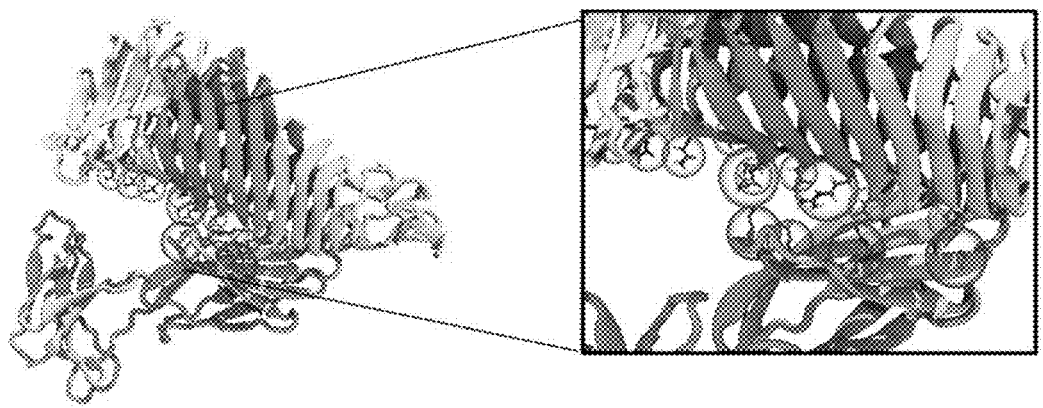

Commercially available fragments of human FN which include a 45 kDa gelatin-binding fragment (FnI$_{6-9}$, FnII$_{1-2}$), a 70 kDa heparin/gelatin-binding fragment (FnI$_{1-9}$, FnII$_{1-2}$), a 120 kDa cell-binding fragment (FnIII$_{2-11}$) and a 40 kDa C-terminal heparin-binding fragment (FnIII$_{12-15}$) were obtained (FIG. 16A). The binding of $\alpha^{UPaB}$ to these FN fragments determined by ELISA revealed that it displayed strongest interaction with the cell binding fragment (FnIII$_{2-11}$) and weak binding to the gelatin (FnI$_{6-9}$, FnII$_{1-2}$) and heparin/gelatin (FnI$_{1-9}$, FnII$_{1-2}$) (FIG. 16B). Given the size of UpaB, this maps its binding site on FN to the first FnIII units in the cell-binding fragment, possibly also including some interaction with the neighbouring FnI units in the gelatin-binding fragment (note that the gelatin [FnI$_{6-9}$, FnII$_{1-2}$] and heparin/gelatin [FnI$_{1-9}$, FnII$_{1-2}$] fragments overlap in this region).

This interaction was investigated using molecular dynamics simulations with the $\alpha^{UPaB}$ crystal structure and the structure of human FnIII$_{1-2}$ (2HA1) (Vakonakis et al. EMBO J. 2007. 26: 2575-2583) (FIG. 16C). To visualise this interaction, simulations were also run with the $\alpha^{UPaB\_S1}$ mutant that had lost its capacity to bind FN. Modelling simulations were performed using NAMD 2.12 (Phillips et al. J. Comput. Chem. 2005. 26: 1781-1802) for a cumulative total of 1.2 µs for each system (3 replicates of 400 ns each). The simulations provide plausible binding mechanisms, showing that $\alpha^{UPaB}$ could interact with FnIII via complementary charged residues without unfolding and/or donating β-strands. Specifically, the $\alpha^{UPaB}$-FnIII$_{1-2}$ simulations indicate that $\alpha^{UPaB}$ primarily interacts with FnIII$_1$ through hydrogen bond interactions mediated by $\alpha^{UPaB}$ D246, R310, D336 and D375 residues with complementary charged areas on FnIII, particularly residues K32, K40, E70, R36 and of FnIII$_1$. Substitutions of the $\alpha^{UPaB}$ FnIII-interacting residues to alanine in the $\alpha^{UPaB\_S1}$ mutant greatly reduced hydrogen bond interactions observed in the simulations.

To determine whether the structural features of UpaB required for binding FnIII and GAGs are conserved across *E. coli*, several draft and complete *E. coli* genome sequences were screened. The UpaB gene was present in 1019 strains and was found in UPEC strains as well as intestinal pathogenic, commensal and other extra-intestinal pathogenic strains. Analysis of these 1019 translated UpaB amino acid sequences revealed that 95% (968/1019) shared an amino acid sequence identity >89%. Comparison of the translated UpaB amino acid sequence from seven completely sequenced UPEC strains showed that the putative GAG lyase active site was strictly conserved; there was also high conservation of the residues that contribute to the acidic groove, as well as the residues that interact with FnIII.

Figure 17:
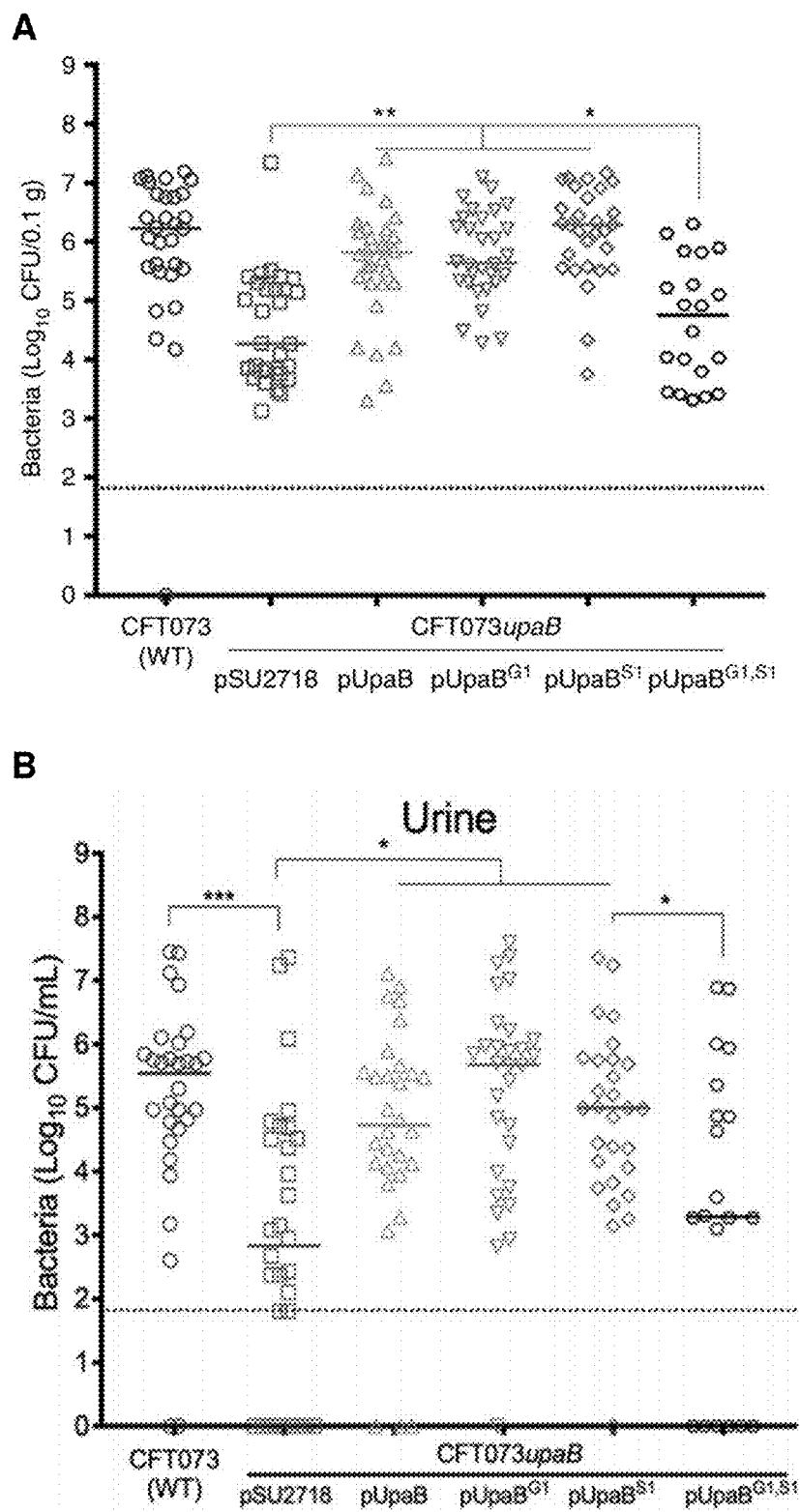
FIG. 17. A. UPEC colonisation of the mouse bladder is enhanced by UpaB GAG- and fibronectin-binding interactions. C57BL/6 mice were challenged transurethally with wild-type CFT073, CFT073upaB(pSU2718), CFT073upaB (pUpaB), CFT073upaB(pUpaB$^{G1}$), CFT073upaB(pUpaB$^{S1}$) and CFT073upaB(pUpaB$^{G1, S1}$). The results represent log$_{10}$ CFU/0.1 g bladder tissue of individual mice at 24 h post-infection, and the horizontal bars mark group medians. A minimum of 20 mice were assessed per group (pooled from at least 2 independent experiments). Data were compared using Kruskal-Wallis ANOVA with Dunn's multiple comparisons correction (*P<0.05; **P<0.01). B. C57BL/6 mice were challenged transurethally with WT CFT073, CFT073upaB(pSU2718), CFT073upaB(pUpaB), CFT073upaB(pUpaB$^{G1}$), CFT073upaB(pUpaB$^{S1}$) and CFT073upaB(pUpaB$^{G1, S1}$). The results represent log$_{10}$ CFU per ml of urine of individual mice at 24 h post-infection, and the horizontal bars mark group medians. A minimum of 20 mice were assessed per group (pooled from at least 2 independent experiments). Data were compared using Kruskal Wallis ANOVA with Dunn's multiple comparisons correction (*P<0.05; ***P<0.005).

To examine how the GAG- and FN-binding properties of UpaB impact its function in vivo, plasmids containing the S1, G1 and double S1-G1 mutations in the full-length UpaB gene were constructed. These plasmids were transformed into a UpaB mutant strain (CFT073UpaB) to generate a set of strains with plasmid pSU2718 (vector control), pUpaB (wild-type (WT) UpaB), pUpaB$^{G1}$ (UpaB with mutated GAG-binding site), pUpaB$^{S1}$ (UpaB with mutated FN-binding site) or pUpaB$^{G1,S1}$ (UpaB with mutated GAG- and FN-binding sites). Next, the capacity of the CFT073UpaB-complemented strains to colonise the mouse bladder was determined. In these experiments, CFT073UpaB complemented with pUpaB, pUpaB$^{G1}$ and pUpaB$^{S1}$ restored bladder colonisation at 24 h post-infection to a level equivalent to colonisation by WT CFT073 (FIG. 17A). In contrast, complementation with either the vector control plasmid pSU2718 or pUpaB$^{G1,S1}$ did not restore bladder colonisation to WT levels, and these levels were significantly reduced at 24 h post-infection compared to colonisation by CFT073UpaB containing pUpaB, pUpaB$^{G1}$ or pUpaB$^{S1}$ (FIG. 17A). Western blot analysis and whole-cell ELISA showed that this lack of complementation by pUpaB$^{G1, S1}$ was not due to lack of expression of the mutant protein on the cell surface. The stability of the pUpaB$^{G1, S1}$ mutant was also confirmed by purification and biophysical characterisation of recombinant $\alpha^{UPaB\_G1,S1}$. A similar colonisation profile was observed for each of the UPEC strains in the urine of these experimentally infected mice (FIG. 17B).

It will be understood from these results that autotransporter-mediated attachment of a bacterium to a surface such as a cellular surface may be inhibited by contacting the bacterium with an autotransporter-binding molecule.

It will be appreciated by those skilled in the art that the present disclosure may be embodied in many other forms.

The invention claimed is:

1. An isolated antibody or antigen binding fragment thereof comprising:
   a) a CDRH1 comprising the sequence set forth in SEQ ID NO: 3;
      a CDRH2 comprising the sequence set forth in SEQ ID NO: 4;
      a CDRH3 comprising the sequence set forth in SEQ ID NO: 5;
      a CDRL1 comprising the sequence set forth in SEQ ID NO: 6;
      a CDRL2 comprising the sequence set forth in SEQ ID NO: 7; and
      a CDRL3 comprising the sequence set forth in SEQ ID NO: 8; or
   b) a CDRH1 comprising the sequence set forth in SEQ ID NO: 15;
      a CDRH2 comprising the sequence set forth in SEQ ID NO: 16;
      a CDRH3 comprising the sequence set forth in SEQ ID NO: 17;
      a CDRL1 comprising the sequence set forth in SEQ ID NO: 18;
      a CDRL2 comprising the sequence set forth in SEQ ID NO: 19; and
      a CDRL3 comprising the sequence set forth in SEQ ID NO: 20.

2. The isolated antibody or antigen binding fragment thereof of claim 1, further comprising:
   a) a heavy chain variable region (VH) comprising the sequence set forth in SEQ ID NO: 9 or a sequence having at least 90% identity to SEQ ID NO: 9, and a light chain variable region (VL) comprising the sequence set forth in SEQ ID NO: 10 or a sequence having at least 90% identity to SEQ ID NO: 10; or
   b) a VH comprising the sequence set forth in SEQ ID NO: 21 or a sequence having at least 90% identity to SEQ ID NO: 21, and a VL comprising the sequence set forth in SEQ ID NO: 22 or a sequence having at least 90% identity to SEQ ID NO: 22.

3. The isolated antibody or antigen binding fragment thereof of claim 1, wherein the antibody or antigen binding fragment binds to Ag43a (SEQ ID NO: 1) at an epitope comprising one or more residues selected from the group consisting of N83, R113, N114, D133, N150, T151, T152, G169, R254, E270, T291, T310, R330, G332, A333, S335, T361, N362, R364, T380, T381, S383, N386, S399, T401, D404 and G405.

4. The isolated antibody or antigen binding fragment thereof of claim 1, wherein the antibody or antigen binding fragment a) specifically binds to an autotransporter or b) reduces binding of one autotransporter molecule to another autotransporter molecule.

5. An isolated nucleic acid encoding a) the antibody or antigen binding fragment thereof of claim 1 or b) the VH or the VL of the antibody or antigen binding fragment thereof.

6. An isolated nucleic acid encoding a) the antibody or antigen binding fragment thereof of claim 2 or b) the VH or VL of the antibody or antigen binding fragment thereof.

7. An isolated expression vector comprising the isolated nucleic acid of claim 5 or 6.

8. A host cell comprising the isolated nucleic acid of claim 5 or 6.

9. A method comprising culturing the host cell of claim 8 under conditions that allow production of the antibody or antigen binding fragment, or VH or VL of the antibody or antigen binding fragment, and purifying the antibody or antigen binding fragment, or VH or VL of the antibody or antigen binding fragment, from the host cell.

10. A composition comprising the isolated antibody or antigen binding fragment thereof of claim 1 and an antibiotic agent.

11. A method of reducing aggregation of two or more bacteria the method comprising contacting the two or more bacteria with an effective amount of the antibody or antigen binding fragment thereof of claim 1.

12. A method of inhibiting interaction between two or more autotransporter molecules the method comprising contacting at least one of said two or more autotransporter molecules with the antibody or antigen binding fragment thereof of claim 1.

13. A method of treating a bacterial infection in a subject, the method comprising administering to the subject a therapeutically effective amount of the antibody or antigen binding fragment thereof of claim 1.

14. A method of treating a disease or disorder associated with a bacterial infection in a subject the method comprising administering to the subject a therapeutically effective amount of the antibody or antigen binding fragment thereof of claim 1.

* * * * *